(12) United States Patent
Armistead et al.

(10) Patent No.: US 6,495,558 B1
(45) Date of Patent: Dec. 17, 2002

(54) KINASE INHIBITORS

(75) Inventors: David M. Armistead, Sudbury, MA (US); Jean E. Bemis, Arlington, MA (US); Daniel Elbaum, Newton, MA (US); Gregory J. Habgood, Merrimac, MA (US); Perry M. Novak, Milford, MA (US); Joseph J. Nunes, Andover, MA (US); Leticia M. Toledo-Sherman, Somerville, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/528,976

(22) Filed: Mar. 21, 2000

Related U.S. Application Data

(63) Continuation-in-part of application No. 09/488,582, filed on Jan. 21, 2000, now abandoned.
(60) Provisional application No. 60/116,697, filed on Jan. 22, 1999.

(51) Int. Cl.$^7$ ..................... C09D 239/36; A61K 31/513
(52) U.S. Cl. ........................................ 514/272; 544/321
(58) Field of Search ......................... 514/272; 544/322, 544/324, 321

(56) References Cited

U.S. PATENT DOCUMENTS

| | | | | |
|---|---|---|---|---|
| 3,257,400 A | * | 6/1966 | Wagner ................... | 260/256.4 |
| 3,378,557 A | | 4/1968 | Rorig, et al. ............ | 260/247.2 |
| 3,980,781 A | | 9/1976 | Snell et al. ................. | 514/272 |
| 4,000,138 A | | 12/1976 | Snell et al. ............... | 260/256.4 |
| 4,308,272 A | | 12/1981 | Wierenga et al. ........... | 424/251 |
| 4,689,328 A | | 8/1987 | Hall et al. ................... | 514/274 |
| 4,786,638 A | | 11/1988 | Bagli et al. ................. | 514/252 |
| 4,786,640 A | | 11/1988 | Bagli et al. ................. | 515/269 |
| 4,900,829 A | | 2/1990 | Bagli et al. ................. | 544/319 |
| 4,906,753 A | | 3/1990 | Bagli et al. ................. | 544/319 |
| 5,300,477 A | | 4/1994 | Tice ........................... | 504/242 |
| 5,434,157 A | * | 7/1995 | Wierenga et al. ........... | 514/272 |
| 5,453,414 A | | 9/1995 | Tice et al. .................. | 504/133 |
| 5,726,124 A | | 3/1998 | Tice et al. .................. | 504/193 |

FOREIGN PATENT DOCUMENTS

| | | | |
|---|---|---|---|
| DE | 71767 | 3/1970 | |
| DE | 129907 | 2/1978 | ......... C07D/239/38 |
| DE | 136500 | 7/1979 | ......... C07D/495/04 |
| DE | 3816994 A1 | 11/1989 | .......... A01N/43/54 |
| EP | 663396 A1 | 7/1995 | ......... C07D/239/36 |
| GB | 1223686 | 3/1971 | ............ A01N/9/20 |
| GB | 2048250 A | 12/1980 | ......... C07D/239/47 |
| GB | 2107309 A | 4/1983 | ......... C07D/239/36 |
| GB | 2158068 A | 11/1985 | ......... C07D/239/47 |
| JP | 61205260 | 9/1986 | ......... C07D/239/47 |
| JP | 03031267 | 2/1991 | ......... C07D/239/47 |
| WO | WO 97/33883 A | 9/1997 | ......... C07D/401/04 |
| WO | WO97/44326 A | 11/1997 | ......... C07D/239/42 |
| WO | WO 98/18782 | 3/1998 | ......... C07D/401/04 |
| WO | WO 98/14504 A | 4/1998 | ........... C08G/85/00 |
| WO | WO 98/25596 A | 6/1998 | .......... A61K/31/00 |
| WO | WO 00/13688 A | 3/2000 | ......... A61K/31/505 |

OTHER PUBLICATIONS

Simone. Introduction: Oncology, Cecil Textbook of Medicine, 20th Edition, vol. 1, pp. 1004–1010, 1996.*

Prabhakar, et al. A QSAR Study on the Antileishmanial Activity of Some Substituted Pyrimidines and Pyrazolo [1,5–a] pyrimidines, Jul. 19, 1997, Indian J. Pharm. Sci., 59(6), pp. 286–291.

Attaby, et al. Reactions of Pyrimidinonethione Derivatives: Synthesis of 2–Hydrazinopyrimidin–4–Arthydrazonopyrimidine Derivatives, 1997, Arch. Pharm. Res., 20(6), pp. 620–628.

Khodair, et al. Glycosylation of 2–Thiouracil Derivatives, A Synthetic Approach to 3–Glycosyl–2,4–dioxypyrimidines, 1997, Nucleosides & Nucleotides, 16(4), pp. 433–444.

Abdel–Aziz, et al. Fused Cyanopyrimidines: Part II Synthesis and Reactions of Fused Cyanopyrimidine Derivatives as Affecting Enzymatic Agents. 1996, Phosphorus, Sulfur, and Silicon 113(1–4), pp. 67–77.

Ram, et al. 5–Cyano–2–Thiouracils and Their Derivatives: A New Class of Leishmanicides. 1994, Bioorganic & Medicinal Chemistry Letters, 4(22), pp. 2653–2656.

Manhi et la. Reactions With 6–Substituted–2–Thiouracil–5–Carbonitriles, Synthesis of Tetrazolo[1,5–c] and Ditetrazolo [1,5–a:1,5–c] Pyrimidines. 1992, Egypt J. Pharm. Sci., 33(5–6), pp. 825–838.

Rashed, et al. Synthesis of [1,5–a] Pyrimidinone Ring Derivatives. 1993, J. of Chinese Chemical Society, 40(4), pp. 393–397.

Patzel, et al. Ring Chain Transformations: XI: Synthesis of Semicyclic 3–(Aminoalkylideneamino)–3–aryl–2–propenenitriles and Their Ring Chain Transformation to 2–(w–Aminoalkyl)–6–aryl–4–halo–5–pyrimidinescarbon itriles, 1993, Synthesis, (5), pp. 525–529.

Ram, et al. Chemotherapeutic agents XXV: synthesis and leishmanicidal activity of carbazolylpyrimidines. 1992, Eur. J. Med. Chem., 27, pp. 851–855.

Ismail, et al. Synthesis and Some Reactions of Pyrimidinone Derivatives, 1990, Egypt. J. Chem., 33(3), pp. 221–232.

(List continued on next page.)

Primary Examiner—Deepak R. Rao
(74) Attorney, Agent, or Firm—Frank S. Ungemach; Stuart L. Watt

(57) ABSTRACT

The invention relates to inhibitors of kinases, compositions comprising the inhibitors, and methods of using the inhibitors and inhibitor compositions. The inhibitors and compositions comprising them are useful for treating disease or disease symptoms. The invention also provides for methods of making kinase inhibitor compounds, methods of inhibiting kinase activity, and methods for treating disease or disease symptoms.

5 Claims, No Drawings

OTHER PUBLICATIONS

Hassan, et al. Reactivity of 6–anisyl–5–cyano–4–oxo–2–thioxo–1,2,3,4–tetrahydro–pyrimidine towards some electrophiles and nucleophiles. 1991, Chinese Journal of Chemistry, 9(3), pp. 262–269.
Ram, et al. Synthesis of π–Deficient Pyrimidines as Leishmanicides. 1991. Arch. Pharm. (Weinheim), 324, pp. 837–839.
Ram, et al. Chemotherapeutic agents: Part XXII–Synthesis of π–deficient pyrimidines as leishmanicides. Oct. 1991, Indian J. Chem., 30B, pp. 962–965.
Abdel–Hady, et al. Synthesis of Some Thieno [2,3,-d] Pyrimidines. 1989, Sulfur Letters, 9(3), pp. 101–108.
Ram, Synthesis of Pyrimidines and Fused Pyrimidines as Leishmanicides and Herbicides. 1989, Journal of prakt. Chemie., 331(6), pp. 893–905.
Ram, et al. Chemotherapeutic Agents: Part XX–Antileishmanial and immunoadjuvant activities of rationally designed thiopyrimidines. Dec. 1990, Indian Journal of Chemistry, 29B(12), pp. 1129–1133.
Ram, et al. Chemotherapeutic Agents XI: Synthesis of Pyrimidines and azolopyrimidines as leishmanicides. 1990, Eur. J. Med. Chem., 25 (6), pp. 533–538.
Ram, et al. Chemotherapeutic Agents XVI[1]: Synthesis of Pyrimidines and Fused Pyrimidines as Leishmanicides. 1989, Journal of Prakt. Chemie. Section 331 (6), pp. 957–963.
Ram, et al. Chemotherapeutic Agents XIX [1]: Synthesis of [1,2,4]–Triazoloquinazolinones and Related Compounds as Antihypertensive Agents. 1990, Journal f. Prakt. Chemie., Section 332(5), pp. 629–639.
Ram, et al. Chemotherapeutic Agents: Part XIV–Synthesis of π–deficient pyrimidines linked with π–rich heterocycles as antimicrobal agents. Feb. 1989, Indian Journal of Chemistry, 28B, pp. 159–162.
Ellingboe, et al. (Pyrimidinyloxy) acetic Acids and Pyrimidineacetic Acids as a Novel Class of Aldose Reductase Inhibitors. 1990, J. Med. Chem., 33 (10), pp. 2892–2899.
Sadek, et al. Activated Nitriles in Heterocyclic Synthesis. Synthesis of Pyrimidine Derivatives. 1988, Bull. Chem. Soc. Jpn., 61(2), pp. 539–541.
Ram, et al. Syntheses and Activities of Novel Pyrimidines Derived from 5–Cyano–6–aryl–2–thiouracil. 1987, Liebigs Ann. Chem., (9), pp. 797–801.
Hussain, et al. A One–Step Synthesis of 2–Methylthio–6–oxopyrimidine Derivatives: Preparation of Fused Pyrimidinones. 1985, J. Heterocyclic Chem., 22(1), pp. 169–171.
Lorente, et al. Synthesis of Heterocyclic Compounds, XXXIX. Synthesis of 5–Cyano–2–phenyl–4–thioxo–3,4–dihydropyrimidines. 1985, J. Heterocyclic Chem., 22(1), pp. 49–51.
Ram, et al. 5–Cyano–6–aryluracil and 2–Thiouracil Derivatives as Potential Chemotherapeutic Agents. IV. 1984, J. Heterocyclic Chemistry, 21(5), pp. 1307–1312.

Brana, et al. Reaction of N–(1–Oxido–4–Pyridylmethyl)–3,5–DimethylBenzamide with Malononitrile in Acetic Anhydride, 1984, Heterocycles. 22(1), pp. 113–115.
Abd–Elfattah, Reactions with α–Substituted Cinnamonitriles. A Novel Synthesis of Arylpyrimidines. 1983, Tetrahedron, 39 (19), pp. 3197–3199.
Elnagdi, et al. Activated Nitriles in Heterocyclic Synthesis: A New Procedure for the Synthesis of Pyrimidine Derivatives. 1982, J. Chem. Soc., Perkin Trans. I(11), pp. 2667–2670.
Yamamoto, et al. Reactions of 1,3–Thiazine–2,6–dithiones. Part 3. New General Synthetic Method for Pyrimidine–4 (3H)–thiones. 1982, J. Chem. Research, Synop. (10), pp. 274–275.
Kobayashi, et al. Anti–Tumor Activity of Indole Derivatives. 1977, Yakugaku Zasshi, 97(9), pp. 1033–1039.
Weidinger, et al. Synthesen von 4,5–disubstituierten 2.6–Diaryl–pyrimidinen. 1968, Liebigs Ann. Chem., 716, pp. 143–146.
Kobayashi, et al. Studies on Indole Derivatives. V. Reaction of 3–Methylthio–3–(3–indolyl) acrylic acid Drivatives with Some Amines. 1967, Yakugaku Zasshi, 87(7), pp. 857–860.
Ram, Chemotherapuetic Agents XVIII: Synthesis of π–Deficient Pyrimidines and Fused Pyrimidines as Leishmanicidal Agents. 1990, Arch. Pharm.(Weinheim), 323 (11), pp. 895–899.
Eshba, Synthesis of some Substituted Pyrimidines and 1,2,4–Triazolo[4,3–a]Pyrimidines as Potential Chemotherapeutic Agents. 1995, Alexandria Journal of Pharmaceutical Science. 9 (1), pp. 31–34.
Kambe, et al. A One Step Synthesis of 4–Oxo–2–thioxopyrimidine Derivatives by the Ternary Condensation of Ethyl Cyanoacetate, Aldehydes, and Thiourea. 1979, Synthesis, 4, pp. 287–289.
Hussain, et al. Reactions with 2–Mercaptopyrimidines. Synthesis of Some New Thiazolo[3,2–α]–and Triazolo[4,3–α] Pyrimidines. 1987, Journal of Heterocyclic Chemistry, 24 (6), pp. 1605–1610.
El–Reedy, et al. Azolopyrimidines and Pyrimidoquinazolines From 4–Chloropyrimidines. 1989, Journal of Heterocyclic Chemistry, 26 (2), pp. 313–316.
Parmar, et al. Synthesis of azetidinones and thiazolidinones from hydrazinopyrimidine as potential antimicrobal agents, 1999, Indian Journal of Chemistry, 38B (4), pp. 440–444.
Keana, et al. Diels–Adler reactions Involving Heterocyclic Dienophiles. Sythesis of Substituted Hydroquinazolines and 1,3–Diazaspiro[4.5]decadienes. 1976, Journal of Organic Chemistry, 41 (12) pp. 2124–2129.
Furukawa, et al. Reaction of Biguanides and Related Compounds. XV. Cyclizations of Arylbiguanides and 2–Guanidinobenzimidazole with Bifunctional Unsaturated Dicarboxylates to s–Triazines and Imidazolines. 1983, Chemical and Pharmaceutical Bulletin, 31 (7), pp. 2473–2479.

* cited by examiner

KINASE INHIBITORS

This application is a continuation-in-part of U.S. Ser. No. 09/488,582 filed Jan. 21, 2000 now abandoned which claims priority benefit under Title 35 USC §119(e) of U.S. Provisional Application No. 60/116,697, filed Jan. 22, 1999 and entitled Kinase Inhibitors, the entire contents of each being incorporated herein by reference.

BACKGROUND OF THE INVENTION

The invention relates to inhibitors of kinases, compositions comprising the inhibitors, and methods of using the inhibitors and inhibitor compositions. The inhibitors and compositions comprising them are useful for treating or modulating disease in which kinases may be involved, symptoms of such disease, or the effect of other physiological events mediated by kinases. The invention also provides for methods of making kinase inhibitor compounds and methods for treating diseases in which kinase activity is involved.

The protein kinases constitute a large family of structurally related enzymes that are responsible for the control of a wide variety of signal transduction processes within the cell. (See, Hardie, G. and Hanks, S. (1995) *The Protein Kinase Facts Book, I and II*, Academic Press, San Diego, Calif.). Protein kinases are thought to have evolved from a common ancestral gene due to the conservation of their structure and catalytic function. Almost all kinases contain a similar 250–300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.*, 9:576–596 (1995); Knighton et al., *Science*, 253:407–414 (1991); Hiles et al., *Cell*, 70:419–429 (1992); Kunz et al., *Cell*, 73:585–596 (1993); Garcia-Bustos et al., *EMBO J.*, 13:2352–2361 (1994)).

Since the structure of the catalytic subunit of cAMP-dependent protein kinase (cAPK) was elucidated, approximately two dozen additional kinase structures have been solved as either apo enzymes or binary and ternary complexes (with ATP, ATP analogs, metal ions, ADP, ATP competitive inhibitors in the absence or presence of peptide substrate or peptide inhibitors). These proteins share a structurally conserved catalytic domain comprising two lobes that can be further subdivided into twelve subdomains. The N-terminal portion forms the small lobe (including subdomains I–IV) whose architecture is composed of an antiparallel five-strand β-sheet and one α-helix, while the lower C-terminal domain forms another lobe (including subdomains VIA–XI) containing mostly α-helical architecture. Subdomain V spans the two lobes. The N-terminal domain is thought to participate in orienting the nucleotide (or other binding entity), while the C-terminal domain is thought to be responsible for binding peptide substrate and initiating phosphotransfer to the hydroxyl group of a serine, threonine, or tyrosine residue.

The N- and C-terminal domains are connected through a single peptide strand, to which the adenine moiety of ATP binds via an eleven membered hydrogen bond cycle, involving the N1 and the N6 amino group, and the backbone carbonyl and NH functions of two nonconsecutive residues. This linker acts as a hinge about which the domains can rotate with respect to each other without disruption of the secondary architecture of the kinase. Several torsion angle changes in the linker backbone allow this movement to occur. The ribose group of ATP is anchored to the enzyme via hydrogen bonds with residues within the ribose-binding pocket. The triphosphate group is held in position via various polar interactions with several variable residues form the glycine rich loop, the conserved DFG motive and the catalytic loop.

Protein kinases may be characterized by their regulation mechanisms. It must be noted, however, that an individual protein kinase may be regulated by more than one mechanism. These mechanisms include, for example, autophosphorylation, transphosphorylation by other kinases, protein-protein interactions, protein-lipid interactions, and protein-polynucleotide interactions.

Kinases regulate many different cell processes including, but not limited to, proliferation, differentiation, apoptosis, motility, transcription, translation and other signaling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signaling pathways to activate or inactivate (either directly or indirectly), for example, a metabolic enzyme, regulatory protein, receptor, cytoskeletal protein, ion channel or pump, or transcription factor. Uncontrolled signaling due to defective control of protein phosphorylation has been implicated in a number of diseases, including, for example, inflammation, cancer, allergy/asthma, disease and conditions of the immune system, disease and conditions of the central nervous system, and angiogenesis.

Initial interest in protein kinases as pharmacological targets was stimulated by the findings that many viral oncogenes encode structurally modified cellular protein kinases with constitutive enzyme activity. These findings pointed to the potential involvement of proto-oncogene encoded protein kinases in human proliferative disorders. Subsequently, deregulated protein kinase activity, resulting from a variety of more subtle mechanisms, has been implicated in the pathophysiology of a number of important human disorders including cancer and immunologically related diseases. The development of selective protein kinase inhibitors that can block the disease pathologies and/or symptoms resulting from aberrant protein kinase activity has therefore generated much interest.

SUMMARY OF THE INVENTION

The invention relates to compounds of the formula:

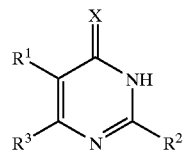

wherein,
R$^1$ is H; CN; COOR$^5$; C(O)NR$^5$R$^5$; halo; C1–C10 alkyl; C1–C10 alkenyl; C1–C10 alkyl substituted with 1–3 independent NR$^5$R$^5$, NR$^5$R$^6$, SR$^5$ or OR$^5$; or C1–C10 alkenyl substituted with 1–3 independent NR$^5$R$^5$, NR$^5$R$^6$, SR$^5$ or OR$^5$;

R$^2$ is NR$^5$R$^5$; SR$^5$; OR$^5$; R$^8$; aryl; N(R$^5$)—N=CH(R$^8$); N(R$^5$)—N=CH(aryl); NR$^5$—NR$^5$C(O)NR$^5$R$^5$; NR$^5$—

$NR^5R^{15}$; $NR^5$—$NR^5R^6$; C1–C10 alkyl substituted with 1–3 independent aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)NR^5R^5$, or $S(O)_2NR^5R^5$; or C1–C10 alkenyl substituted with 1–3 independent aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)NR^5R^5$, or $S(O)_2NR^5R^5$;

$R^3$ is phenyl substituted with 1–3 independent $R^4$; $R^8$; $COOR^5$; or C1–C10 alkyl substituted with 1–3 independent aryl, $R^7$ or $R^8$;

X is O or S; and the remaining groups are as defined herein.

The invention also relates to compositions comprising these compounds, methods of making these compounds, methods of inhibiting enzyme activity, particularly kinase activity, through use of these compounds, and methods of treating disease or disease symptoms in a mammal, particularly where modulation of enzyme activity, and more particularly kinase activity, can affect disease outcome.

DETAILED DESCRIPTION OF THE INVENTION

The invention provides compounds useful in inhibiting kinase activity and inhibiting kinases or other polypeptides having sequences or subsequences homologous to kinase sequences or subsequences. In one embodiment, the inhibitory compound has the formula:

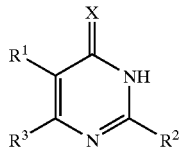

wherein, $R^1$ is H; CN; $COOR^5$; $C(O)NR^5R^5$; halo; C1–C10 alkyl; C1–C10 alkenyl; C1–C10 alkyl substituted with 1–3 independent $NR^5R^5$, $NR^5R^6$, $SR^5$ or $OR^5$; or C1–C10 alkenyl substituted with 1–3 independent $NR^5R^5$, $NR^5R^6$, $SR^5$ or $OR^5$;

$R^2$ is $NR^5R^5$; $SR^5$; $OR^5$; $R^8$; aryl; $N(R^5)$—N=CH($R^8$); $N(R^5)$—N=CH(aryl); $NR^5$—$NR^5C(O)NR^5R^5$; $NR^5$—$NR^5R^{15}$; $NR^5$—$NR^5R^6$; C1–C10 alkyl substituted with 1–3 independent aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)NR^5R^5$, or $S(O)_2NR^5R^5$; or C1–C10 alkenyl substituted with 1–3 independent aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)NR^5R^5$, or $S(O)_2NR^5R^5$;

$R^3$ is phenyl substituted with 1–3 independent $R^4$; $R^8$; $COOR^5$; or C1–C10 alkyl substituted with 1–3 independent aryl, $R^7$ or $R^8$;

X is O or S; and

Each $R^4$ is independently selected from H, C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $SR^5$; $OR^5$; $NR^5R^5$; $NR^5R^6$; $COOR^5$; $NO_2$; CN; C(O)$R^5$; $C(O)C(O)R^5$; $C(O)NR^5R^5$; $OC(O)R^5$; $S(O)_2R^5$; $S(O)_2NR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; $NR^5C(O)C(O)NR^5R^6$; C1–C10 alkyl substituted with aryl, $R^7$ or $R^8$; or C1–C10 alkenyl substituted with aryl, $R^7$ or $R^8$;

Each $R^5$ is independently H; C1–C10 alkyl; C2–C10 alkenyl; C2–C10 alkynyl; C3–C10 cycloalkyl; C4–C10 cycloalkenyl; aryl; $R^9$; C1–C10 alkyl substituted with 1–3 independent aryl, $R^7$ or $R^9$ groups; C3–C10 cycloalkyl substituted with 1–3 independent aryl, $R^7$ or $R^9$ groups; or C1–C10 alkenyl substituted with 1–3 independent aryl, $R^7$ or $R^9$;

Each $R^6$ is independently $C(O)R^5$, $COOR^5$, or $S(O)_2 R^5$;

Each $R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, or $C(O)NR^{10}R^{10}$;

Each $R^8$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; aryl; $R^9$; halo; sulfur; oxygen; $CF_3$; haloalkyl; $SR^5$; $OR^5$; $OC(O)R^5$; $NR^5R^5$; $NR^5R^6$; $NR^6R^6$; $COOR^5$; $NO_2$; CN; $C(O)R^5$; $C(O)NR^5R^5$; C1–C10 alkyl substituted with 1–3 independent $R^7$, $R^9$ or aryl; or C1–C10 alkenyl substituted with 1–3 independent $R^7$, $R^9$ or aryl;

Each $R^9$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; halo; sulfur; oxygen; $CF_3$; haloalkyl; $SR^{10}$; $OR^{10}$; $NR^{10}R^{10}$; $NR^{10}R^{11}$; $NR^{11}R^{11}$; $COOR^{10}$; $NO_2$; CN; $C(O)R^{10}$; or $C(O)NR^{10}R^{10}$;

Each $R^{10}$ is independently H, C1–C10 alkyl; C2–C10 alkenyl; C2–C10 alkynyl; C3–C10 cycloalkyl; C4–C10 cycloalkenyl; haloalkyl; C1–C10 alkyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$; or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$;

Each $R^{11}$ is independently $C(O)R^{10}$, $COOR^{10}$, or $S(O)_2 R^{10}$;

Each $R^{12}$ is independently H, C1–C10 alkyl, C2–C10 alkenyl, C2–C10 alkynyl, C3–C10 cycloalkyl, C4–C10 cycloalkenyl, or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$;

Each $R^{13}$ is independently H; C1–C10 alkyl; C2–C10 alkenyl; C2–C10 alkynyl; C3–C10 cycloalkyl; C4–C10 cycloalkenyl; C1–C10 alkyl optionally substituted with halo, $CF_3$, $OR^{19}$, $SR^{19}$, $NR^{19}R^{19}$, $COOR^{19}$, $NO_2$, CN; or phenyl optionally substituted with halo, $CF_3$, $OR^{19}$, $SR^{19}$, $NR^{19}R^{19}$, $COOR^{19}$, $NO_2$, CN;

Each $R^{15}$ is independently C1–C10 alkyl; C2–C10 alkenyl; C2–C10 alkynyl; C3–C10 cycloalkyl; C4–C10 cycloalkenyl; aryl; $R^9$; C1–C10 alkyl substituted with 1–3 independent aryl, $R^7$ or $R^9$ groups; or C1–C10 alkenyl substituted with 1–3 independent aryl, $R^7$ or $R^9$;

Each $R^{16}$ is independently C1–C10 alkyl; C2–C10 alkenyl; C2–C10 alkynyl; C3–C10 cycloalkyl; C4–C10 cycloalkenyl; $R^9$; C1–C10 alkyl substituted with 1–3 independent aryl, $R^7$ or $R^9$ groups; C1–C10 alkenyl substituted with 1–3 independent aryl, $R^7$ or $R^9$; or phenyl substituted with 1–3 independent C1–C10 alkyl, C2–C10 alkenyl, C2–C10 alkynyl, C3–C10 cycloalkyl, C4–C10 cycloalkenyl, $R^9$, halo, $CF_3$, $OR^{12}$, $SR^{12}$; $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$, C1–C10 alkyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$;

Each $R^{19}$ is independently H; C1–C10 alkyl; C3–C10 cycloalkyl or phenyl;

Each haloalkyl is independently a C1–C10 alkyl substituted with one or more halogen atoms, selected from F, Cl, Br, or I, wherein the number of halogen atoms may not exceed that number that results in a perhaloalkyl group; and Each aryl is independently a 6-carbon monocyclic or 10-carbon bicyclic aromatic ring system optionally substituted with 1–3 independent C1–C10 alkyl; C2–C10 alkenyl; C2–C10 alkynyl; C3–C10 cycloalkyl; C4–C10 cycloalkenyl; $R^9$; halo; haloalkyl; $CF_3$; $OR^{12}$; $SR^{12}$; $NR^{12}R^{12}$; $COOR^{12}$; $NO_2$; CN; $C(O)R^{12}$; $C(O)C(O)R^{12}$; $C(O)NR^{12}R^{12}$; $S(O)_2R^{12}$; $N(R^{12})C(O)R^{12}$; $N(R^{12})(COOR^{12})$; $N(R^{12})S(O)_2R^{12}$; $S(O)_2NR^{12}R^{12}$; $OC(O)R^{12}$; $NR^{12}C(O)NR^{12}R^{12}$; $NR^{12}C(O)C(O)R^{12}$; $NR^{12}C(O)R^9$; $NR^{12}S(O)_2NR^{12}R^{12}$; $NR^{12}S(O)_2R^9$; $NR^{12}C(O)C(O)NR^{12}R^{12}$; C1–C10 alkyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$; C2–C10 alkenyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$; or $R^{12}$.

Preferred compounds include those of the formula above wherein X is O.

In another embodiment, the compounds of the formula above are those wherein, $R^1$ is H; $COOR^5$; $C(O)NR^5R^5$; halo; C2–C10 alkyl; C1–C10 alkenyl; C1–C10 alkyl substituted with $NR^5R^5$, $NR^5R^6$, $SR^5$ or $OR^5$; or C1–C10 alkenyl substituted with $NR^5R^5$, $NR^5R^6$, $SR^5$ or $OR^5$;

$R^2$ is $NR^5R^{15}$; $SR^5$; $OR^5$; $R^8$; aryl; $N(R^5)-N=CH(R^8)$; $N(R^5)-N=CH(aryl)$; $NR^5-NR^5C(O)NR^5R^5$; $NR^5-NR^5R^{16}$; $NR^5-NR^5R^6$; C1–C10 alkyl substituted with aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)NR^5R^5$, or $S(O)_2NR^5R^5$; or C1–C10 alkenyl substituted with aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)NR^5R^5$, or $S(O)_2NR^5R^5$;

$R^3$ is phenyl substituted with 1–3 independent $R^4$; $R^8$; $COOR^5$; or C1–C10 alkyl substituted with aryl, $R^7$ or $R^8$;

X is O or S;

Each $R^4$ is independently selected from H, C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $SR^5$; $OR^5$; $NR^5R^5$; $NR^5R^6$; $COOR^5$; $NO_2$; CN; $C(O)R^5$; $C(O)C(O)R^5$; $C(O)NR^5R^5$; $OC(O)R^5$; $S(O)_2R^5$; $S(O)_2NR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; $NR^5C(O)C(O)NR^5R^6$; C1–C10 alkyl substituted with aryl, $R^7$ or $R^8$; or C1–C10 alkenyl substituted with aryl, $R^7$ or $R^8$;

Each $R^5$ is independently H; C1–C10 alkyl; C2–C10 alkenyl; C2–C10 alkynyl; C3–C10 cycloalkyl; C4–C10 cycloalkenyl; aryl; $R^9$; C1–C10 alkyl substituted with one or two independent aryl, $R^7$ or $R^9$ groups; C3–C10 cycloalkyl substituted with one or two independent aryl, $R^7$ or $R^9$ groups; or C1–C10 alkenyl substituted with aryl, $R^7$ or $R^9$;

Each $R^6$ is independently $C(O)R^5$, $COOR^5$, or $S(O)_2R^5$;

Each $R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, or $C(O)NR^{10}R^{10}$;

Each $R^8$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; aryl; $R^9$; halo; sulfur; oxygen; $CF_3$; haloalkyl; $SR^5$; $OR^5$; $OC(O)R^5$; $NR^5R^5$; $NR^5R^6$; $NR^6R^6$; $COOR^5$; $NO_2$; CN; $C(O)R^5$; $C(O)NR^5R^5$; C1–C10 alkyl substituted with $R^7$, $R^9$ or aryl; C1–C10 alkenyl substituted with $R^7$, $R^9$ or aryl;

Each $R^9$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; halo; sulfur; oxygen; $CF_3$; haloalkyl; $SR^{10}$; $OR^{10}$; $NR^{10}R^{10}$; $NR^{10}R^{11}$; $NR^{11}R^{11}$; $COOR^{10}$; $NO_2$; CN; $C(O)R^{10}$; or $C(O)NR^{10}R^{10}$;

Each $R^{10}$ is independently H, C1–C10 alkyl; C2–C10 alkenyl; C2–C10 alkynyl; C3–C10 cycloalkyl; C4–C10 cycloalkenyl; haloalkyl; C1–C10 alkyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$; or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$;

Each $R^{11}$ is independently $C(O)R^{10}$, $COOR^{10}$, or $S(O)_2R^{10}$;

Each $R^{12}$ is independently H, C1–C10 alkyl, C2–C10 alkenyl, C2–C10 alkynyl, C3–C10 cycloalkyl, C4–C10 cycloalkenyl, or phenyl optionally substituted with 1–3 independent C1–C10 alkyl, C2–C10 alkenyl, C2–C10 alkynyl, C3–C10 cycloalkyl, C4–C10 cycloalkenyl, halo, CF$_3$, OR$^{13}$, SR$^{13}$, NR$^{13}$R$^{13}$, COOR$^{13}$, NO$_2$, CN, C(O)R$^{13}$, C(O)NR$^{13}$R$^{13}$, NHC(O)R$^{13}$, or OC(O)R$^{13}$;

Each R$^{13}$ is independently H; C1–C10 alkyl; C2–C10 alkenyl; C2–C10 alkynyl; C3–C10 cycloalkyl; C4–C10 cycloalkenyl; C1–C10 alkyl optionally substituted with halo, CF$_3$, OR$^{19}$, SR$^{19}$, NR$^{19}$R$^{19}$, COOR$^{19}$, NO$_2$, CN; or phenyl optionally substituted with halo, CF$_3$, OR$^{19}$, SR$^{19}$, NR$^{19}$R$^{19}$, COOR$^{19}$, NO$_2$, CN;

Each R$^{15}$ is independently C1–C10 alkyl; C2–C10 alkenyl; C2–C10 alkynyl; C3–C10 cycloalkyl; C4–C10 cycloalkenyl; aryl; R$^9$; C1–C10 alkyl substituted with one or two independent aryl, R$^7$ or R$^9$ groups; or C1–C10 alkenyl substituted with aryl, R$^7$ or R$^9$;

Each R$^{16}$ is independently C1–C10 alkyl; C2–C10 alkenyl; C2–C10 alkynyl; C3–C10 cycloalkyl; C4–C10 cycloalkenyl; R$^9$; C1–C10 alkyl substituted with one or two independent aryl, R$^7$ or R$^9$ groups; C1–C10 alkenyl substituted with aryl, R$^7$ or R$^9$; or phenyl substituted with 1–3 independent C1–C10 alkyl, C2–C10 alkenyl, C2–C10 alkynyl, C3–C10 cycloalkyl, C4–C10 cycloalkenyl, R$^9$, halo, CF$_3$, OR$^{12}$, SR$^{12}$, NR$^{12}$R$^{12}$, COOR$^{12}$, NO$_2$, CN, C(O)R$^{12}$, C(O)NR$^{12}$R$^{12}$, NHC(O)R$^{12}$, NH(COOR$^{12}$), S(O)$_2$NR$^{12}$R$^{12}$, OC(O)R$^{12}$, C1–C10 alkyl substituted with R$^9$, halo, CF$_3$, OR$^{12}$, SR$^{12}$, NR$^{12}$R$^{12}$, COOR$^{12}$, NO$_2$, CN, C(O)R$^{12}$, C(O)NR$^{12}$R$^{12}$, NHC(O)R$^{12}$, NH(COOR$^{12}$), S(O)$_2$NR$^{12}$R$^{12}$, OC(O)R$^{12}$;

Each R$^{19}$ is independently H; C1–C10 alkyl; C3–C10 cycloalkyl or phenyl;

Each haloalkyl is independently a C1–C10 alkyl substituted with one or more halogen atoms, selected from F, Cl, Br, or I, wherein the number of halogen atoms may not exceed that number that results in a perhaloalkyl group;

Each aryl is independently a 6-carbon monocyclic or 10-carbon bicyclic aromatic ring system optionally substituted with 1–3 independent C1–C10 alkyl; C2–C10 alkenyl; C2–C10 alkynyl; C3–C10 cycloalkyl; C4–C10 cycloalkenyl; R$^9$; halo; haloalkyl; CF$_3$; OR$^{12}$; SR$^{12}$; NR$^{12}$R$^{12}$; COOR$^{12}$; NO$_2$; CN; C(O)R$^{12}$; C(O)C(O)R$^{12}$; C(O)NR$^{12}$R$^{12}$; S(O)$_2$R$^{12}$; N(R$^{12}$)C(O)R$^{12}$; N(R$^{12}$)(COOR$^{12}$); N(R$^{12}$)S(O)$_2$R$^{12}$; S(O)$_2$NR$^{12}$R$^{12}$; OC(O)R$^{12}$; NR$^{12}$C(O)NR$^{12}$R$^{12}$; NR$^{12}$C(O)C(O)R$^{12}$; NR$^{12}$C(O)R$^9$; NR$^{12}$S(O)$_2$NR$^{12}$R$^{12}$; NR$^{12}$S(O)$_2$R$^9$; NR$^{12}$C(O)C(O)NR$^{12}$R$^{12}$; C1–C10 alkyl substituted with 1–3 independent R$^9$, halo, CF$_3$, OR$^{12}$, SR$^{12}$, NR$^{12}$R$^{12}$, COOR$^{12}$, NO$_2$, CN, C(O)R$^{12}$, C(O)NR$^{12}$R$^{12}$, NHC(O)R$^{12}$, NH(COOR$^{12}$), S(O)$_2$NR$^{12}$R$^{12}$, OC(O)R$^{12}$; C2–C10 alkenyl substituted with 1–3 independent R$^9$, halo, CF$_3$, OR$^{12}$, SR$^{12}$, NR$^{12}$R$^{12}$, COOR$^{12}$, NO$_2$, CN, C(O)R$^{12}$, C(O)NR$^{12}$R$^{12}$, NHC(O)R$^{12}$, NH(COOR$^{12}$), S(O)$_2$NR$^{12}$R$^{12}$, OC(O)R$^{12}$; or R$^{12}$. Preferred compounds of this embodiment are also those wherein X is O.

In another embodiment, the invention relates to a compound of the formula,

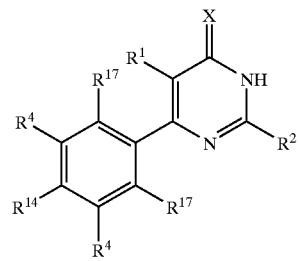

wherein,
R$^1$ is CN;
R$^2$ is NR$^5$R$^{15}$; OR$^5$; R$^8$; aryl; N(R$^5$)—N=CH(R$^8$); N(R$^5$)—N=CH(aryl); NR$^5$—NR$^5$C(O)NR$^5$R$^5$ ; NR$^5$—R$^{16}$; NR$^5$—NR$^5$R$^6$; C1–C10 alkyl substituted with aryl, R$^8$, halo, CF$_3$, SR$^5$, OR$^5$, OC(O)R$^5$, NR$^5$R$^5$, NR$^5$R$^6$, COOR$^5$, NO$_2$, CN, C(O)R$^5$, C(O)NR$^5$R$^5$, or S(O)$_2$NR$^5$R$^5$; or C1–C10 alkenyl substituted with aryl, R$^8$, halo, CF$_3$, SR$^5$, OR$^5$, OC(O)R$^5$, NR$^5$R$^5$, NR$^5$R$^6$, COOR$^5$, NO$_2$, CN, C(O)R$^5$, C(O)NR$^5$R$^5$, or S(O)$_2$NR$^5$R$^5$;

X is O or S;

Each R$^4$ is independently selected from H, C1–C10 alkyl; C2–C10 alkenyl; C2–C10 alkynyl; C3–C10 cycloalkyl; C4–C10 cycloalkenyl; aryl; R$^8$; halo; haloalkyl; CF$_3$; SR$^5$; OR$^5$; NR$^5$R$^5$; NR$^5$R$^6$; COOR$^5$; NO$_2$; CN; C(O)R$^5$; C(O)C(O)R$^5$; C(O)NR$^5$R$^5$; OC(O)R$^5$; S(O)$_2$R$^5$; S(O)$_2$NR$^5$R$^5$; NR$^5$C(O)NR$^5$R$^5$; NR$^5$C(O)C(O)R$^5$; NR$^5$C(O)R$^5$; NR$^5$(COOR$^5$); NR$^5$C(O)R$^8$; NR$^5$S(O)$_2$NR$^5$R$^5$; NR$^5$S(O)$_2$R$^5$; NR$^5$S(O)$_2$R$^8$; NR$^5$C(O)C(O) NR$^5$R$^5$; NR$^5$C(O)C(O)NR$^5$R$^6$; C1–C10 alkyl substituted with aryl, R$^7$ or R$^8$; or C1–C10 alkenyl substituted with aryl, R$^7$ or R$^8$;

Each R$^5$ is independently H; C1–C10 alkyl; C2–C10 alkenyl; C2–C10 alkynyl; C3–C10 cycloalkyl; C4–C10 cycloalkenyl; aryl; R$^9$; C1–C10 alkyl substituted with one or two independent aryl, R$^7$ or R$^9$ groups; C3–C10 cycloalkyl substituted with one or two independent aryl, R$^7$ or R$^9$ groups; or C1–C10 alkenyl substituted with aryl, R$^7$ or R$^9$;

Each R$^6$ is independently C(O)R$^5$, COOR$^5$, or S(O)$_2$R$^5$;

Each R$^7$ is independently halo, CF$_3$, SR$^{10}$, OR$^{10}$, OC(O) R$^{10}$, NR$^{10}$R$^{10}$, NR$^{10}$R$^{11}$, NR$^{11}$R$^{11}$, COOR$^{10}$, NO$_2$, CN, C(O)R$^{10}$, or C(O)NR$^{10}$R$^{10}$;

Each R$^8$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; aryl; R$^9$; halo; sulfur; oxygen; CF$_3$; haloalkyl; SR$^5$; OR$^5$; OC(O)R$^5$; NR$^5$R$^5$; NR$^5$R$^6$; NR$^6$R$^6$; COOR$^5$; NO$_2$; CN; C(O)R$^5$; C(O)NR$^5$R$^5$; C1–C10 alkyl substituted with R$^7$, R$^9$ or aryl; C1–C10 alkenyl substituted with R$^7$, R$^9$ or aryl;

Each R$^9$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; halo; sulfur; oxygen; $CF_3$; haloalkyl; $SR^{10}$; $OR^{10}$; $NR^{10}R^{10}$; $NR^{10}R^{11}$; $NR^{11}R^{11}$; $COOR^{10}$; $NO_2$; CN; $C(O)R^{10}$; or $C(O)NR^{10}R^{10}$;

Each $R^{10}$ is independently H, C1–C10 alkyl; C2–C10 alkenyl; C2–C10 alkynyl; C3–C10 cycloalkyl; C4–C10 cycloalkenyl; haloalkyl; C1–C10 alkyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$; or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$;

Each $R^{11}$ is independently $C(O)R^{10}$, $COOR^{10}$, or $S(O)_2R^{10}$;

Each $R^{12}$ is independently H, C1–C10 alkyl, C2–C10 alkenyl, C2–C10 alkynyl, C3–C10 cycloalkyl, C4–C10 cycloalkenyl, or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$;

Each $R^{13}$ is independently H; C1–C10 alkyl; C2–C10 alkenyl; C2–C10 alkynyl; C3–C10 cycloalkyl; C4–C10 cycloalkenyl; C1–C10 alkyl optionally substituted with halo, $CF_3$, $OR^{19}$, $SR^{19}$, $NR^{19}R^{19}$, $COOR^{19}$, $NO_2$, CN; or phenyl optionally substituted with halo, $CF_3$, $OR^{19}$, $SR^{19}$, $NR^{19}R^{19}$, $COOR^{19}$, $NO_2$, CN;

Each $R^{14}$ is each independently selected from C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $SR^5$; $OR^5$; $NR^5R^5$; $NR^5R^6$; $COOR^5$; $NO_2$; CN; $C(O)R^5$; $C(O)C(O)R^5$; $C(O)NR^5R^5$; $OC(O)R^5$; $S(O)_2R^5$; $S(O)_2NR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; $NR^5C(O)C(O)NR^5R^6$; C1–C10 alkyl substituted with aryl, $R^7$ or $R^8$; or C1–C10 alkenyl substituted with aryl, $R^7$ or $R^8$;

Each $R^{15}$ is independently C1–C10 alkyl; C2–C10 alkenyl; C2–C10 alkynyl; C3–C10 cycloalkyl; C4–C10 cycloalkenyl; aryl; $R^9$; C1–C10 alkyl substituted with one or two independent aryl, $R^7$ or $R^9$ groups; or C1–C10 alkenyl substituted with aryl, $R^7$ or $R^9$;

Each $R^{16}$ is independently C1–C10 alkyl; C2–C10 alkenyl; C2–C10 alkynyl; C3–C10 cycloalkyl; C4–C10 cycloalkenyl; $R^9$; C1–C10 alkyl substituted with one or two independent aryl, $R^7$ or $R^9$ groups; C1–C10 alkenyl substituted with aryl, $R^7$ or $R^9$; or phenyl substituted with 1–3 independent C1–C10 alkyl, C2–C10 alkenyl, C2–C10 alkynyl, C3–C10 cycloalkyl, C4–C10 cycloalkenyl, $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$, C1–C10 alkyl substituted with $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$;

Each R17 is independently selected from H, C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $SR^5$; $OR^5$; $NR^5R^5$; $NR^5R^6$; $COOR^5$; $NO_2$; CN; $C(O)R^5$; $C(O)C(O)R^5$; $C(O)NR^5R^5$; $OC(O)R^5$; $S(O)_2R^5$; $S(O)_2NR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; $NR^5C(O)C(O)NR^5R^6$; C1–C10 alkyl substituted with aryl, $R^7$ or $R^8$; or C1–C10 alkenyl substituted with aryl, $R^7$ or $R^8$;

Each $R^{19}$ is independently H; C1–C10 alkyl; C3–C10 cycloalkyl or phenyl;

Each haloalkyl is independently a C1–C10 alkyl substituted with one or more halogen atoms, selected from F, Cl, Br, or I, wherein the number of halogen atoms may not exceed that number that results in a perhaloalkyl group;

Each aryl is independently a 6-carbon monocyclic or 10-carbon bicyclic aromatic ring system optionally substituted with 1–3 independent C1–C10 alkyl; C2–C10 alkenyl; C2–C10 alkynyl; C3–C10 cycloalkyl; C4–C10 cycloalkenyl; $R^9$; halo; haloalkyl; $CF_3$; $OR^{12}$; $SR^{12}$; $NR^{12}R^{12}$; $COOR^{12}$; $NO_2$; CN; $C(O)R^{12}$; $C(O)C(O)R^{12}$; $C(O)NR^{12}R^{12}$; $S(O)_2R^{12}$; $N(R^{12})C(O)R^{12}$; $N(R^{12})(COOR^{12})$; $N(R^{12})S(O)_2R^{12}$; $S(O)_2NR^{12}R^{12}$; $OC(O)R^{12}$; $NR^{12}C(O)NR^{12}R^{12}$; $NR^{12}C(O)C(O)R^{12}$; $NR^{12}C(O)R^9$; $NR^{12}S(O)_2NR^{12}R^{12}$; $NR^{12}S(O)_2R^9$; $NR^{12}C(O)C(O)NR^{12}R^{12}$; C1–C10 alkyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$; C2–C10 alkenyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$; or $R^{12}$;

wherein when all $R^4$ and $R^{17}$ are simultaneously H, $R^{14}$ may not be Me, Cl, OMe or $NO_2$; and wherein $R^{14}$ and $R^{17}$ may not simultaneously be Cl. Preferred compounds of this embodiment are also those wherein X is O. Alternatively, the compound has the formula directly above wherein each $R^{14}$ is independently selected from C2–C10 alkyl; C2–C10 alkenyl; C2–C10 alkynyl; C3–C10 cycloalkyl; C4–C10 cycloalkenyl; aryl; $R^8$; I; Br; F; $CF_3$; $SR^5$; $OR^{25}$; $NR^5R^5$; $NR^5R^6$; $COOR^5$; CN; $C(O)R^5$; $C(O)C(O)R^5$; $C(O)NR^5R^5$; $S(O)_2NR^5R^5$; $NR^5C(O)NR^5R^5$; $NR^5C(O)C(O)R^5$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; $NR^5C(O)C(O)NR^5R^6$; C1–C10 alkyl substituted with aryl, $R^7$ or $R^8$; or C1–C10 alkenyl substituted with aryl, $R^7$ or $R^8$; and each $R^{25}$ is independently H; C2–C10 alkyl; C2–C10 alkenyl; C2–C10 alkynyl; C3–C10 cycloalkyl; C4–C10 cycloalkenyl; aryl; $R^9$; C1–C10 alkyl substituted with one or two independent aryl, $R^7$ or $R^9$ groups; C3–C10 cycloalkyl substituted with one or two independent aryl, $R^7$ or $R^9$ groups; or C1–C10 alkenyl substituted with aryl, $R^7$ or $R^9$;. Alternatively, the compound has the formula directly above wherein each $R^{14}$ is independently selected from $NR^5R^5$; $NR^5R^6$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; or $NR^5C(O)C(O)NR^5R^6$. In alternate embodiments, the compound is of any of the formulae above, wherein at least two of $R^4$ and/or $R^{17}$ are independently H. Preferred compounds of these embodiments are also those wherein X is O.

In an alternate embodiment, the inhibitory compound has the formula:

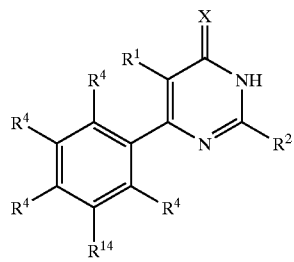

wherein, $R^1$ is CN;

$R^2$ is $NR^5R^{15}$; $OR^5$; $R^8$; aryl; $N(R^5)$—$N$=$CH(R^8)$; $N(R^5)$—$N$=$CH(aryl)$; $NR^5$—$NR^5C(O)NR^5R^5$; $NR^5$—$NR^5R^{16}$; $NR^5$—$NR^5R^6$; C1–C10 alkyl substituted with aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)NR^5R^5$, or $S(O)_2NR^5R^5$; or C1–C10 alkenyl substituted with aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)NR^5R^5$, or $S(O)_2NR^5R^5$;

X is O or S;

Each $R^4$ is independently selected from H, C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $SR^5$; $OR^5$; $NR^5R^5$; $NR^5R^6$; $COOR^5$; $NO_2$; CN; $C(O)R^5$; $C(O)C(O)R^5$; $C(O)NR^5R^5$; $OC(O)R^5$; $S(O)_2R^5$; $S(O)_2NR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; $NR^5C(O)C(O)NR^5R^6$; C1–C10 alkyl substituted with aryl, $R^7$ or $R^8$; or C1–C10 alkenyl substituted with aryl, $R^7$ or $R^8$;

Each $R^5$ is independently H; C1–C10 alkyl; C2–C10 alkenyl; C2–C10 alkynyl; C3–C10 cycloalkyl; C4–C10 cycloalkenyl; aryl; $R^9$; C1–C10 alkyl substituted with one or two independent aryl, $R^7$ or $R^9$ groups; C3–C10 cycloalkyl substituted with one or two independent aryl, $R^7$ or $R^9$ groups; or C1–C10 alkenyl substituted with aryl, $R^7$ or $R^9$;

Each $R^6$ is independently $C(O)R^5$, $COOR^5$, or $S(O)_2 R^5$;

Each $R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, or $C(O)NR^{10}R^{10}$;

Each $R^8$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; aryl; $R^9$; halo; sulfur; oxygen; $CF_3$; haloalkyl; $SR^5$; $OR^5$; $OC(O)R^5$; $NR^5R^5$; $NR^5R^6$; $NR^6R^6$; $COOR^5$; $NO_2$; CN; $C(O)R^5$; $C(O)NR^5R^5$; C1–C10 alkyl substituted with $R^7$, $R^9$ or aryl; C1–C10 alkenyl substituted with $R^7$, $R^9$ or aryl;

Each $R^9$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; halo; sulfur; oxygen; $CF_3$; haloalkyl; $SR^{10}$; $OR^{10}$; $NR^{10}R^{10}$; $NR^{10}R^{11}$; $NR^{11}R^{11}$; $COOR^{10}$; $NO_2$; CN; $C(O)R^{10}$; or $C(O)NR^{10}R^{10}$;

Each $R^{10}$ is independently H, C1–C10 alkyl; C2–C10 alkenyl; C2–C10 alkynyl; C3–C10 cycloalkyl; C4–C10 cycloalkenyl; haloalkyl; C1–C10 alkyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$; or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$;

Each $R^{11}$ is independently $C(O)R^{10}$, $COOR^{10}$, or $S(O)_2 R^{10}$;

Each $R^{12}$ is independently H, C1–C10 alkyl, C2–C10 alkenyl, C2–C10 alkynyl, C3–C10 cycloalkyl, C4–C10 cycloalkenyl, or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$;

Each $R^{13}$ is independently H; C1–C10 alkyl; C2–C10 alkenyl; C2–C10 alkynyl; C3–C10 cycloalkyl; C4–C10 cycloalkenyl; C1–C10 alkyl optionally substituted with halo, $CF_3$, $OR^{19}$, $SR^{19}$, $NR^{19}R^{19}$, $COOR^{19}$, $NO_2$, CN; or phenyl optionally substituted with halo, $CF_3$, $OR^{19}$, $SR^{19}$, $NR^{19}R^{19}$, $COOR^{19}$, $NO_2$, CN;

Each $R^{14}$ is independently selected from C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $SR^5$; $OR^5$; $NR^5R^5$; $NR^5R^6$; $COOR^5$; $NO_2$; CN; $C(O)R^5$; $C(O)C(O)R^5$; $C(O)NR^5R^5$; $OC(O)R^5$; $S(O)_2R^5$; $S(O)_2NR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; $NR^5C(O)C(O)NR^5R^6$; C1–C10 alkyl substituted with aryl, $R^7$ or $R^8$; or C1–C10 alkenyl substituted with aryl, $R^7$ or $R^8$;

Each $R^{15}$ is independently C1–C10 alkyl; C2–C10 alkenyl; C2–C10 alkynyl; C3–C10 cycloalkyl; C4–C10 cycloalkenyl; aryl; $R^9$; C1–C10 alkyl substituted with one or two independent aryl, $R^7$ or $R^9$ groups; or C1–C10 alkenyl substituted with aryl, $R^7$ or $R^9$;

Each $R^{16}$ is independently C1–C10 alkyl; C2–C10 alkenyl; C2–C10 alkynyl; C3–C10 cycloalkyl; C4–C10 cycloalkenyl; $R^9$; C1–C10 alkyl substituted with one or two independent aryl, $R^7$ or $R^9$ groups; C1–C10 alkenyl substituted with aryl, $R^7$ or $R^9$; or phenyl substituted with 1–3 independent C1–C10 alkyl, C2–C10 alkenyl, C2–C10 alkynyl, C3–C10 cycloalkyl, C4–C10 cycloalkenyl, $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$, C1–C10 alkyl substituted with $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$;

Each $R^{19}$ is independently H; C1–C10 alkyl; C3–C10 cycloalkyl or phenyl;

Each haloalkyl is independently a C1–C10 alkyl substituted with one or more halogen atoms, selected from F, Cl, Br, or I, wherein the number of halogen atoms may not exceed that number that results in a perhaloalkyl group;

Each aryl is independently a 6-carbon monocyclic or 10-carbon bicyclic aromatic ring system optionally substituted with 1–3 independent C1–C10 alkyl; C2–C10 alkenyl; C2–C10 alkynyl; C3–C10 cycloalkyl; C4–C10 cycloalkenyl; $R^9$; halo; haloalkyl; $CF_3$; $OR^{12}$; $SR^{12}$; $NR^{12}R^{12}$; $COOR^{12}$; $NO_2$; CN; $C(O)R^{12}$; $C(O)C(O)R^{12}$; $C(O)NR^{12}R^{12}$; $S(O)_2R^{12}$; $N(R^{12})C(O)R^{12}$; $N(R^{12})(COOR^{12})$; $N(R^{12})S(O)_2R^{12}$; $S(O)_2NR^{12}R^{12}$; $OC(O)R^{12}$; $NR^{12}C(O)NR^{12}R^{12}$; $NR^{12}C(O)C(O)R^{12}$; $NR^{12}C(O)R^9$; $NR^{12}S(O)_2NR^{12}R^{12}$; $NR^{12}S(O)_2R^9$; $NR^{12}C(O)C(O)NR^{12}R^{12}$; C1–C10 alkyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$; C2–C10 alkenyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$; or $R^{12}$;

wherein when all $R^4$ are H, $R^{14}$ may not be Me or OMe. Preferred compounds of this embodiment are also those wherein X is O. Alternatively, the compound has the formula directly above wherein each $R^{14}$ is independently selected from C2–C10 alkyl; C2–C10 alkenyl; C2–C10 alkynyl; C3–C10 cycloalkyl; C4–C10 cycloalkenyl; aryl; $R^8$; halo; $CF_3$; $SR^5$; $OR^{25}$; $NR^5R^5$; $NR^5R^6$; $COOR^5$; $NO_2$; CN; $C(O)R^5$; $C(O)C(O)R^5$; $C(O)NR^5R^5$; $S(O)_2NR^5R^5$; $NR^5C(O)NR^5R^5$; $NR^5C(O)C(O)R^5$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; $NR^5C(O)C(O)NR^5R^6$; C1–C10 alkyl substituted with aryl, $R^7$ or $R^8$; or C1–C10 alkenyl substituted with aryl, $R^7$ or $R^8$; and each $R^{25}$ is independently H; C2–C10 alkyl; C2–C10 alkenyl; C2–C10 alkynyl; C3–C10 cycloalkyl; C4–C10 cycloalkenyl; aryl; $R^9$; C1–C10 alkyl substituted with one or two independent aryl, $R^7$ or $R^9$ groups; C3–C10 cycloalkyl substituted with one or two independent aryl, $R^7$ or $R^9$ groups; or C1–C10 alkenyl substituted with aryl, $R^7$ or $R^9$. Alternatively, the compound has the formula directly above wherein each $R^{14}$ is independently selected from $NR^5R^5$; $NR^5R^6$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; or $NR^5C(O)C(O)NR^5R^6$. In alternate embodiments, the compound is of any of the formulae above, wherein at least two of the $R^4$ are independently H. Preferred compounds of these embodiments are also those wherein X is O.

In an alternate embodiment, the inhibitory compound has the formula,

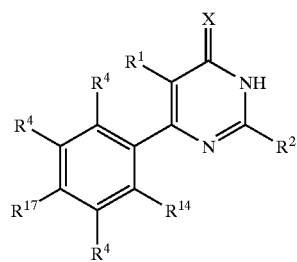

wherein, $R^1$ is CN;

$R^2$ is $NR^5R^{15}$; $OR^5$; $R^8$; aryl; $N(R^5)$—$N$=$CH(R^8)$; $N(R^5)$—$N$=$CH(aryl)$; $NR^5$—$NR^5C(O)NR^5R^5$; $NR^5$—$NR^5R^{16}$; $NR^5$—$NR^5R^6$; C1–C10 alkyl substituted with aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)NR^5R^5$, or $S(O)_2NR^5R^5$; or C1–C10 alkenyl substituted with aryl, $R^8$, halo, $CF_3$, $SR^5$, $OR^5$, $OC(O)R^5$, $NR^5R^5$, $NR^5R^6$, $COOR^5$, $NO_2$, CN, $C(O)R^5$, $C(O)NR^5R^5$, or $S(O)_2NR^5R^5$;

X is O or S;

Each $R^4$ is independently selected from H, C1–C10 alkyl; C2–C10 alkenyl; C2–C10 alkynyl; C3–C10 cycloalkyl; C4–C10 cycloalkenyl; aryl; $R^8$; halo; haloalkyl; $CF_3$; $SR^5$; $OR^5$; $NR^5R^5$; $NR^5R^6$; $COOR^5$; $NO_2$; CN; $C(O)R^5$; $C(O)C(O)R^5$; $C(O)NR^5R^5$; $OC(O)R^5$; $S(O)_2R^5$; $S(O)_2NR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; $NR^5C(O)C(O)NR^5R^6$; C1–C10 alkyl substituted with aryl, $R^7$ or $R^8$; or C1–C10 alkenyl substituted with aryl, $R^7$ or $R^8$;

Each $R^5$ is independently H; C1–C10 alkyl; C2–C10 alkenyl; C2–C10 alkynyl; C3–Cor cycloalkyl; C4–C10 cycloalkenyl; aryl; $R^9$; C1–C10 alkyl substituted with one or two independent aryl, $R^7$ or $R^9$ groups; C3–C10 cycloalkyl substituted with one or two independent aryl, $R^7$ or $R^9$ groups; or C1–C10 alkenyl substituted with aryl, $R^7$ or $R^9$;

Each $R^6$ is independently $C(O)R^5$, $COOR^5$, or $S(O)_2R^5$;

Each $R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, or $C(O)NR^{10}R^{10}$;

Each $R^8$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; aryl; $R^9$; halo; sulfur; oxygen; $CF_3$; haloalkyl; $SR^5$; $OR^5$; $OC(O)R^5$; $NR^5R^5$; $NR^5R^6$; $NR^6R^6$; $COOR^5$; $NO_2$; CN; $C(O)R^5$; $C(O)NR^5R^5$; C1–C10 alkyl substituted with $R^7$, $R^9$ or aryl; C1–C10 alkenyl substituted with $R^7$, $R^9$ or aryl;

Each $R^9$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; halo; sulfur; oxygen; $CF_3$; haloalkyl; $SR^{10}$; $OR^{10}$; $NR^{10}R^{10}$; $NR^{10}R^{11}$; $NR^{11}R^{11}$; $COOR^{10}$; $NO_2$; CN; $C(O)R^{10}$; or $C(O)NR^{10}R^{10}$;

Each $R^{10}$ is independently H, C1–C10 alkyl; C2–C10 alkenyl; C2–C10 alkynyl; C3–C10 cycloalkyl; C4–C10 cycloalkenyl; haloalkyl; C1–C10 alkyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, NHC(O)

R¹³, or OC(O)R¹³; or phenyl optionally substituted with 1–3 independent C1–C10 alkyl, C2–C10 alkenyl, C2–C10 alkynyl, C3–C10 cycloalkyl, C4–C10 cycloalkenyl, halo, CF₃, OR¹³, SR¹³, NR¹³R¹³, COOR¹³, NO₂, CN, C(O)R¹³, C(O)NR¹³R¹³, NHC(O)R¹³, or OC(O)R¹³;

Each R¹¹ is independently C(O)R¹⁰, COOR¹⁰, or S(O)₂R¹⁰;

Each R¹² is independently H, C1–C10 alkyl, C2–C10 alkenyl, C2–C10 alkynyl, C3–C10 cycloalkyl, C4–C10 cycloalkenyl, or phenyl optionally substituted with 1–3 independent C1–C10 alkyl, C2–C10 alkenyl, C2–C10 alkynyl, C3–C10 cycloalkyl, C4–C10 cycloalkenyl, halo, CF₃, OR¹³, SR¹³, NR¹³R¹³, COOR¹³, NO₂, CN, C(O)R¹³, C(O)NR¹³R¹³, NHC(O)R¹³, or OC(O)R¹³;

Each R¹³ is independently H; C1–C10 alkyl; C2–C10 alkenyl; C2–C10 alkynyl; C3–C10 cycloalkyl; C4–C10 cycloalkenyl; C1–C10 alkyl optionally substituted with halo, CF₃, OR¹⁹, SR¹⁹, NR¹⁹R¹⁹, COOR¹⁹, NO₂, CN; or phenyl optionally substituted with halo, CF₃, OR¹⁹, SR¹⁹, NR¹⁹R¹⁹, COOR¹⁹, NO₂, CN;

Each R¹⁴ is independently selected from C1–C10 alkyl; C2–C10 alkenyl; C2–C10 alkynyl; C3–C10 cycloalkyl; C4–C10 cycloalkenyl; aryl; R⁸; halo; haloalkyl; CF₃; SR⁵; OR⁵; NR⁵R⁵; NR⁵R⁵; COOR⁵; NO₂; CN; C(O)R⁵; C(O)C(O)R⁵; C(O)NR⁵R⁵; OC(O)R⁵; S(O)₂R⁵; S(O)₂NR⁵R⁵; NR⁵C(O)NR⁵R⁵; NR⁵C(O)C(O)R⁵; NR⁵C(O)R⁵; NR⁵(COOR⁵); NR⁵C(O)R⁸; NR⁵S(O)₂NR⁵R⁵; NR⁵S(O)₂R⁵; NR⁵S(O)₂R⁸; NR⁵C(O)C(O)NR⁵R⁵; NR⁵C(O)C(O)NR⁵R⁶; C1–C10 alkyl substituted with aryl, R⁷ or R⁸; or C1–C10 alkenyl substituted with aryl, R⁷ or R⁸;

Each R¹⁵ is independently C1–C10 alkyl; C2–C10 alkenyl; C2–C10 alkynyl; C3–C10 cycloalkyl; C4–C10 cycloalkenyl; aryl; R⁹; C1–C10 alkyl substituted with one or two independent aryl, R⁷ or R⁹ groups; or C1–C10 alkenyl substituted with aryl, R⁷ or R⁹;

Each R¹⁶ is independently H; C1–C10 alkyl; C2–C10 alkenyl; C2–C10 alkynyl; C3–C10 cycloalkyl; C4–C10 cycloalkenyl; aryl; R⁹; C1–C10 alkyl substituted with one or two independent aryl, R⁷ or R⁹ groups; or C1–C10 alkenyl substituted with aryl, R⁷ or R⁹;

Each R¹⁷ is independently selected from H, C1–C10 alkyl; C2–C10 alkenyl; C2–C10 alkynyl; C3–C10 cycloalkyl; C4–C10 cycloalkenyl; aryl; R⁸; halo; haloalkyl; CF₃; SR⁵; OR⁵; NR⁵R⁵; NR⁵R⁶; COOR⁵; NO₂; CN; C(O)R⁵; C(O)C(O)R⁵; C(O)NR⁵R⁵; OC(O)R⁵; S(O)₂R⁵; S(O)₂NR⁵R⁵; NR⁵C(O)NR⁵R⁵; NR⁵C(O)C(O)R⁵; NR⁵C(O)R⁵; NR⁵(COOR⁵); NR⁵C(O)R⁸; NR⁵S(O)₂NR⁵R⁵; NR⁵S(O)₂R⁵; NR⁵S(O)₂R⁸; NR⁵C(O)C(O)NR⁵R⁵; NR⁵C(O)C(O)NR⁵R⁶; C1–C10 alkyl substituted with aryl, R⁷ or R⁸; or C1–C10 alkenyl substituted with aryl, R⁷ or R⁸;

Each R¹⁹ is independently H; C1–C10 alkyl; C3–C10 cycloalkyl or phenyl;

Each haloalkyl is independently a C1–C10 alkyl substituted with one or more halogen atoms, selected from F, Cl, Br, or I, wherein the number of halogen atoms may not exceed that number that results in a perhaloalkyl group;

Each aryl is independently a 6-carbon monocyclic or 10-carbon bicyclic aromatic ring system optionally substituted with 1–3 independent C1–C10 alkyl; C2–C10 alkenyl; C2–C10 alkynyl; C3–C10 cycloalkyl; C4–C10 cycloalkenyl; R⁹; halo; haloalkyl; CF₃; OR¹²;

SR¹²; NR¹²R¹²; COOR¹²; NO₂; CN; C(O)R¹²; C(O)C(O)R¹²; C(O)NR¹²R¹²; S(O)₂R¹²; N(R¹²)C(O)R¹²; N(R¹²)(COOR¹²); N(R¹²)S(O)₂R¹²; S(O)₂NR¹²R¹²; OC(O)R¹²; NR¹²C(O)NR¹²R¹²; NR¹²C(O)C(O)R¹²; NR¹²C(O)R¹²; NR¹²S(O)₂NR¹²R¹²; NR¹²S(O)₂R⁹; NR¹²C(O)C(O)NR¹²R¹²; C1–C10 alkyl substituted with 1–3 independent R⁹, halo, CF₃, OR¹², SR¹², NR¹²R¹², COOR¹², NO₂, CN, C(O)R¹², C(O)NR¹²R¹², NHC(O)R¹², NH(COOR¹²), S(O)₂NR¹²R¹², OC(O)R¹²; C2–C10 alkenyl substituted with 1–3 independent R⁹, halo, CF₃, OR¹², SR¹², NR¹²R¹², COOR¹², NO₂, CN, C(O)R¹², C(O)NR¹²R¹², NHC(O)R¹², NH(COOR¹²), S(O)₂NR¹²R¹², OC(O)R¹²; or R¹²;

wherein R¹⁴ and R¹⁷ may not simultaneously be Cl and wherein R¹⁴ may not simultaneously be methyl when all R⁴ and R¹⁷ are H. Preferred compounds of this embodiment are also those wherein X is O. Alternatively, the compound has the formula directly above wherein each R¹⁷ is independently selected from from H, C1–C10 alkyl; C2–C10 alkenyl; C2–C10 alkynyl; C3–C10 cycloalkyl; C4–C10 cycloalkenyl; aryl; R⁸; I; Br; F; CF₃; SR⁵; OR⁵; NR⁵R⁵; NR⁵R⁶; COOR⁵; NO₂; CN; C(O)R⁵; C(O)C(O)R⁵; C(O)NR⁵R⁵; S(O)₂NR⁵R⁵; NR⁵C(O)NR⁵R⁵; NR⁵C(O)C(O)R⁵; NR⁵C(O)R⁸; NR⁵S(O)₂NR⁵R⁵; NR⁵S(O)₂R⁵; NR⁵S(O)₂R⁸; NR⁵C(O)C(O)NR⁵R⁵; C1–C10 alkyl substituted with aryl, R⁷ or R⁸; or C1–C10 alkenyl substituted with aryl, R⁷ or R⁸. Alternatively, the compound has the formula directly above wherein each R¹⁴ is independently selected from NR⁵R⁵; NR⁵R⁶; NR⁵C(O)NR⁵R⁵; NR⁵C(O)C(O)R⁵; NR⁵C(O)R⁵; NR⁵(COOR⁵); NR⁵C(O)R⁸; NR⁵S(O)₂NR⁵R⁵; NR⁵S(O)₂R⁵; NR⁵S(O)₂R⁸; NR⁵C(O)C(O)NR⁵R⁵; or NR⁵C(O)C(O)NR⁵R⁶. In alternate embodiments, the compound is of any of the formulae above, wherein at least two of R⁴ and/or R¹⁷ are independently H. Preferred compounds of these embodiments are also those wherein X is O.

In another embodiment, the inhibitory compound has the formula,

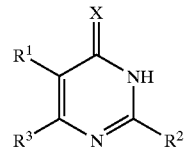

wherein,

R¹ is CN;

R² is NR⁵R¹⁵; OR⁵; R⁸; aryl; N(R⁵)—N=CH(R⁸); N(R⁵)—N=CH(aryl); NR⁵—NR⁵C(O)NR⁵R⁵; NR⁵—NR⁵R¹⁶; NR⁵—NR⁵R⁶; C1–C10 alkyl substituted with aryl, R⁸, halo, CF₃, SR⁵, OR⁵, OC(O)R⁵, NR⁵R⁵, NR⁵R⁶, COOR⁵, NO₂, CN, C(O)R⁵, C(O)NR⁵R⁵, or S(O)₂NR⁵R⁵; or C1–C10 alkenyl substituted with aryl, R⁸, halo, CF₃, SR⁵, OR⁵, OC(O)R⁵, NR⁵R⁵, NR⁵R⁶, COOR⁵, NO₂, CN, C(O)R⁵, C(O)NR⁵R⁵, or S(O)₂NR⁵R⁵;

R³ is R⁸; COOR⁵; or C1–C10 alkyl substituted with R⁷, R⁸, or phenyl substituted with 1–3 independent C1–C10 alkyl, C2–C10 alkenyl, C2–C10 alkynyl, C3–C10 cycloalkyl, C4–C10 cycloalkenyl, R⁹, halo, CF₃, OR¹², SR¹², NR¹²R¹², COOR¹², NO₂, CN, C(O)R¹², C(O)NR¹²R¹², NHC(O)R¹², NH(COOR¹²), S(O)₂NR¹²R¹², OC(O)R¹², C1–C10 alkyl substituted with R⁹, halo, CF₃, OR¹², SR¹², NR¹²R¹², COOR¹², NO₂, CN, C(O)R$^{12}$, C(O)NR$^{12}$R$^{12}$, NHC(O)R$^{12}$, NH(COOR$^{12}$), S(O)$_2$NR$^{12}$R$^{12}$, OC(O)R$^{12}$; wherein R$^3$ is not unsubstituted furanyl, unsubstituted thienyl or unsubstituted pyridyl;

X is O or S;

Each R$^4$ is independently selected from H, C1–C10 alkyl; C2–C10 alkenyl; C2–C10 alkynyl; C3–C10 cycloalkyl; C4–C10 cycloalkenyl; aryl; R$^8$; halo; haloalkyl; CF$_3$; SR$^5$; OR$^5$; NR$^5$R$^5$; NR$^5$R$^6$; COOR$^5$; NO$_2$; CN; C(O)R$^5$; C(O)C(O)R$^5$; C(O)NR$^5$R$^5$; OC(O)R$^5$; S(O)$_2$R$^5$; S(O)$_2$NR$^5$R$^5$; NR$^5$C(O)NR$^5$R$^5$; NR$^5$C(O)C(O)R$^5$; NR$^5$C(O)R$^5$; NR$^5$(COOR$^5$); NR$^5$C(O)R$^8$; NR$^5$S(O)$_2$NR$^5$R$^5$; NR$^5$S(O)$_2$R$^5$; NR$^5$S(O)$_2$R$^8$; NR$^5$C(O)C(O)NR$^5$R$^5$; NR$^5$C(O)C(O)NR$^5$R$^6$; C1–C10 alkyl substituted with aryl, R$^7$ or R$^8$; or C1–C10 alkenyl substituted with aryl, R$^7$ or R$^8$;

Each R$^5$ is independently H; C1–C10 alkyl; C2–C10 alkenyl; C2–C10 alkynyl; C3–C10 cycloalkyl; C4–C10 cycloalkenyl; aryl; R$^9$; C1–C10 alkyl substituted with one or two independent aryl, R$^7$ or R$^9$ groups; C3–C10 cycloalkyl substituted with one or two independent aryl, R$^7$ or R$^9$ groups; or C1–C10 alkenyl substituted with aryl, R$^7$ or R$^9$;

Each R$^6$ is independently C(O)R$^5$, COOR$^5$, or S(O)$_2$R$^5$;

Each R$^7$ is independently halo, CF$_3$, SR$^{10}$, OR$^{10}$, OC(O)R$^{10}$, NR$^{10}$R$^{10}$, NR$^{10}$R$^{11}$, NR$^{11}$R$^{11}$, COOR$^{10}$, NO$_2$, CN, C(O)R$^{10}$, or C(O)NR$^{10}$R$^{10}$;

Each R$^8$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; aryl; R$^9$; halo; sulfur; oxygen; CF$_3$; haloalkyl; SR$^5$; OR$^5$; OC(O)R$^5$; NR$^5$R$^5$; NR$^5$R$^6$; NR$^6$R$^6$; COOR$^5$; NO$_2$; CN; C(O)R$^5$; C(O)NR$^5$R$^5$; C1–C10 alkyl substituted with R$^7$, R$^9$ or aryl; C1–C10 alkenyl substituted with R$^7$, R$^9$ or aryl;

Each R$^9$ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; halo; sulfur; oxygen; CF$_3$; haloalkyl; SR$^{10}$; OR$^{10}$; NR$^{10}$R$^{10}$; NR$^{10}$R$^{11}$; NR$^{11}$R$^{11}$; COOR$^{10}$; NO$_2$; CN; C(O)R$^{10}$; or C(O)NR$^{10}$R$^{10}$;

Each R$^{10}$ is independently H, C1–C10 alkyl; C2–C10 alkenyl; C2–C10 alkynyl; C3–C10 cycloalkyl; C4–C10 cycloalkenyl; haloalkyl; C1–C10 alkyl optionally substituted with 1–3 independent C1–C10 alkyl, C2–C10 alkenyl, C2–C10 alkynyl, C3–C10 cycloalkyl, C4–C10 cycloalkenyl, halo, CF$_3$, OR$^{13}$, SR$^{13}$, NR$^{13}$R$^{13}$, COOR$^{13}$, NO$_2$, CN, C(O)R$^{13}$, C(O)NR$^{13}$R$^{13}$, NHC(O)R$^{13}$, or OC(O)R$^{13}$; or phenyl optionally substituted with 1–3 independent C1–C10 alkyl, C2–C10 alkenyl, C2–C10 alkynyl, C3–C10 cycloalkyl, C4–C10 cycloalkenyl, halo, CF$_3$, OR$^{13}$, SR$^{13}$, NR$^{13}$R$^{13}$, COOR$^{13}$, NO$_2$, CN, C(O)R$^{13}$, C(O)NR$^{13}$R$^{13}$, NHC(O)R$^{13}$, or OC(O)R$^{13}$;

Each R$^{11}$ is independently C(O)R$^{10}$, COOR$^{10}$, or S(O)$_2$R$^{10}$;

Each R$^{12}$ is independently H, C1–C10 alkyl, C2–C10 alkenyl, C2–C10 alkynyl, C3–C10 cycloalkyl, C4–C10 cycloalkenyl, or phenyl optionally substituted with 1–3 independent C1–C10 alkyl, C2–C10 alkenyl, C2–C10 alkynyl, C3–C10 cycloalkyl, C4–C10 cycloalkenyl, halo, CF$_3$, OR$^{13}$, SR$^{13}$, NR$^{13}$R$^{13}$, COOR$^{13}$, NO$_2$, CN, C(O)R$^{13}$, C(O)NR$^{13}$R$^{13}$, NHC(O)R$^{13}$, or OC(O)R$^{13}$;

Each R$^{13}$ is independently H; C1–C10 alkyl; C2–C10 alkenyl; C2–C10 alkynyl; C3–C10 cycloalkyl; C4–C10 cycloalkenyl; C1–C10 alkyl optionally substituted with halo, CF$_3$, OR$^{19}$, SR$^{19}$, NR$^{19}$R$^{19}$, COOR$^{19}$, NO$_2$, CN; or phenyl optionally substituted with halo, CF$_3$, OR$^{19}$, SR$^{19}$, NR$^{19}$R$^{19}$, COOR$^{19}$, NO$_2$, CN;

Each R$^{15}$ is independently C1–C10 alkyl; C2–C10 alkenyl; C2–C10 alkynyl; C3–C10 cycloalkyl; C4–C10 cycloalkenyl; aryl; R$^9$; C1–C10 alkyl substituted with one or two independent aryl, R$^7$ or R$^9$ groups; or C1–C10 alkenyl substituted with aryl, R$^7$ or R$^9$;

Each R$^{16}$ is independently C1–C10 alkyl; C2–C10 alkenyl; C2–C10 alkynyl; C3–C10 cycloalkyl; C4–C10 cycloalkenyl; R$^9$; C1–C10 alkyl substituted with one or two independent aryl, R$^7$ or R$^9$ groups; C1–C10 alkenyl substituted with aryl, R$^7$ or R$^9$; or phenyl substituted with 1–3 independent C1–C10 alkyl, C2–C10 alkenyl, C2–C10 alkynyl, C3–C10 cycloalkyl, C4–C10 cycloalkenyl, R$^9$, halo, CF$_3$, OR$^{12}$, SR$^{12}$, NR$^{12}$R$^{12}$, COOR$^{12}$, NO$_2$, CN, C(O)R$^{12}$, C(O)NR$^{12}$R$^{12}$, NHC(O)R$^{12}$, NH(COOR$^{12}$), S(O)$_2$NR$^{12}$R$^{12}$, OC(O)R$^{12}$, C1–C1 alkyl substituted with R$^9$, halo, CF$_3$, OR$^{12}$, SR$^{12}$, NR$^{12}$R$^{12}$, COOR$^{12}$, NO$_2$, CN, C(O)R$^{12}$, C(O)NR$^{12}$R$^{12}$, NHC(O)R$^{12}$, NH(COOR$^{12}$), S(O)$_2$NR$^{12}$R$^{12}$, OC(O)R$^{12}$;

Each R$^{19}$ is independently H; C1–C1 alkyl; C3–C10 cycloalkyl or phenyl;

Each haloalkyl is independently a C1–C10 alkyl substituted with one or more halogen atoms, selected from F, Cl, Br, or I, wherein the number of halogen atoms may not exceed that number that results in a perhaloalkyl group;

Each aryl is independently a 6-carbon monocyclic or 10-carbon bicyclic aromatic ring system optionally substituted with 1–3 independent C1–C10 alkyl; C2–C10 alkenyl; C2–C10 alkynyl; C3–C10 cycloalkyl; C4–C10 cycloalkenyl; R$^9$; halo; haloalkyl; CF$_3$; OR$^{12}$; SR$^{12}$; NR$^{12}$R$^{12}$; COOR$^{12}$; NO$_2$; CN; C(O)R$^{12}$; C(O)C(O)R$^{12}$; C(O)NR$^{12}$R$^{12}$; S(O)$_2$R$^{12}$; N(R$^{12}$)C(O)R$^{12}$; N(R$^{12}$)(COOR$^{12}$); N(R$^{12}$)S(O)$_2$R$^{12}$; S(O)$_2$NR$^{12}$R$^{12}$; OC(O)R$^{12}$; NR$^{12}$C(O)NR$^{12}$R$^{12}$; NR$^{12}$C(O)C(O)R$^{12}$; NR$^{12}$C(O)R$^9$; NR$^{12}$S(O)$_2$NR$^{12}$R$^{12}$; NR$^{12}$S(O)$_2$R$^9$; NR$^{12}$C(O)C(O)NR$^{12}$R$^{12}$; C1–C10 alkyl substituted with 1–3 independent R$^9$, halo, CF$_3$, OR$^{12}$, SR$^{12}$, NR$^{12}$R$^{12}$, COOR$^{12}$, NO$_2$, CN, C(O)R$^{12}$, C(O)NR$^{12}$R$^{12}$, NHC(O)R$^{12}$, NH(COOR$^{12}$), S(O)$_2$NR$^{12}$R$^{12}$, OC(O)R$^{12}$; C2–C10 alkenyl substituted with 1–3 independent R$^9$, halo, CF$_3$, OR$^{12}$, SR$^{12}$, NR$^{12}$R$^{12}$, COOR$^{12}$, NO$_2$, CN, C(O)R$^{12}$, C(O)NR$^{12}$R$^{12}$, NHC(O)R$^{12}$, NH(COOR$^{12}$), S(O)$_2$NR$^{12}$R$^{12}$, OC(O)R$^{12}$; or R$^{12}$. Alternatively, the compound has the formula directly above wherein each R$^3$ is R$^8$, and alternatively, wherein R$^3$ is R$^8$ that is attached by a nitrogen atom in the R$^8$ ring system. Preferred compounds of these embodiments are also those wherein X is O.

In another embodiment, the inhibitory compound has the formula,

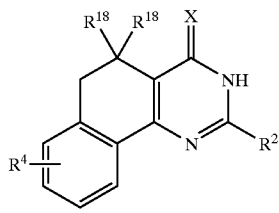

wherein,

R² is NR⁵R⁵; SR⁵; OR⁵; R⁸; aryl; N(R⁵)—N=CH(R⁸); N(R⁵)—N=CH(aryl); NR⁵—NR⁵C(O)NR⁵R⁵; NR⁵—NR⁵R¹⁵; NR⁵—NR⁵R⁶; C1–C10 alkyl substituted with aryl, R⁸, halo, CF₃, SR⁵, OR⁵, OC(O)R⁵, NR⁵R⁵, NR⁵R⁶, COOR⁵, NO₂, CN, C(O)R⁵, C(O)NR⁵R⁵, or S(O)₂NR⁵R⁵; or C1–C10 alkenyl substituted with aryl, R⁸, halo, CF₃, SR⁵, OR⁵, OC(O)R⁵, NR⁵R⁵, NR⁵R⁶, COOR⁵, NO₂, CN, C(O)R⁵, C(O)NR⁵R⁵, or S(O)₂NR⁵R⁵;

X is O or S;

R⁴ is one, two, or three substituents, each independently selected from H, C1–C10 alkyl; C2–C10 alkenyl; C2–C10 alkynyl; C3–C10 cycloalkyl; C4–C10 cycloalkenyl; aryl; R⁸; halo; haloalkyl; CF₃; SR⁵; OR⁵; NR⁵R⁵; NR⁵R⁶; COOR⁵; NO₂; CN; C(O)R⁵; C(O)C(O)R⁵; C(O)NR⁵R⁵; OC(O)R⁵; S(O)₂R⁵; S(O)₂NR⁵R⁵; NR⁵C(O)NR⁵R⁵; NR⁵C(O)C(O)R⁵; NR⁵C(O)R⁵; NR⁵(COOR⁵); NR⁵C(O)R⁸; NR⁵S(O)₂NR⁵R⁵; NR⁵S(O)₂R⁵; NR⁵S(O)₂R⁸; NR⁵C(O)C(O)NR⁵R⁵; NR⁵C(O)C(O)NR⁵R⁶; C1–C10 alkyl substituted with aryl, R⁷ or R⁸; or C1–C10 alkenyl substituted with aryl, R⁷ or R⁸;

Each R⁵ is independently H; C1–C10 alkyl; C2–C10 alkenyl; C2–C10 alkynyl; C3–C10 cycloalkyl; C4–C10 cycloalkenyl; aryl; R⁹; C1–C10 alkyl substituted with one or two independent aryl, R⁷ or R⁹ groups; C3–C10 cycloalkyl substituted with one or two independent aryl, R⁷ or R⁹ groups; or C1–C10 alkenyl substituted with aryl, R⁷ or R⁹;

Each R⁶ is independently C(O)R⁵, COOR⁵, or S(O)₂R⁵;

Each R⁷ is independently halo, CF₃, SR¹⁰, OR¹⁰, OC(O)R¹⁰, NR¹⁰R¹⁰, NR¹⁰R¹¹, NR¹¹R¹¹, COOR¹⁰, NO₂, CN, C(O)R¹⁰, or C(O)NR¹⁰R¹⁰;

Each R⁸ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; aryl; R⁹; halo; sulfur; oxygen; CF₃; haloalkyl; SR⁵; OR⁵; OC(O)R⁵; NR⁵R⁵; NR⁵R⁶; NR⁶R⁶; COOR⁵; NO₂; CN; C(O)R⁵; C(O)NR⁵R⁵; C1–C10 alkyl substituted with R⁷, R⁹ or aryl; C1–C10 alkenyl substituted with R⁷, R⁹ or aryl;

Each R⁹ is independently a 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; halo; sulfur; oxygen; CF₃; haloalkyl; SR¹⁰; OR¹⁰; NR¹⁰R¹⁰; NR¹⁰R¹¹; NR¹¹R¹¹; COOR¹⁰; NO₂; CN; C(O)R¹⁰; or C(O)NR¹⁰R¹⁰;

Each R¹⁰ is independently H, C1–C10 alkyl; C2–C10 alkenyl; C2–C10 alkynyl; C3–C10 cycloalkyl; C4–C10 cycloalkenyl; haloalkyl; C1–C10 alkyl optionally substituted with 1–3 independent C1–C10 alkyl, C2–C10 alkenyl, C2–C10 alkynyl, C3–C10 cycloalkyl, C4–C10 cycloalkenyl, halo, CF₃, OR¹³, SR¹³, NR¹³R¹³, COOR¹³, NO₂, CN, C(O)R¹³, C(O)NR¹³R¹³, NHC(O)R¹³, or OC(O)R¹³; or phenyl optionally substituted with 1–3 independent C1–C10 alkyl, C2–C10 alkenyl, C2–C10 alkynyl, C3–C10 cycloalkyl, C4–C10 cycloalkenyl, halo, CF₃, OR¹³, SR¹³, NR¹³R¹³, COOR¹³, NO₂, CN, C(O)R¹³, C(O)NR¹³R¹³, NHC(O)R¹³, or OC(O)R¹³;

Each R¹¹ is independently C(O)R¹⁰, COOR¹⁰, or S(O)₂R¹⁰;

Each R¹² is independently H, C1–C10 alkyl, C2–C10 alkenyl, C2–C10 alkynyl, C3–C10 cycloalkyl, C4–C10 cycloalkenyl, or phenyl optionally substituted with 1–3 independent C1–C10 alkyl, C2–C10 alkenyl, C2–C10 alkynyl, C3–C10 cycloalkyl, C4–C10 cycloalkenyl, halo, CF₃, OR¹³, SR¹³, NR¹³R¹³, COOR¹³, NO₂, CN, C(O)R¹³, C(O)NR¹³R¹³, NHC(O)R¹³, or OC(O)R¹³;

Each R¹³ is independently H; C1–C10 alkyl; C2–C10 alkenyl; C2–C10 alkynyl; C3–C10 cycloalkyl; C4–C10 cycloalkenyl; C1–C10 alkyl optionally substituted with halo, CF₃, OR¹⁹, SR¹⁹, NR¹⁹R¹⁹, COOR¹⁹, NO₂, CN; or phenyl optionally substituted with halo, CF₃, OR¹⁹, SR¹⁹, NR¹⁹R¹⁹, COOR¹⁹, NO₂, CN;

Each R¹⁸ is independently C1–C10 alkyl or both R¹⁸ may be taken together as a C2–C7 alkyl chain; wherein any R¹⁸ may optionally be substituted with 1–3 independent R⁷ or R⁸;

Each R¹⁹ is independently H; C1–C10 alkyl; C3–C10 cycloalkyl or phenyl;

Each haloalkyl is independently a C1–C10 alkyl substituted with one or more halogen atoms, selected from F, Cl, Br, or I, wherein the number of halogen atoms may not exceed that number that results in a perhaloalkyl group;

Each aryl is independently a 6-carbon monocyclic or 10-carbon bicyclic aromatic ring system optionally substituted with 1–3 independent C1–C10 alkyl; C2–C10 alkenyl; C2–C10 alkynyl; C3–C10 cycloalkyl; C4–C10 cycloalkenyl; R⁹; halo; haloalkyl; CF₃; OR¹²; SR¹²; NR¹²R¹²; COOR¹²; NO₂; CN; C(O)R¹²; C(O)C(O)R¹²; C(O)NR¹²R¹²; S(O)₂R¹²; N(R¹²)C(O)R¹²; N(R¹²)(COOR¹²); N(R¹²)S(O)₂R¹²; S(O)₂NR¹²R¹²; OC(O)R¹²; NR¹²C(O)NR¹²R¹²; NR¹²C(O)C(O)R¹²; NR¹²C(O)R⁹; NR¹²S(O)₂NR¹²R¹²; NR¹²S(O)₂R⁹; NR¹²C(O)C(O)NR¹²R¹²; C1–C10 alkyl substituted with 1–3 independent R⁹, halo, CF₃, OR¹², SR¹², NR¹²R¹², COOR¹², NO₂, CN, C(O)R¹², C(O)NR¹²R¹², NHC(O)R¹², NH(COOR¹²), S(O)₂NR¹²R¹², OC(O)R¹²; C2–C10 alkenyl substituted with 1–3 independent R⁹, halo, CF₃, OR¹², SR¹², NR¹²R¹², COOR¹², NO₂, CN, C(O)R¹², C(O)NR¹²R¹², NHC(O)R¹², NH(COOR¹²), S(O)₂NR¹²R¹², OC(O)R¹²; or R¹². Preferred compounds of this embodiment are also those wherein X is O.

Alternate embodiments of the invention are those of any of the formulae described herein wherein R² is NR¹⁵R⁵; wherein R² is NHR¹⁵; and wherein R² is NR⁵R¹⁵ and said $R^{15}$ is independently phenyl substituted with 1–3 independent C1–C10 alkyl; C2–C10 alkenyl; C2–C10 alkynyl; C3–C10 cycloalkyl; C4–C10 cycloalkenyl; $R^9$; halo; haloalkyl; $CF_3$; $OR^{12}$; $SR^{12}$; $NR^{12}R^{12}$; $COOR^{12}$; $NO_2$; CN; $C(O)R^{12}$; $C(O)C(O)R^{12}$; $C(O)NR^{12}R^{12}$; $S(O)_2R^{12}$; $N(R^{12})C(O)R^{12}$; $N(R^{12})(COOR^{12})$; $N(R^{12})S(O)_2R^{12}$; $S(O)_2NR^{12}R^{12}$; $OC(O)R^{12}$; $NR^{12}C(O)NR^{12}R^{12}$; $NR^{12}C(O)C(O)R^{12}$; $NR^{12}C(O)R^9$; $NR^{12}S(O)_2NR^{12}R^{12}$; $NR^{12}S(O)_2R^9$; $NR^{12}C(O)C(O)NR^{12}R^{12}$; C1–C10 alkyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$; C2–C10 alkenyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$; or $R^{12}$.

The invention also relates to methods of inhibiting enzyme or polypeptide activity, particularly of an enzyme or polypeptide described herein, such as a kinase, in a mammal comprising the step of administering to said mammal a compound of any of the formulae described herein or a composition comprising a compound of any of the formulae described herein. In one embodiment, the invention relates to a method of inhibiting kinase activity in a mammal comprising the step of administering to said mammal a compound, or a composition comprising a compound, of any one of the formulae described herein. Preferably, the mammal is a human.

In another embodiment, the invention relates to a method of inhibiting enzyme activity in a mammal comprising the step of administering to said mammal a compound, or a composition comprising a compound, of any of the formulae described herein. Preferably, the mammal is a human.

The invention also relates to methods of treating disease and/or disease symptoms, particularly those mediated by an enzyme or polypeptide described herein, such as kinase mediated disease or disease symptoms, in a mammal comprising the step of administering to said mammal a compound of any of the formulae described herein or a composition comprising a compound of any of the formulae described herein. Such diseases or disease symptoms are described herein. "Kinase mediated" disease or disease symptoms refers to disease or disease symptoms in which kinase activity is involved. In one embodiment, this invention relates to a method of treating disease or disease symptoms, particularly kinase mediated disease or disease symptoms, in a mammal comprising the step of administering to said mammal a compound, or a composition comprising a compound, of any of the formulae described herein. Preferably, the mammal is a human.

In an alternate embodiment, this invention relates to a method of treating disease or disease symptoms in a mammal comprising the step of administering to said mammal a compound, or a composition comprising a compound, of any of the formulae described herein. Preferably, the mammal is a human.

In the compounds described herein, the term "halo" refers to any radical of fluorine, chlorine, bromine or iodine. The terms "alkyl", "alkenyl" and "alkynyl" refer to hydrocarbon chains that may be straight-chain or branched-chain, containing the indicated number of carbon atoms. For example, C1–C10 indicates the group may have from 1 to 10 (inclusive) carbon atoms in it. The terms "ring" and "ring system" refer to a ring comprising the delineated number of atoms, said atoms being carbon or, where indicated, a heteroatom such as nitrogen, oxygen or sulfur. The ring itself, as well as any substitutents thereon, may be attached at any atom that allows a stable compound to be formed.

In the methods described herein, said mammal is preferably a human. The inhibitors described herein, however, are useful in inhibiting kinase activity in human cells and useful in murine and other species used as surrogates for investigating activity in vitro and in vivo in humans and against human kinases. The inhibitors described herein are also useful for investigating inhibition and activity of kinases originating from species other than humans.

The compounds and compositions described herein are useful for inhibition of kinase activity of one or more enzymes. Kinases include, for example, protein kinases, lipid kinases (e.g., phosphatidylinositol kinases PI-3, PI-4) and carbohydrate kinases. Further information relating to kinase structure, function and and their role in disease or disease symptoms is available at the Protein Kinase Resource web site (http://www.sdsc.edu/Kinases/pk_home.html). Kinases may be of prokaryotic, eukaryotic, bacterial, viral, fungal or archaea origin. Specifically, the compounds described herein are useful as inhibitors of tyrosine, serine/threonine or histidine protein kinases. Examples of kinases that are inhibited by the compounds and compositions described herein and against which the methods described herein are useful include, but are not limited to, LCK, IRK (=INSR=Insulin receptor), IGF-1 receptor, SYK, ZAP-70, IRAK1, IRAK2, BLK, BMX, BTK, FRK, FGR, FYN, HCK, ITK, LYN, TEC, TXK, YES, ABL, SRC, EGF-R (=ErbB-1), ErbB-2 (=NEU=HER2), ErbB-3, ErbB-4, FAK, FGF1R (=FGR-1), FGF2R (=FGR-2), IKK-1 (=IKK-ALPHA=CHUK), IKK-2 (=IKK-BETA), MET (=c-MET), NIK, PDGF receptor ALPHA, PDGF receptor BETA, TIE1, TIE2 (=TEK), VEGFR1 (=FLT-1), VEGFR2 (=KDR), FLT-3, FLT4, KIT, CSK, JAK1, JAK2, JAK3, TYK2, RIP, RIP-2, LOK, TAK1, RET, ALK, MLK3, COT, TRKA, PYK2, EPHB4, RON, GSK3, UL13, ORF47, ATM, CDK (including all subtypes), PKA, PKB (including all PKB subtypes) (=AKT-1, AKT-2, AKT-3), PKC (including all PKC subtypes), and bARK1 (=GRK2) (and other G-protein coupled receptor kinases (GRKs)), and all subtypes of these kinases. The compounds and compositions of the invention are therefore also particularly suited for treatment of diseases and disease symptoms that involve one or more of the aforementioned protein kinases. In one embodiment, the compounds, compositions or methods of this invention are particularly suited for inhibition of or treatment of disease or disease symptoms mediated by LCK, ZAP, LYN, EGFR, ERB-B2, KDR, ITK, BTK, or SYK. In another embodiment, the compounds, compositions or methods of this invention are particularly suited for inhibition of or treatment of disease or disease symptoms mediated by src-family kinases. In another embodiment, the compounds, compositions or methods of this invention are particularly suited for inhibition of or treatment of disease or disease symptoms mediated by kinases in one of the kinase families defined by Hardie & Hanks, ed. supra. The compounds and compositions are also suited for regulating or modulating signal transduction in signal transduction pathways that involve one or more kinases, thus affecting events in a cell, and are therefor useful in methods for regulating or modulating signal transduction.

The inhibitors described herein are also useful for inhibiting the biological activity of any enzyme comprising greater than 90%, alternatively greater than 85%, or alternatively greater than 70% sequence homology with a kinase sequence, including the kinases mentioned herein. The inhibitors described herein are also useful for inhibiting the biological activity of any enzyme comprising a subsequence, or variant thereof, of any enzyme that comprises greater than 90%, alternatively greater than 85%, or alternatively greater than 70% sequence homology with a kinase subsequence, including subsequences of the kinases mentioned herein. Such subsequence preferably comprises greater than 90%, alternatively greater than 85%, or alternatively greater than 70% sequence homology with the sequence of an active site or subdomain of a kinase enzyme. The subsequences, or variants thereof, comprise at least about 300, or alternatively at least about 200, amino acids.

The inhibitors described herein are useful for inhibiting the biological activity of any enzyme that binds ATP and thus for treating disease or disease symptoms mediated by any enzyme that binds ATP. The inhibitors described herein are also useful for inhibiting the biological activity of any enzyme that is involved in phosphotransfer and thus for treating disease or disease symptoms mediated by any enzyme that is involved in phosphotransfer. The inhibitors described herein are also useful for inhibiting the biological activity of a polypeptide or enzyme having sequence homology with a kinase sequence and thus for treating disease or disease symptoms mediated by such polypeptide or enzyme. Such polypeptides or enzymes may be identified by comparison of their sequence with kinase sequences and kinase catalytic domain sequences. For example, one method of comparison involves the database PROSITE (http://expasy.hcuge.ch), containing "signatures" or sequence patterns (or motifs) or profiles of protein families or domains. Thus, the inhibitors described herein are useful for inhibiting the biological activity of a polypeptide or enzyme comprising a sequence that comprises a "signature" or sequence pattern or profile derived for, and identified in PROSITE as relating to kinases, and for treating disease or disease symptoms mediated by such polypeptide or enzyme. Examples of such PROSITE motifs or consensus patterns identified as relating to kinases include PS00107, PS00108, PS00109, PS50011, PS00915, and PS00916.

The compounds, compositions and methods described herein are useful in inhibiting kinase activity. As such, the compounds, compositions and methods of this invention are useful in treating kinase-mediated disease or disease symptoms in a mammal, particularly a human. Kinase mediated diseases are those wherein a protein kinase is involved in signaling, mediation, modulation, or regulation of the disease process. Kinase mediated diseases are exemplified by the following disease classes: cancer, autoimmunological, metabolic, inflammatory, infection (bacterial, viral, yeast, fungal, etc.), diseases of the central nervous system, degenerative neural disease, allergy/asthma, angiogenesis, neovascularization, vasculogenesis, cardiovascular, and the like.

The compounds, compositions and methods described herein are useful in treating or preventing diseases or their symptoms, including, transplant rejection (e.g., kidney, liver, heart, lung, pancreas (islet cells), bone marrow, cornea, small bowel, skin allografts or xenografts), graft versus host disease, osteoarthritis, rheumatoid arthritis, multiple sclerosis, diabetes, diabetic retinopathy, asthma, inflammatory bowel disease (Crohn's disease, ulcerative colitis), renal disease, cachexia, septic shock, lupus, diabetes mellitus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, leukemia (acute myeloid, chronic myeloid, acute lymphoblastic, etc.), cancer (breast, lung, colorectal, ovary, prostate, renal, squamous cell, prostate, glioblastoma, melanoma, pancreatic, Kaposi's sarcoma, etc.), occular disease, retinopathies, (e.g., macular degeneration, diabetic retinopathy), corneal disease, glaucoma, bacterial infections, viral infections, fungal infections and heart disease, including but not limited to, restenosis. In one embodiment, the compositions and methods described herein are useful in treating or preventing rheumatoid arthritis, transplant rejection, asthma or allergy, or their symptoms.

Another embodiment envisioned by this invention relates to the use of the kinase inhibitory compounds described herein for use as reagents that effectively bind to kinases. As reagents, the compounds of this invention, and their derivatives, may be derivatized to bind to a stable resin as a tethered substrate for affinity chromatography applications. The compounds of this invention, and their derivatives, may also be modified (e.g., radiolabelled or affinity labelled, etc.) in order to utilize them in the investigation of enzyme or polypeptide characterization, structure, and/or function. These and other uses that characterize kinase inhibitors will be evident to those of ordinary skill in the art.

In another embodiment, the inhibitors described herein are useful for crystallizing or co-crystallizing with a protein kinase. Such crystals or crystal complexes may additionally comprise additional peptides and or metal ions. The crystals or crystal complexes may be used for investigation and determination of enzyme characteristics including, for example, structure of the kinase enzyme, enzyme active site domains, and inhibitor-enzyme interactions. This information is useful in developing inhibitor compounds with modified characteristics and for understanding structure-function relationships of the enzymes and their enzyme-inhibitor interactions.

In an alternate embodiment, the inhibitory compounds described herein may be used as platforms or scaffolds which may be utilized in combinatorial chemistry techniques for preparation of derivatives and/or chemical libraries of compounds. Such derivatives and libraries of compounds have kinase inhibitory activity and are useful for identifying and designing compounds possessing kinase inhibitory activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, A. W., *Curr. Opin. Chem. Bio.*, (1997) 1, 60. Thus, one embodiment relates to a method of using the compounds described in the formulae herein for generating derivatives or chemical libraries comprising: 1) providing a body comprising a plurality of wells; 2) providing one or more compounds of the formulae described herein in each well; 3) providing an additional one or more chemicals in each well; 4) isolating the resulting one or more products from each well. An alternate embodiment relates to a method of using the compounds described in the formulae herein for generating derivatives or chemical libraries comprising: 1) providing one or more compounds of the formulae described herein attached to a solid support; 2) treating the one or more compounds of the formulae described herein attached to a solid support with one or more additional chemicals; 3) isolating the resulting one or more products from the solid support. In the methods described above, "tags" or identifier or labeling moieties may be attached to and/or detached from the compounds of the formulae herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

The compounds of the formulae herein may be used to study the mechanism and role of enzymes in biological pathways and processes involving kinases. The compounds of the formulae herein may also be used as probes to identify new kinase enzymes or polypeptides with sequence homology to kinases. The inhibitor compounds may be tethered to a support or modified (e.g., tagged, radiolabeled or other identifiable detection method) such that the compound may be detected and isolated in the presence of the kinase enzyme or polypeptide. Thus, another embodiment relates to a method of identifying and/or isolating a kinase enzyme or polypeptide with sequence homology to a kinase enzyme sequence or subsequence, comprising, contacting a tethered or modified compound of any of the formulae herein with one or more polypeptides, isolating a polypeptide/inhibitor complex, and identifying or isolating the sequence of the polypeptide in the polypeptide/inhibitor complex. The identification of the polypeptide sequence may be performed while in the polypeptide/inhibitor complex or after the polypeptide is decomplexed from the tethered or modified compound of any of the formulae herein. Table 1 lists representative individual compounds of the invention and compounds employed in the compositions and methods of this invention.

TABLE 1
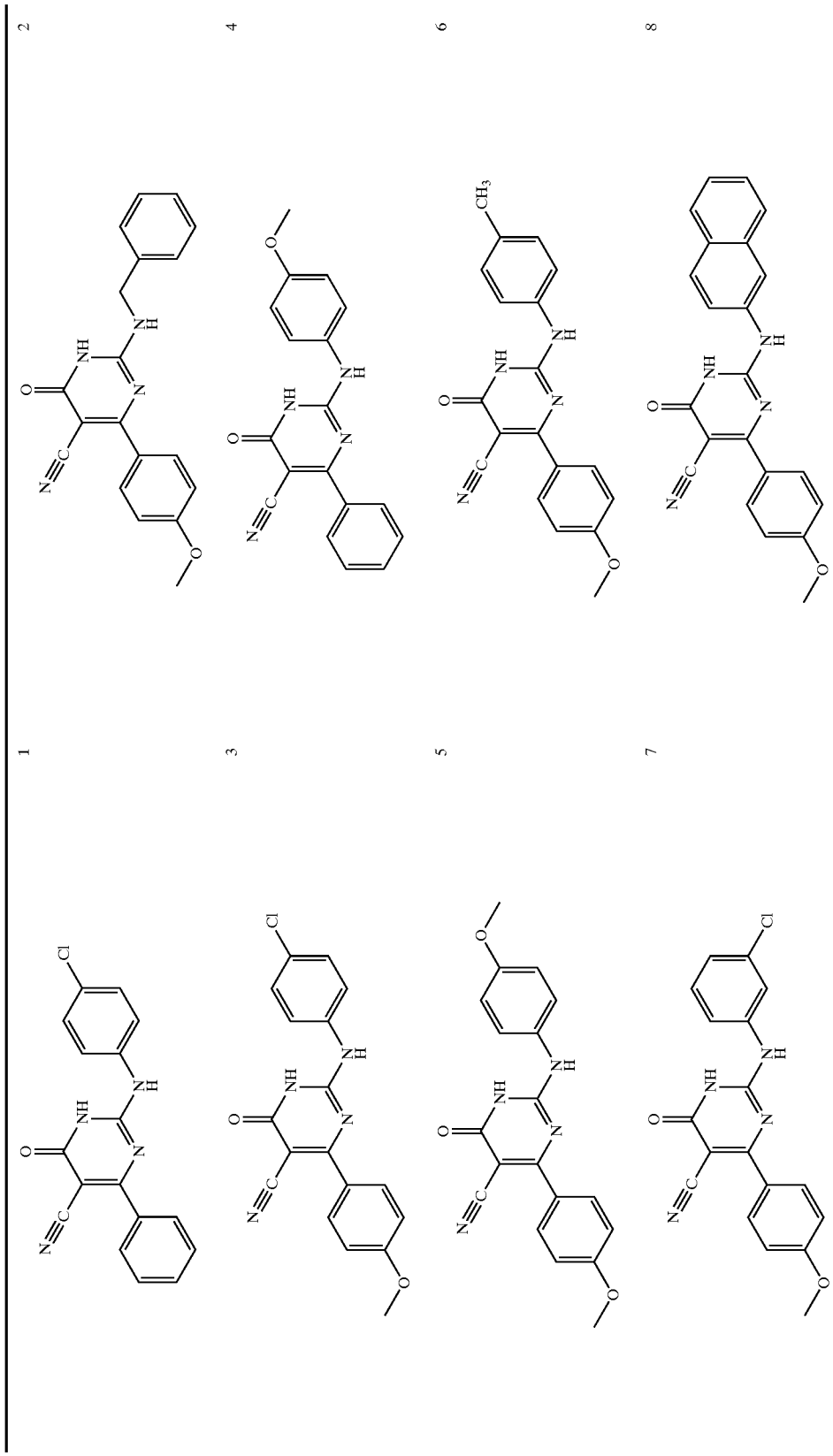

TABLE 1-continued
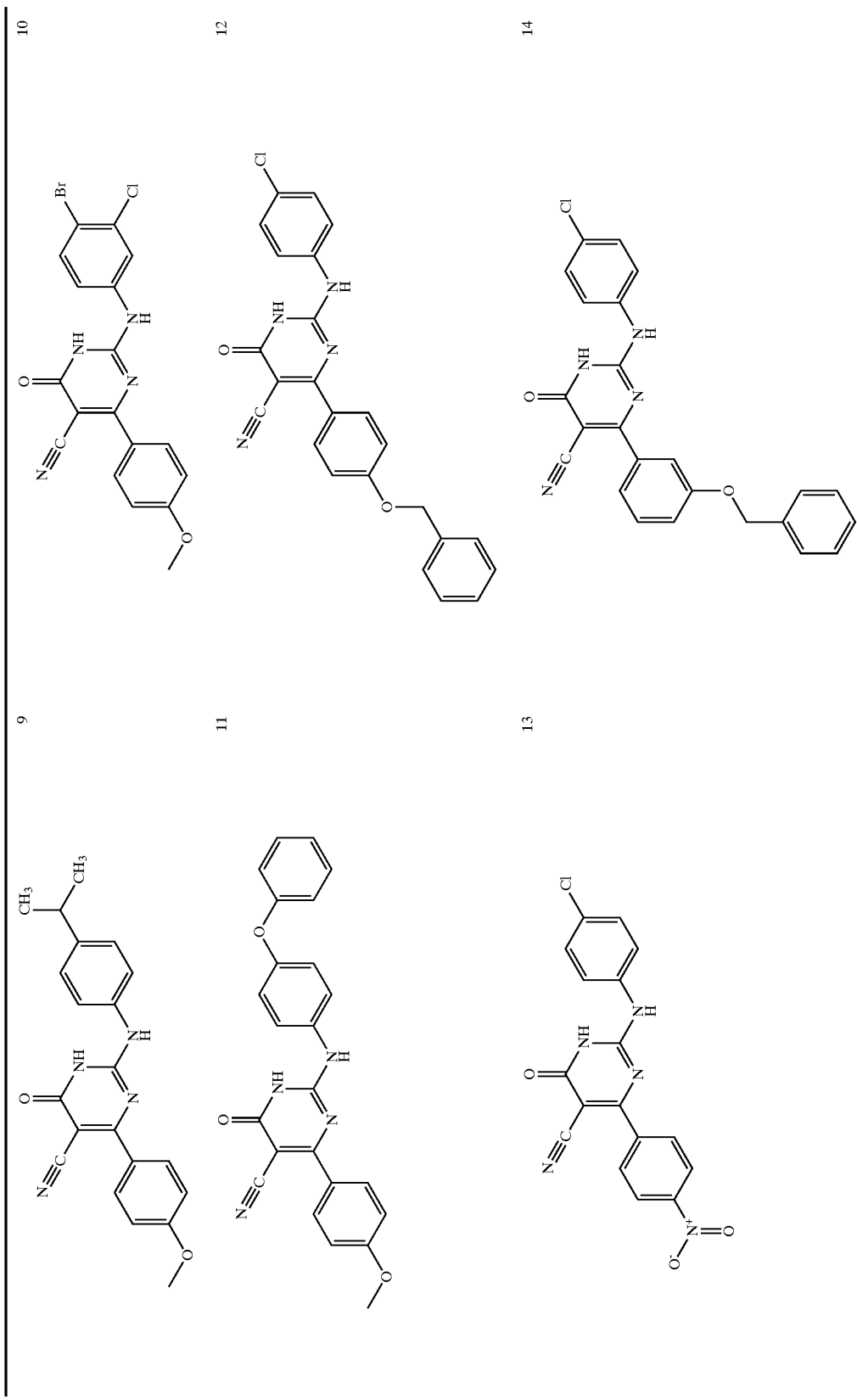

TABLE 1-continued
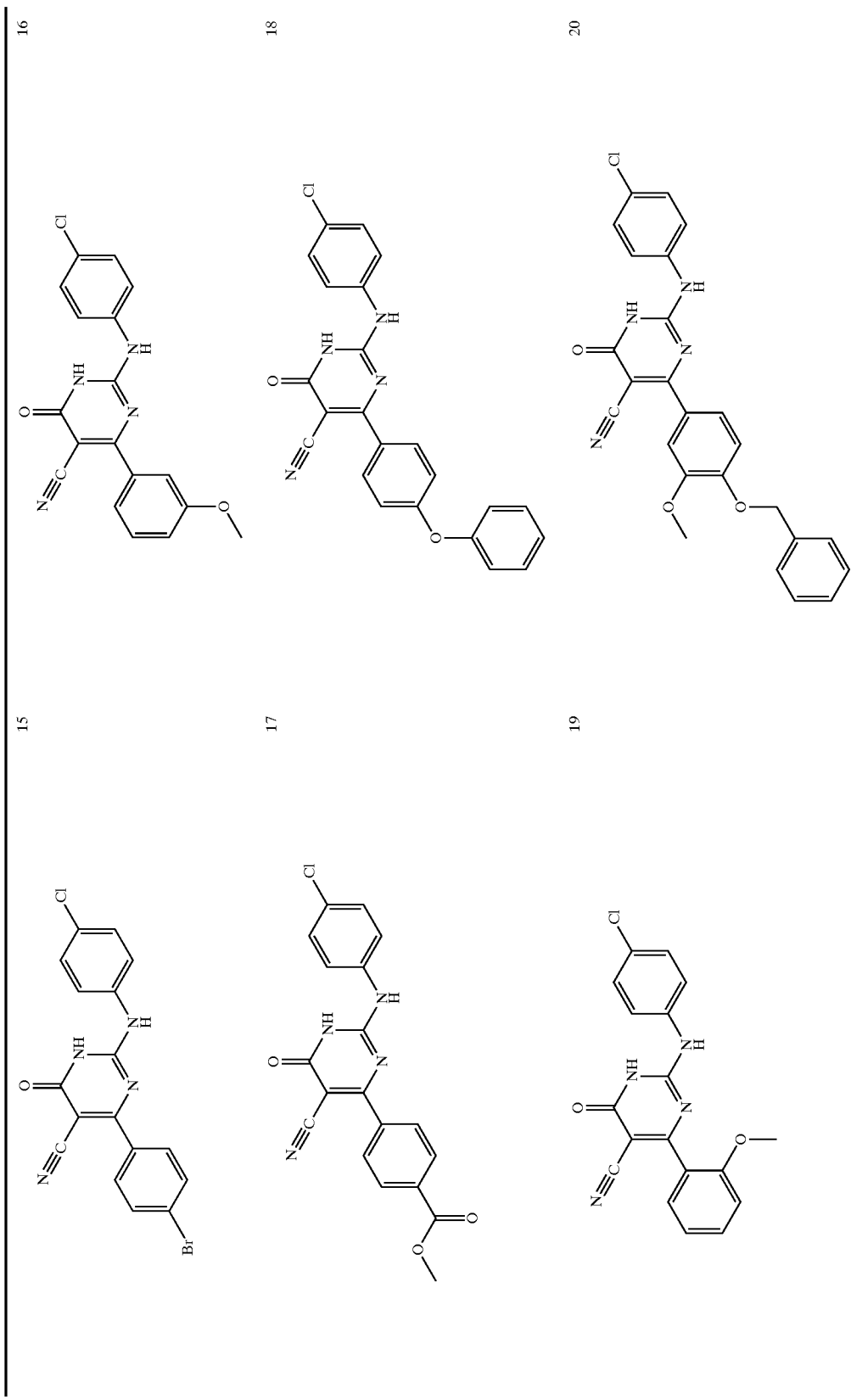

TABLE 1-continued
| 21 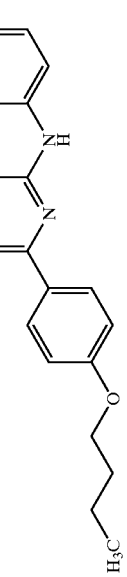 | 22 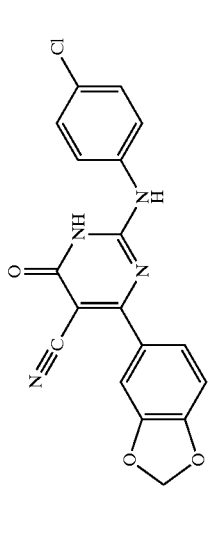 |
| --- | --- |
| 23 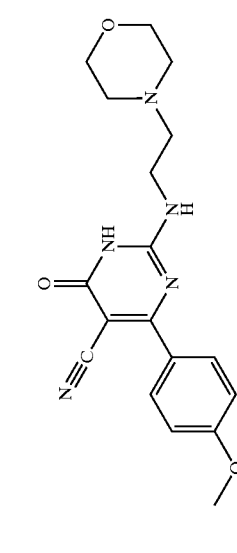 | 24 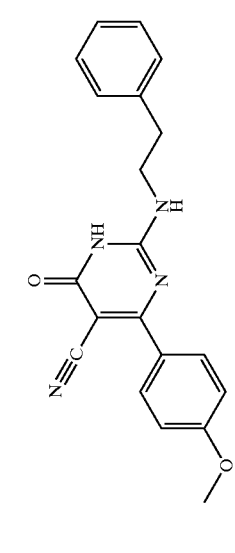 |
| 25 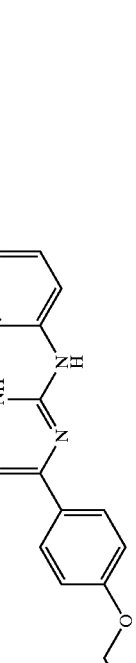 | 26 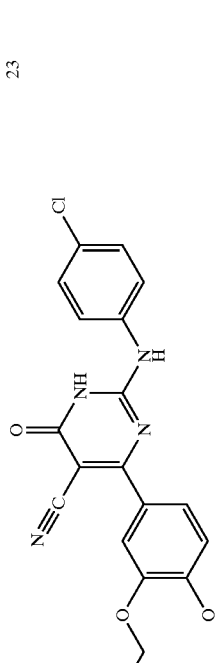 |
| 27 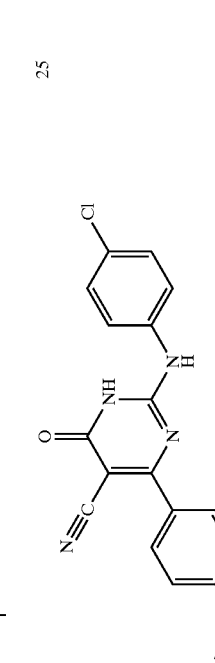 | 28 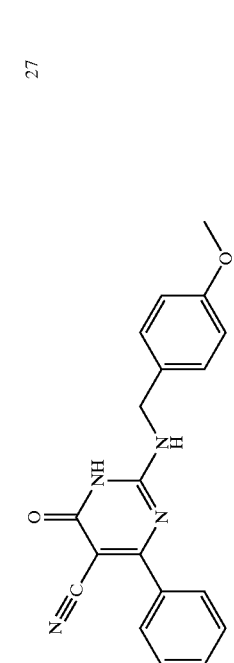 |

TABLE 1-continued

TABLE 1-continued
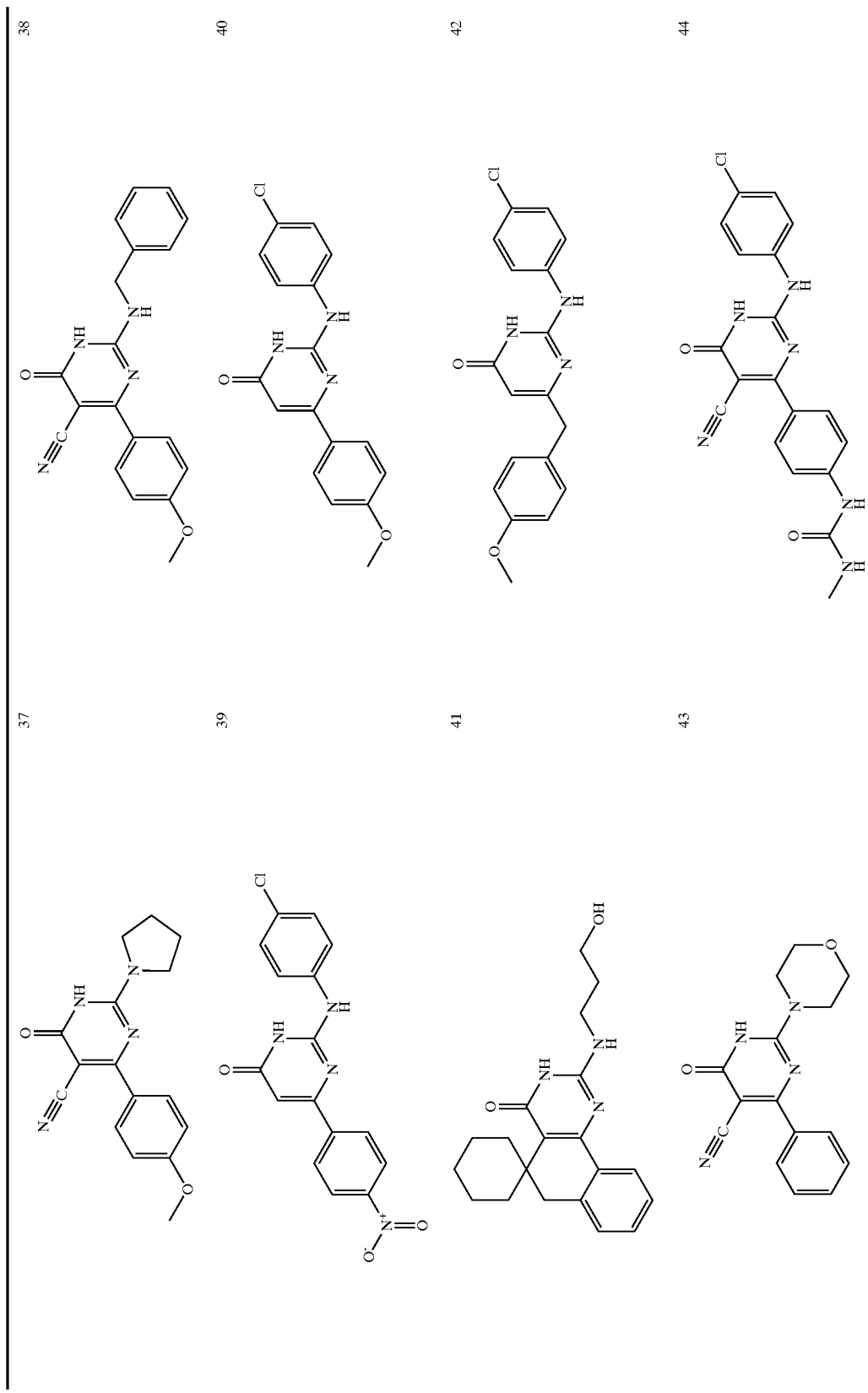

TABLE 1-continued
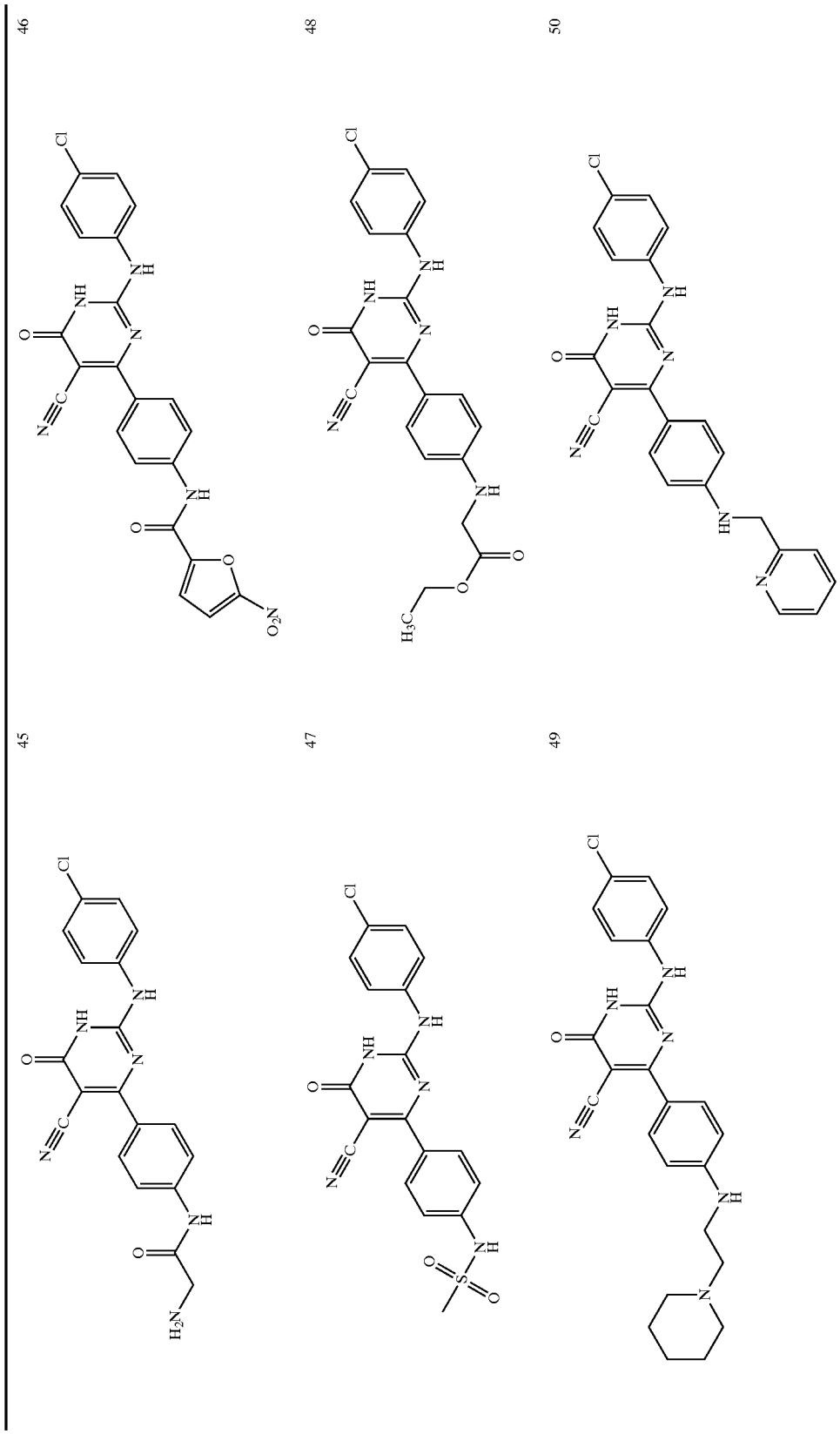

TABLE 1-continued
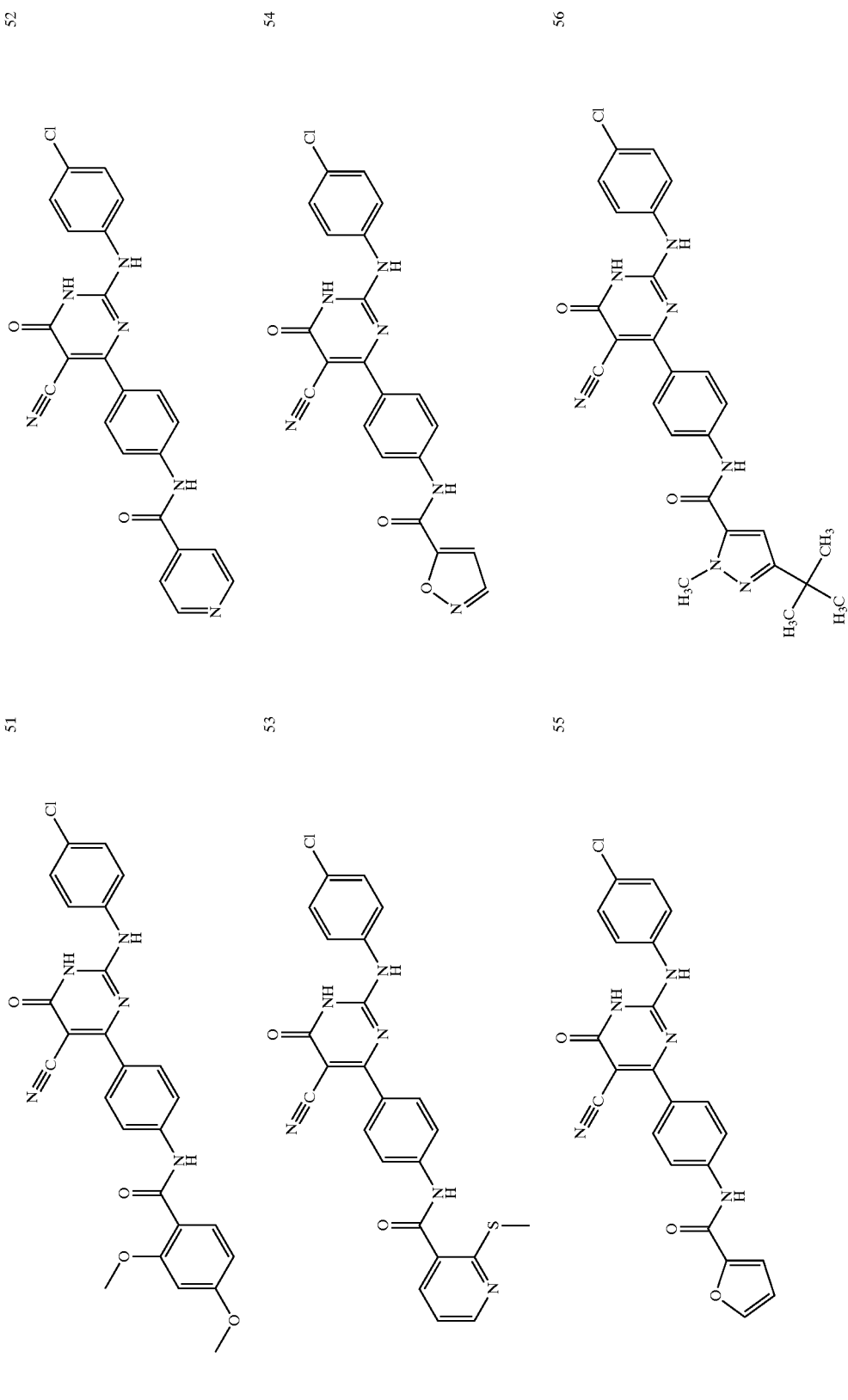

TABLE 1-continued
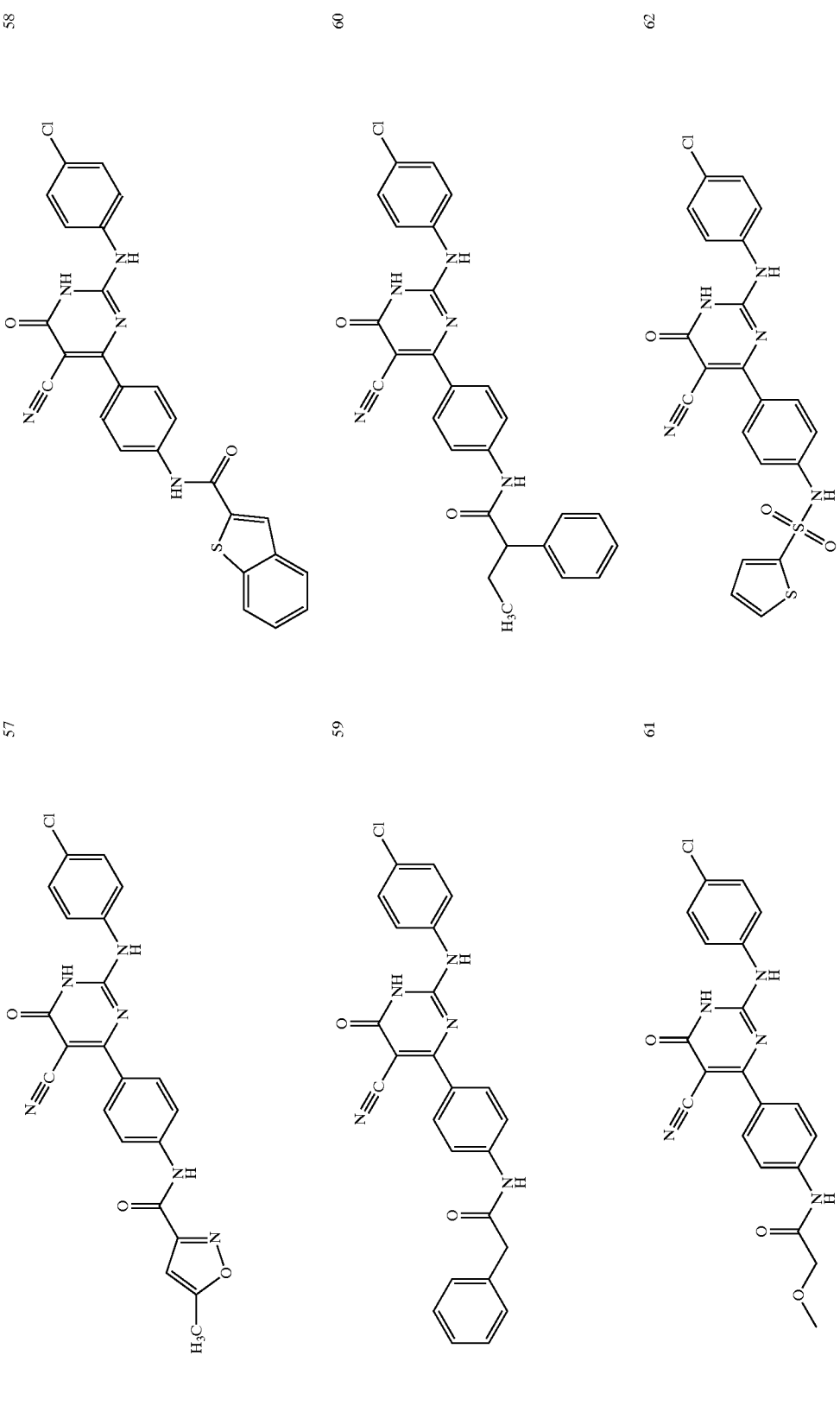

TABLE 1-continued
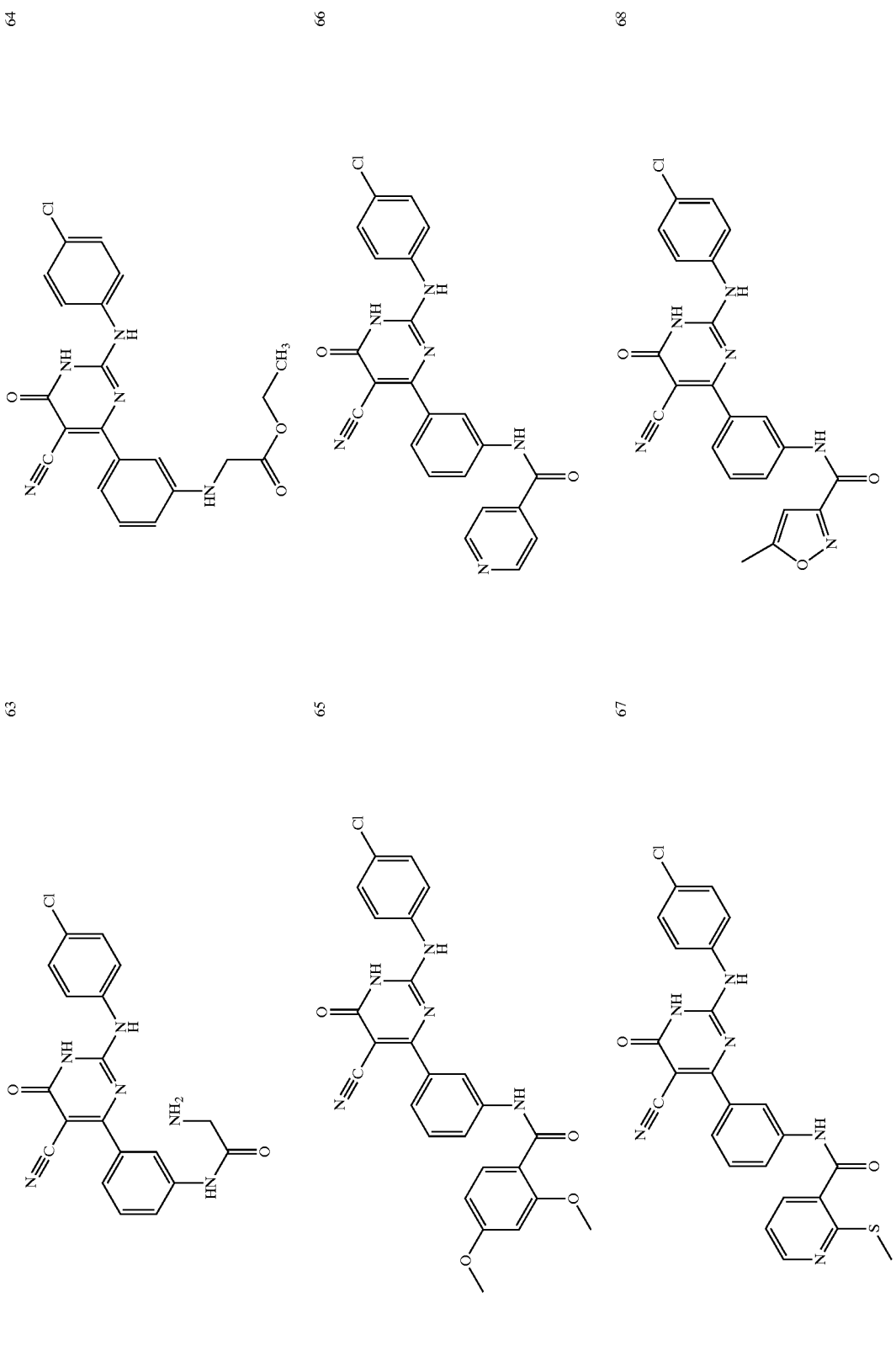

TABLE 1-continued
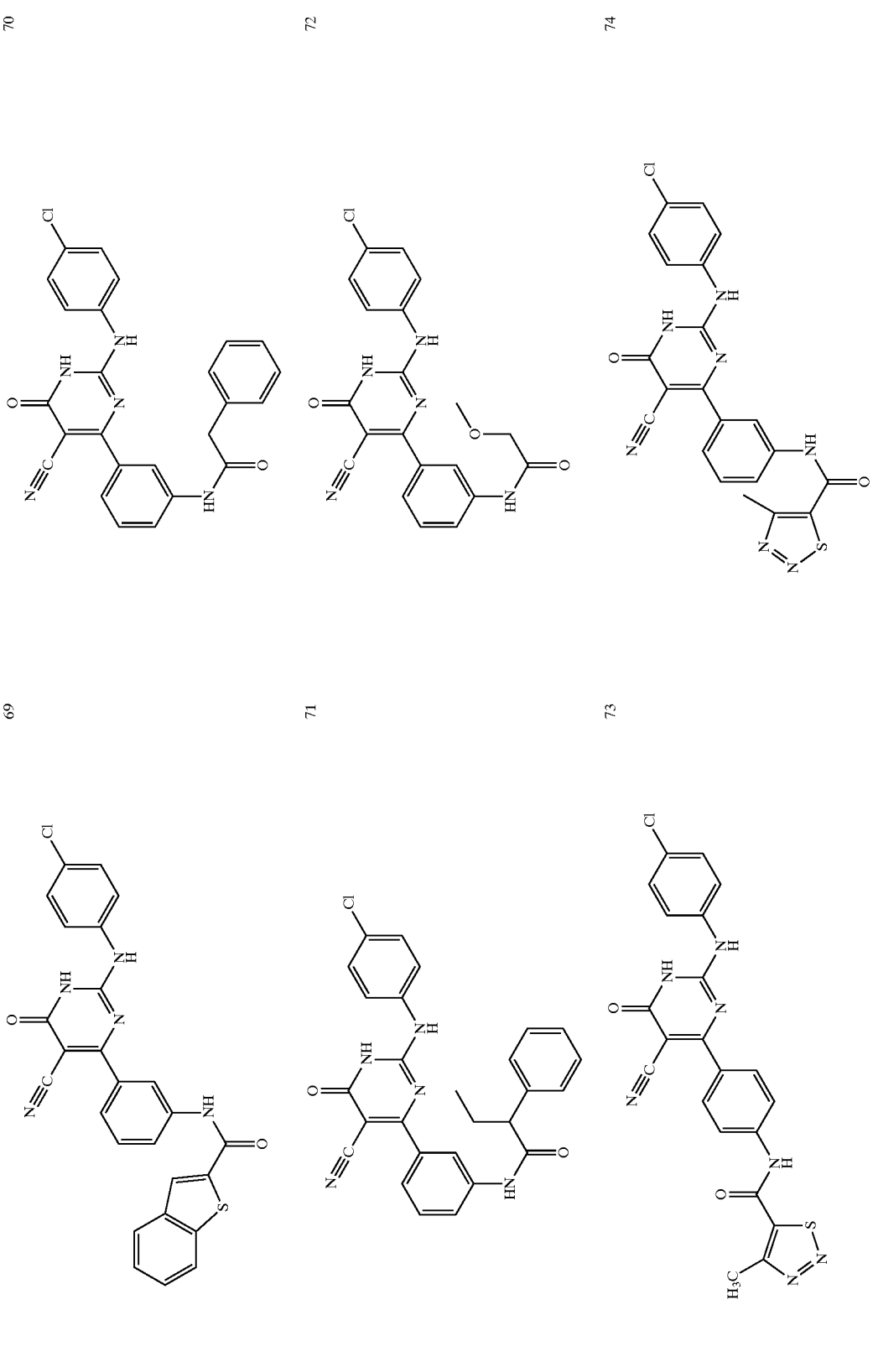

TABLE 1-continued
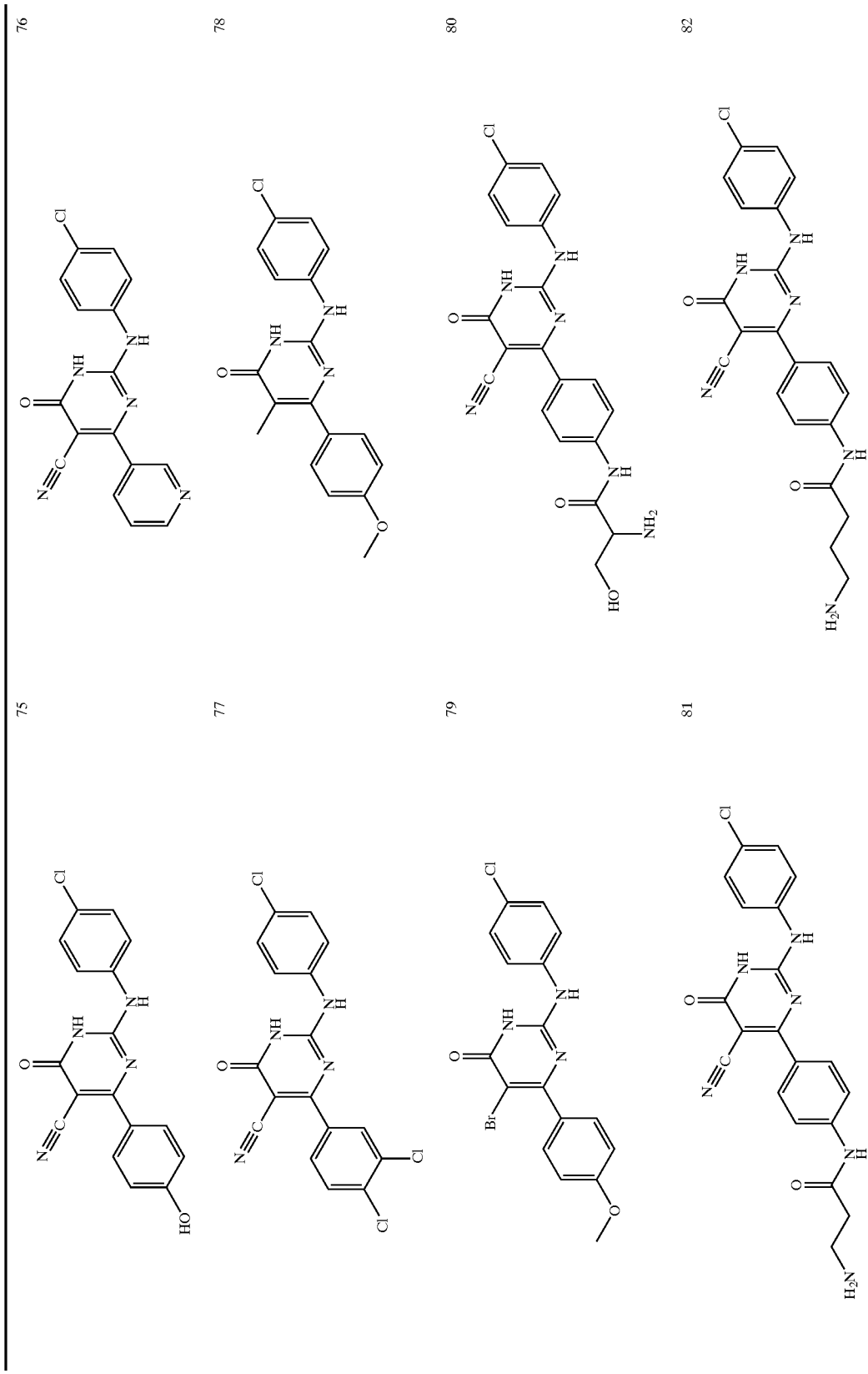

TABLE 1-continued
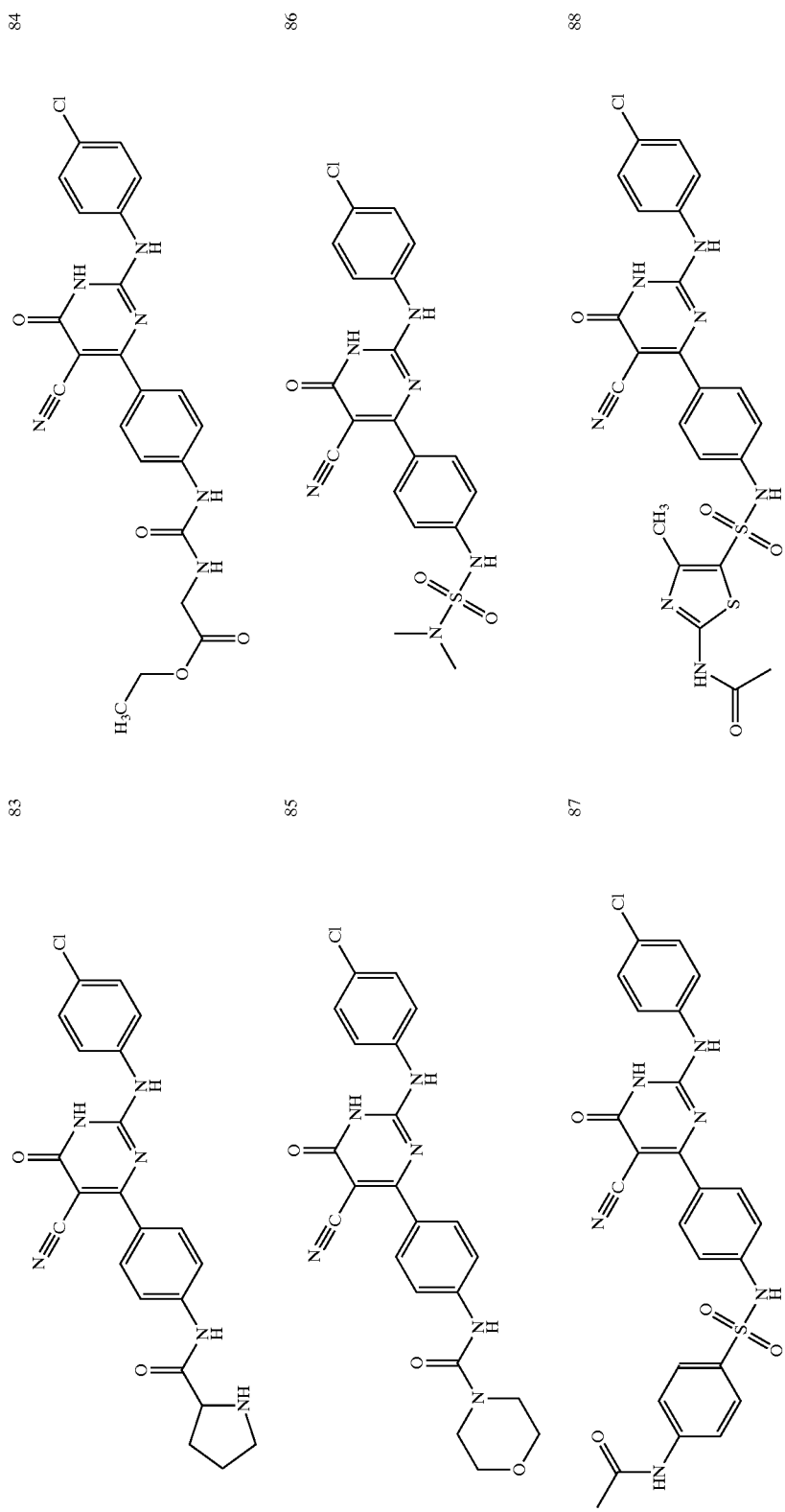

TABLE 1-continued
89
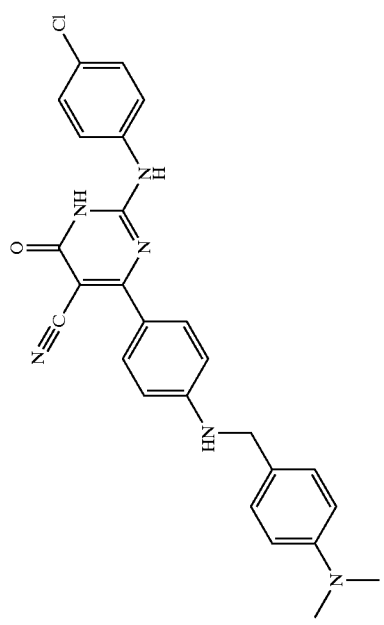
90
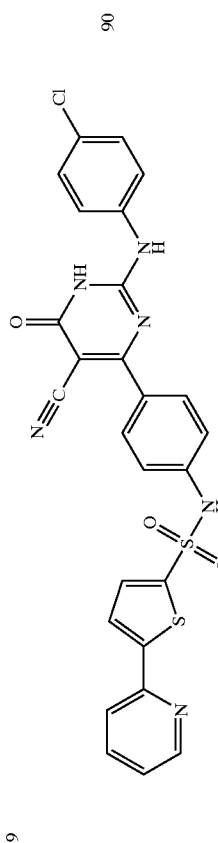
91
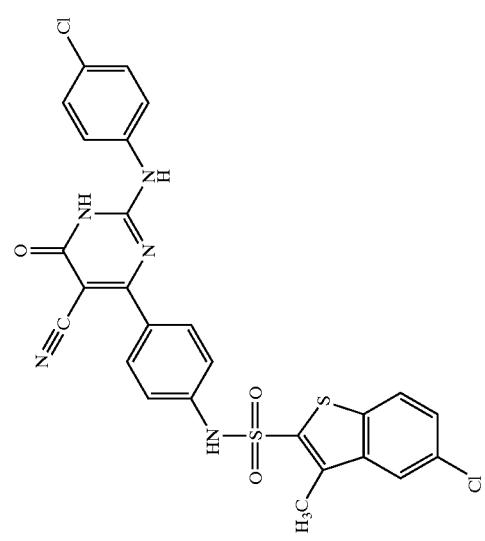
92
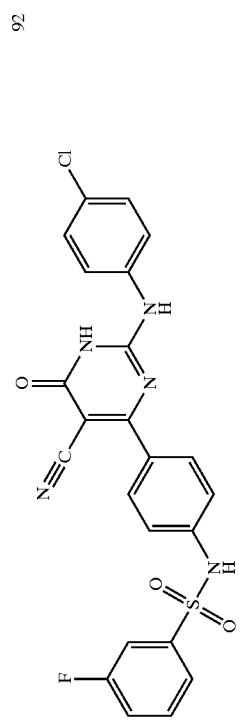

TABLE 1-continued

TABLE 1-continued
| 99 | 100 |
|---|---|
| 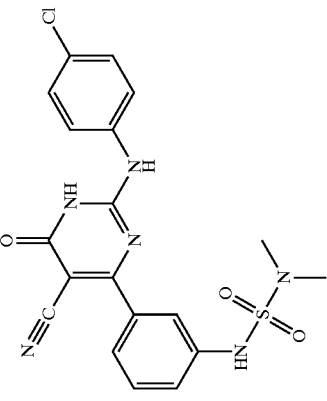 | 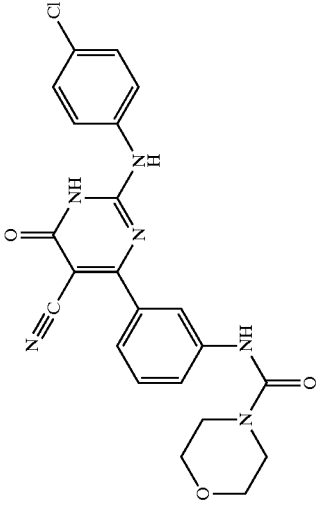 |
| 101 | 102 |
| 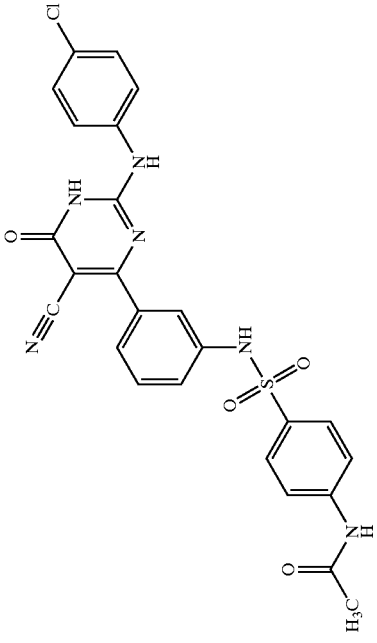 | 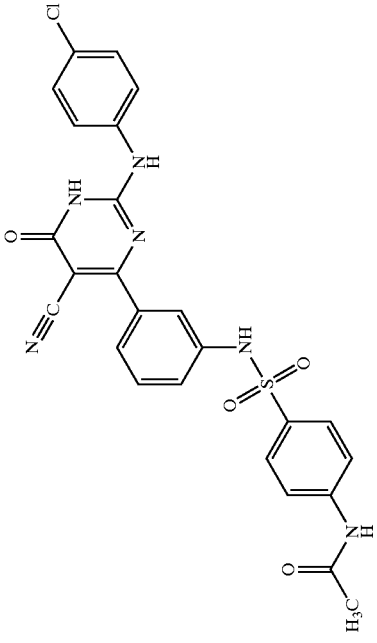 |

TABLE 1-continued
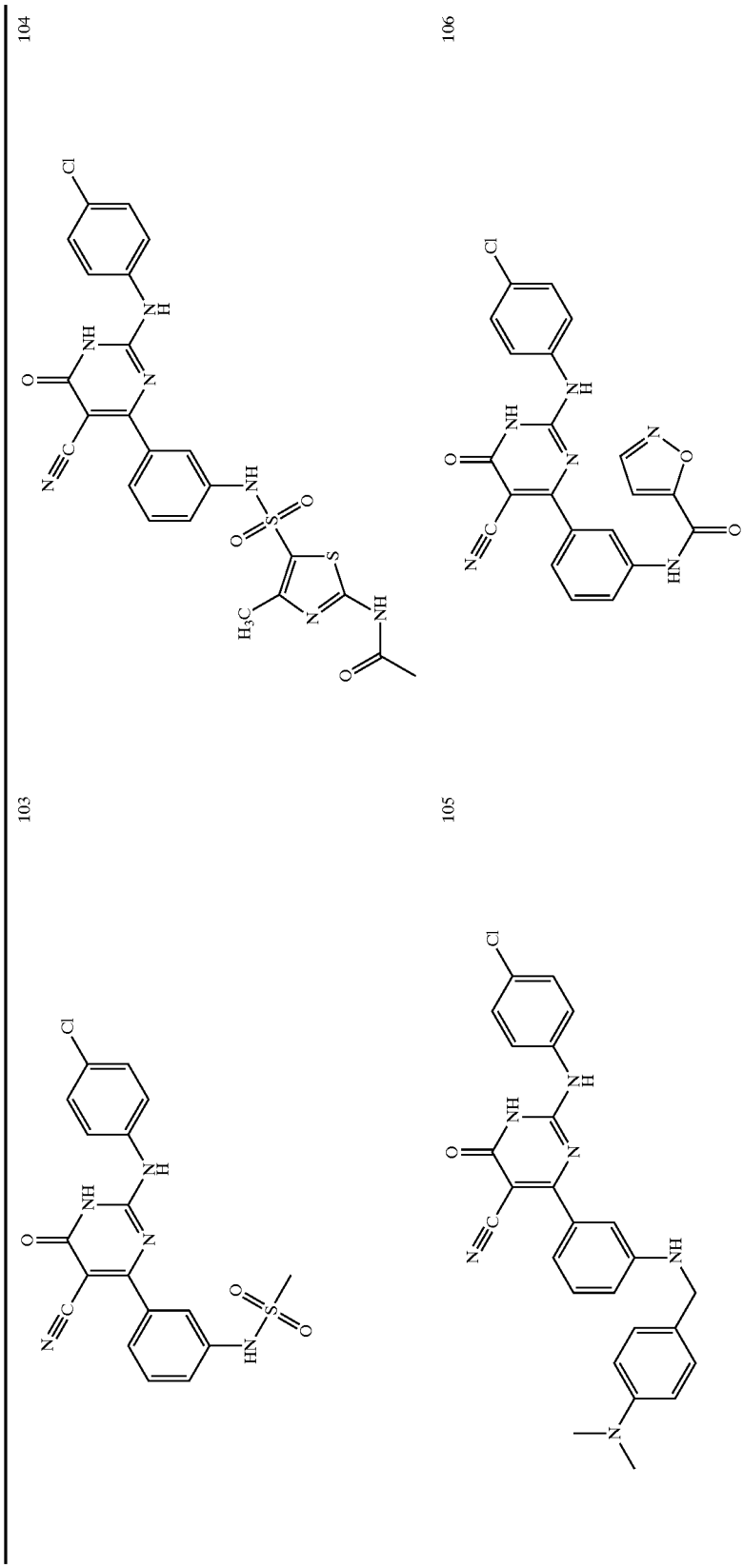

TABLE 1-continued
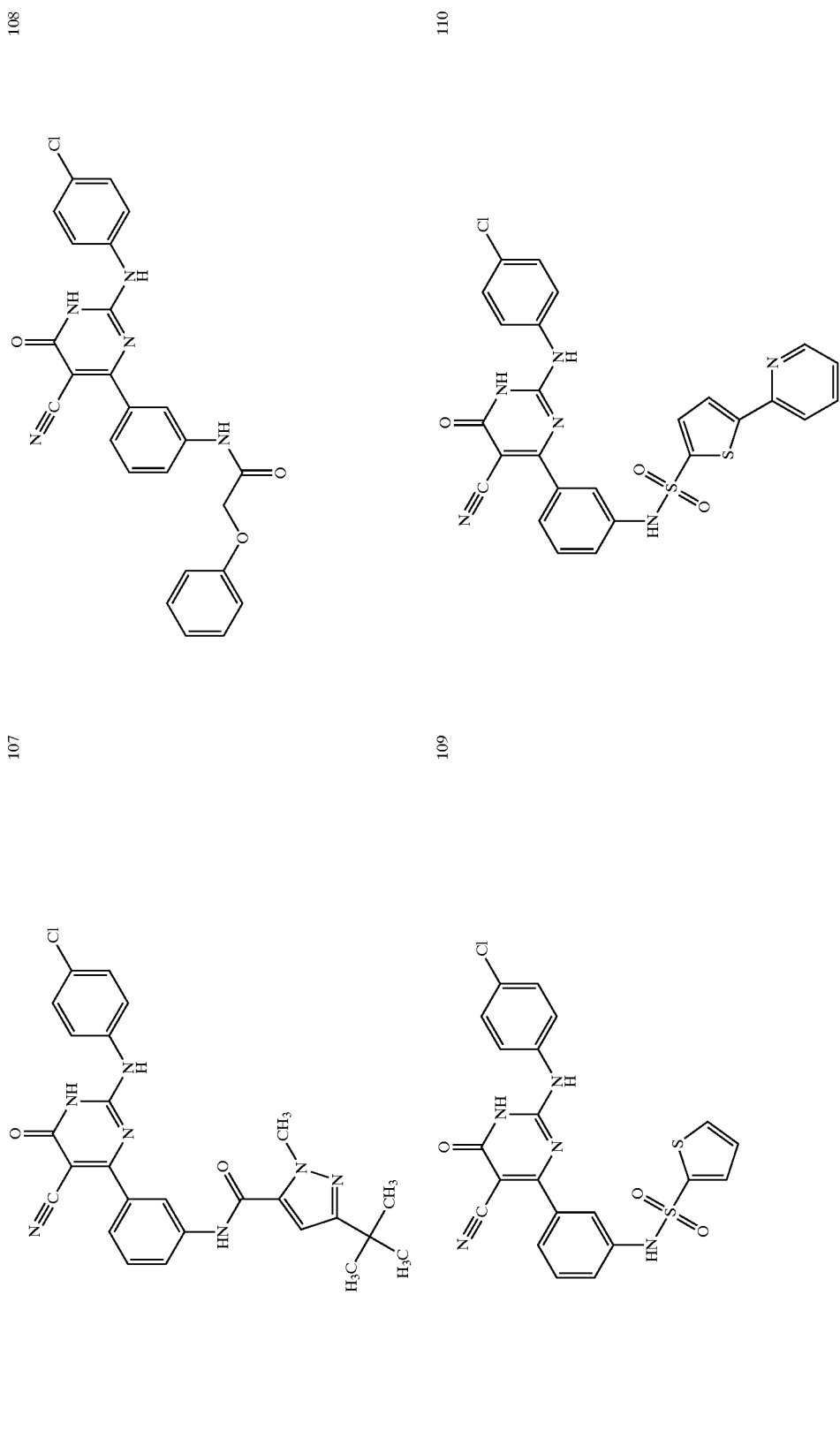

TABLE 1-continued
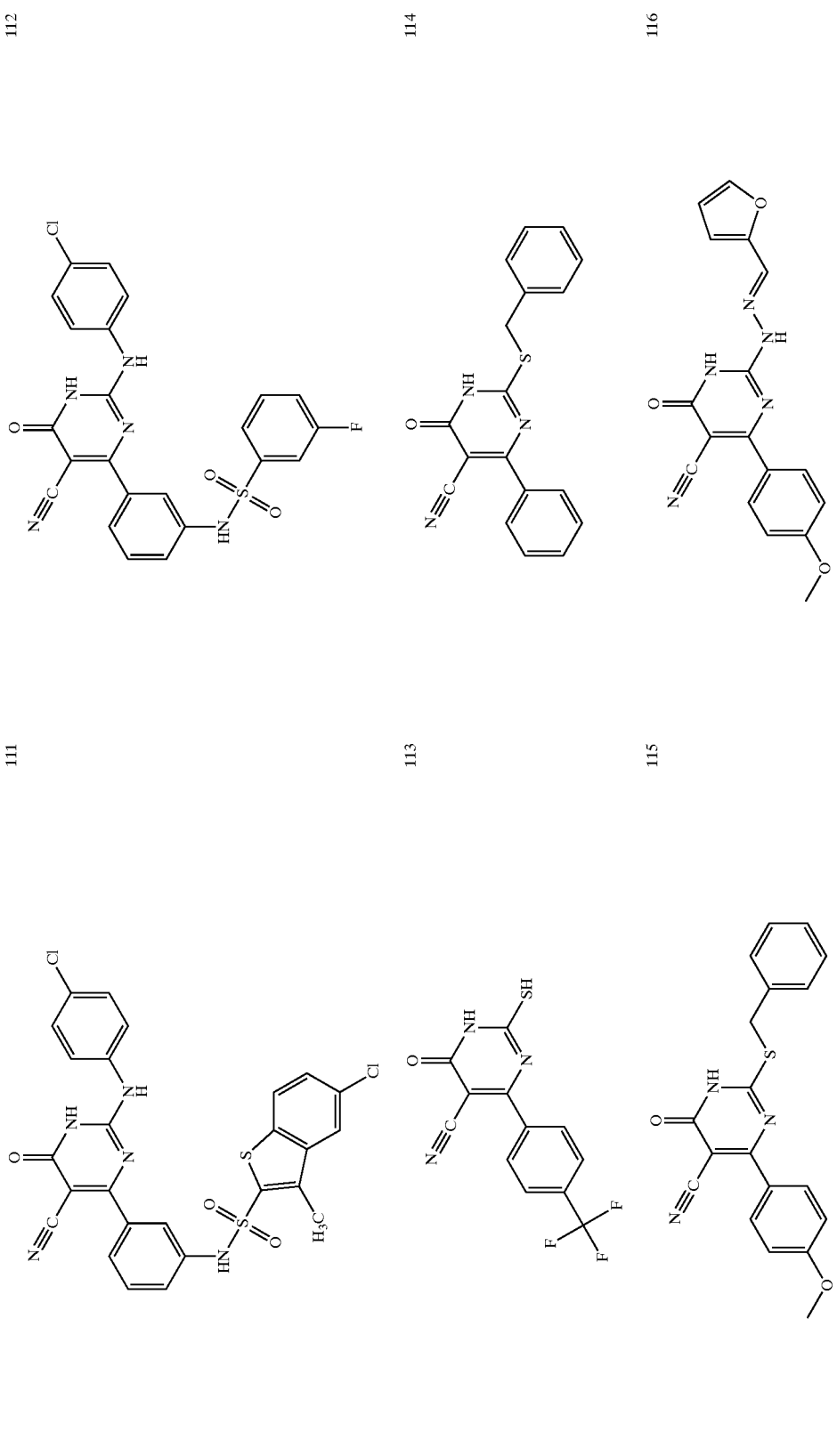

TABLE 1-continued

| | |
|---|---|
| 117 | 118 |
| 119 | 120 |
| 121 | 122 |
| 123 | 124 |

TABLE 1-continued
| 125 | 126 |
|---|---|
| 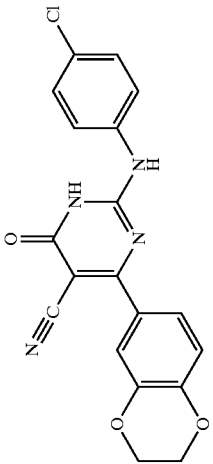 | 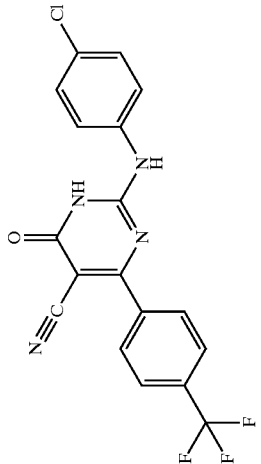 |
| 127 | 128 |
|---|---|
| 129 | 130 |
|---|---|

TABLE 1-continued
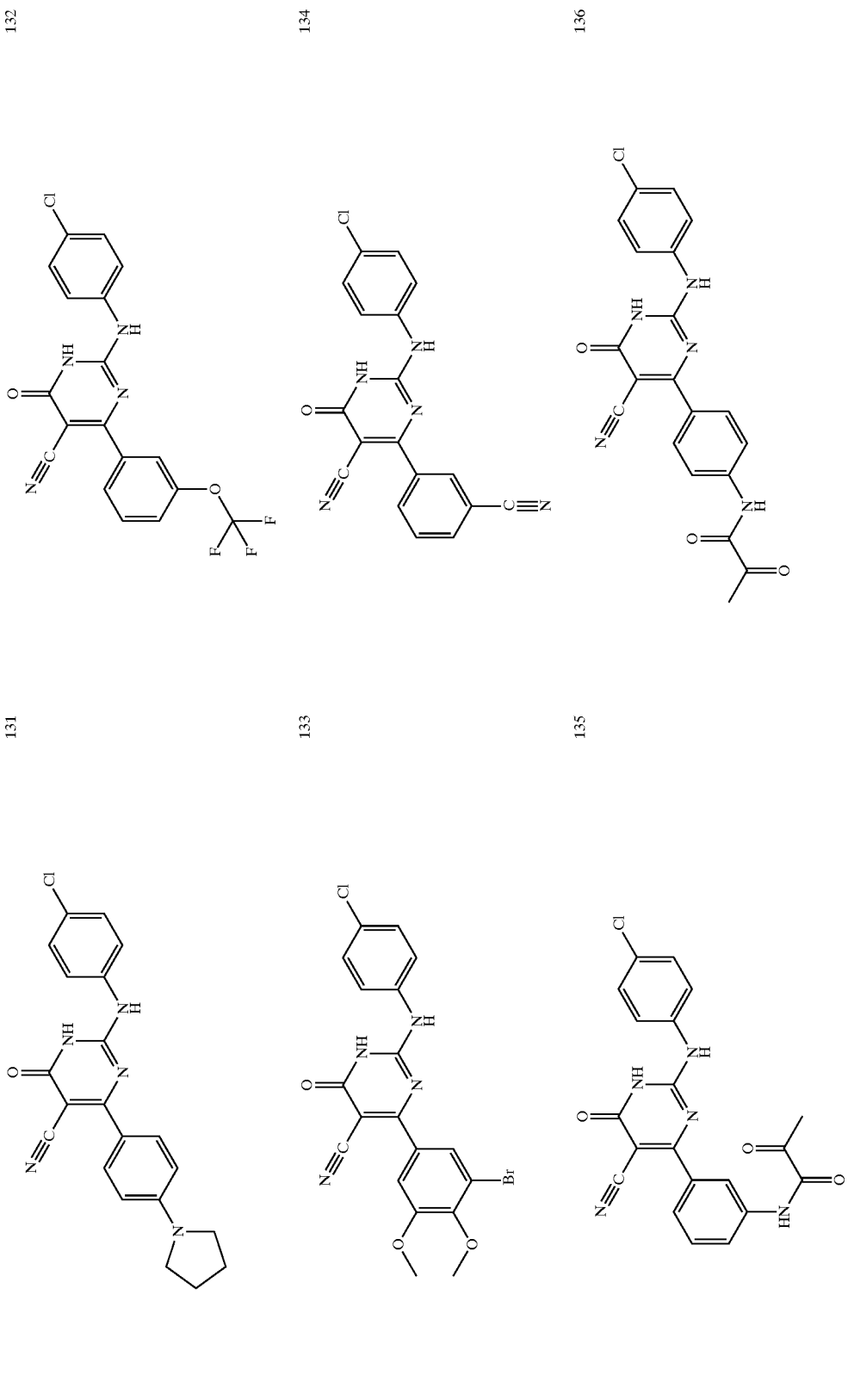

TABLE 1-continued
| 137 | 138 |
|---|---|
| 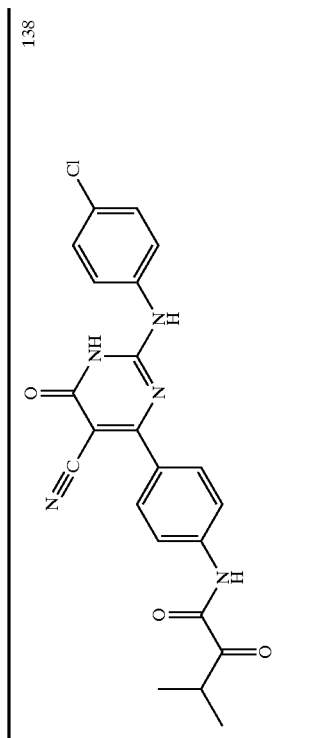 | 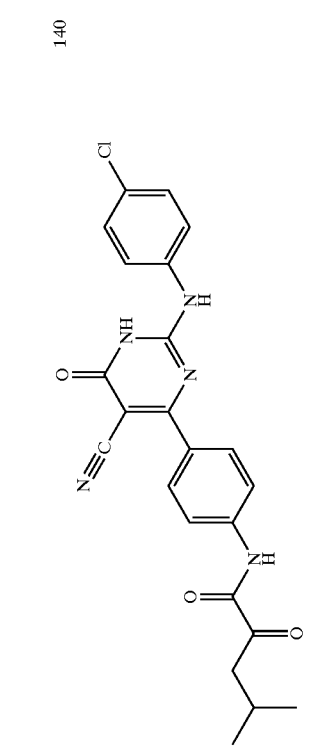 |
| 139 | 140 |
|---|---|
| 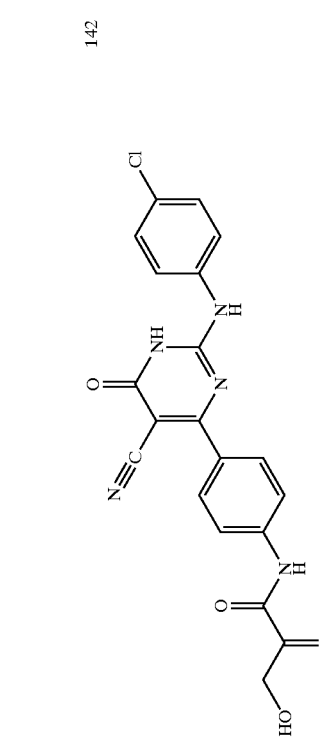 |  |
| 141 | 142 |
|---|---|
| 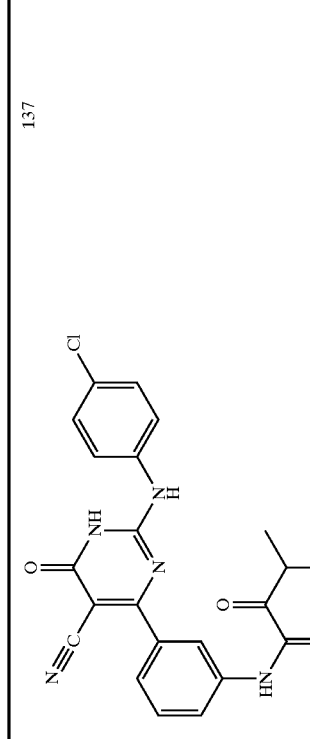 | 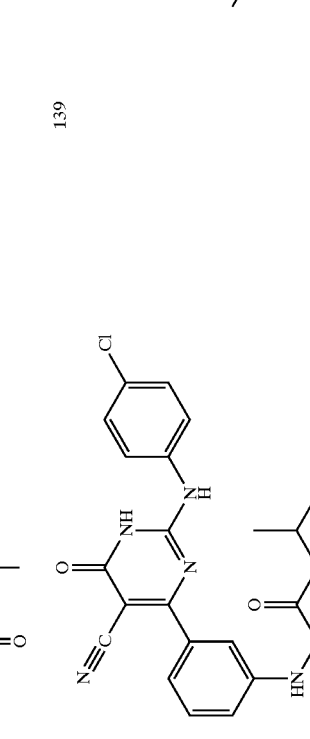 |

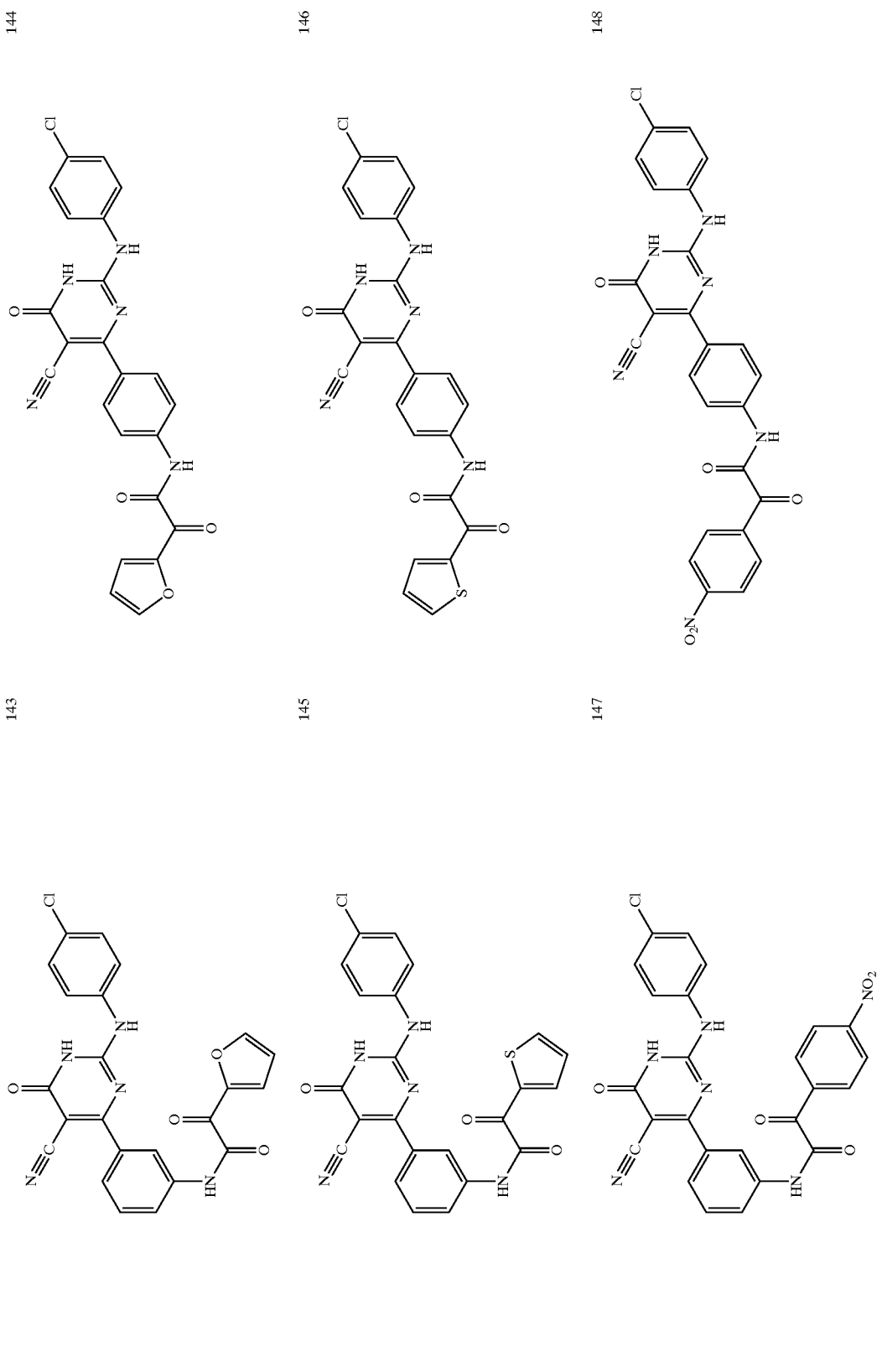

TABLE 1-continued
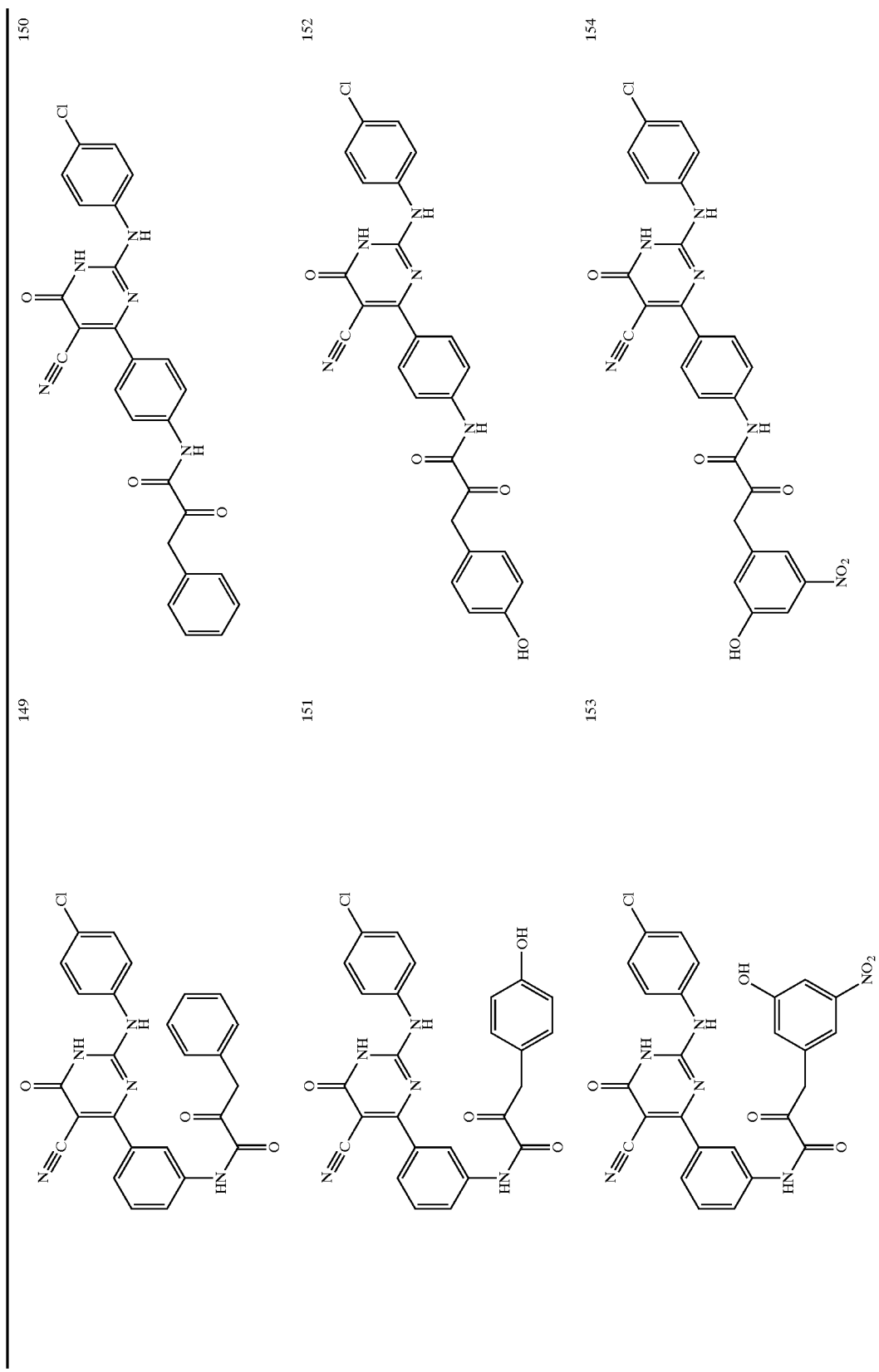

TABLE 1-continued
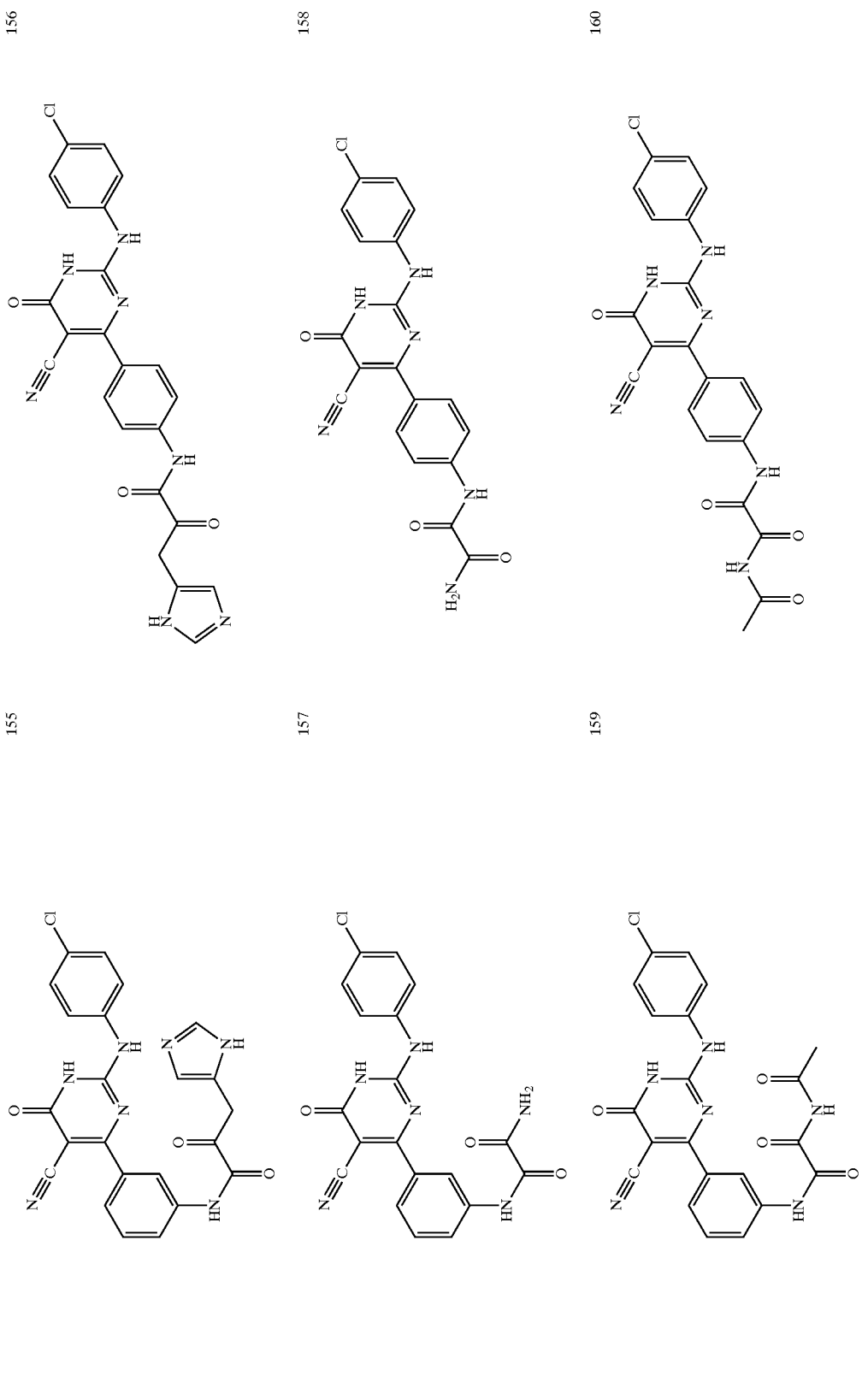

TABLE 1-continued
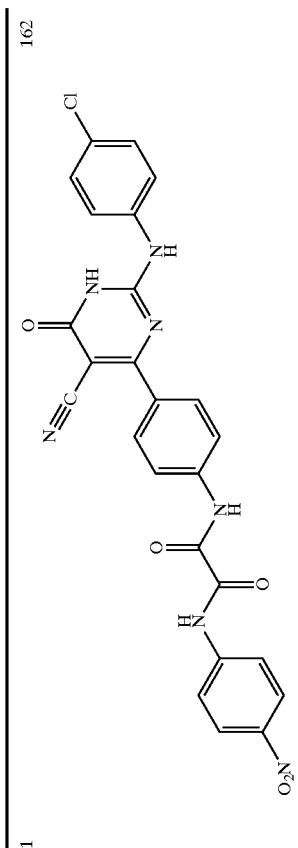

TABLE 1-continued
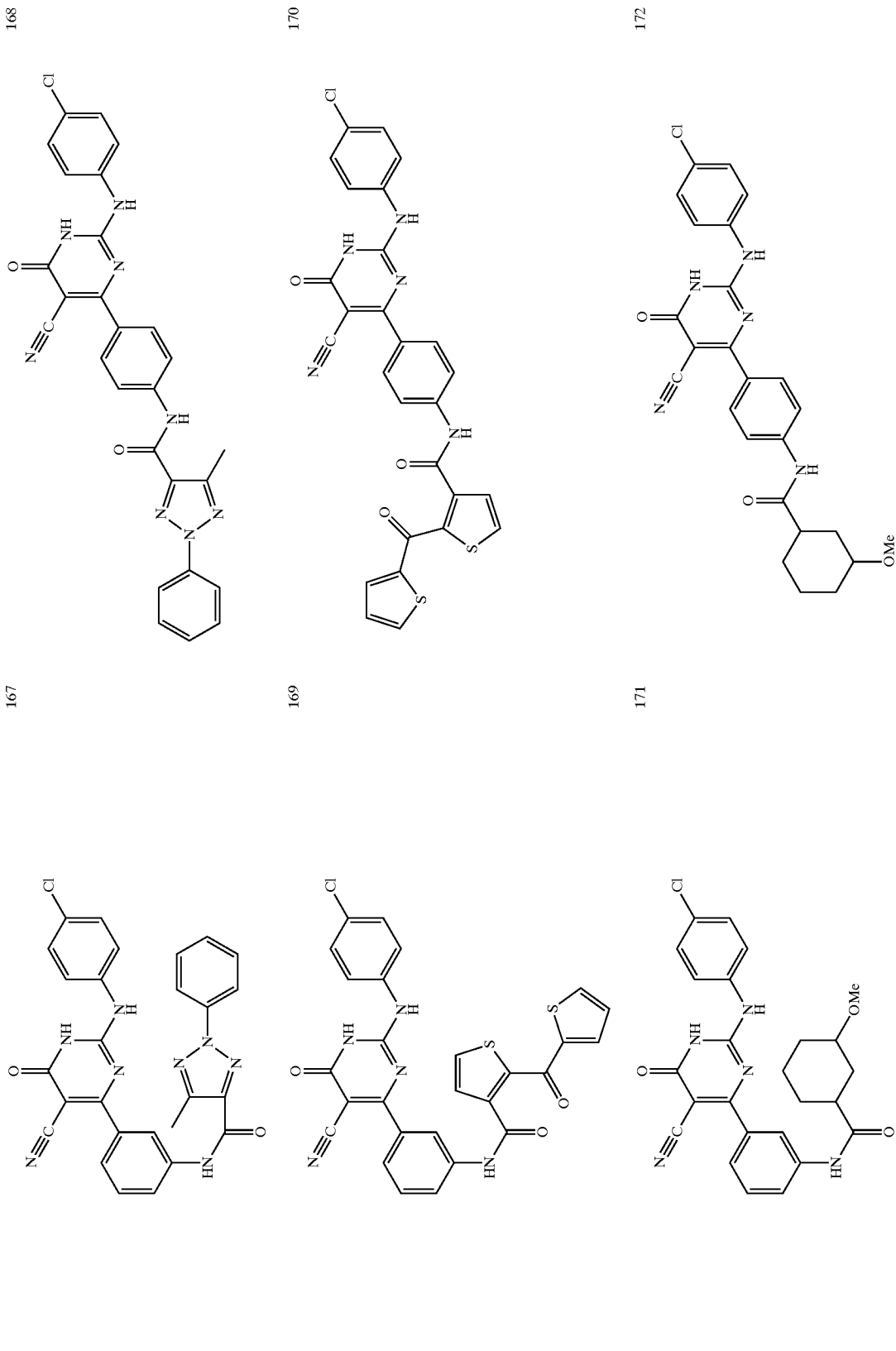

TABLE 1-continued
| 173 | 174 |
|---|---|
| 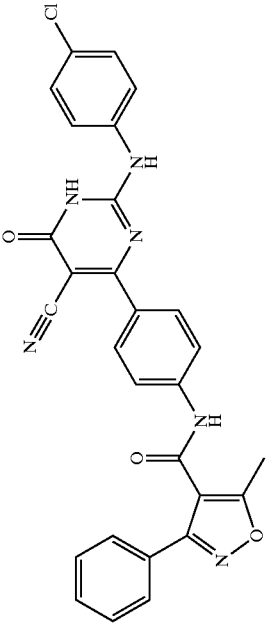 | 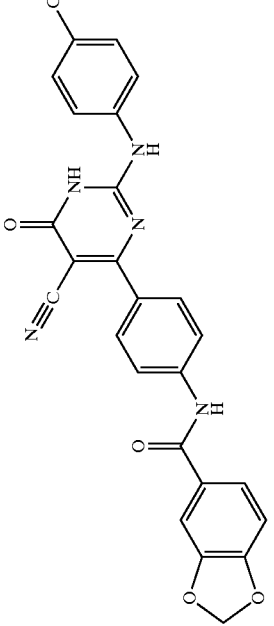 |
| 175 | 176 |
|---|---|
| 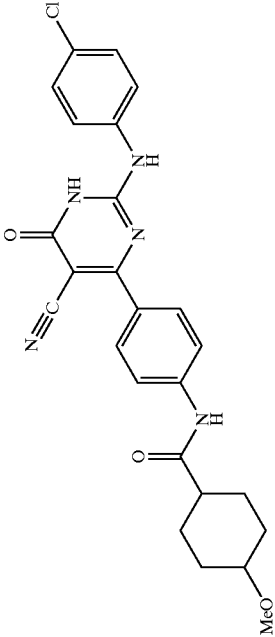 | 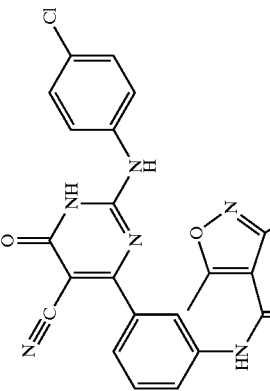 |
| 177 | 178 |
|---|---|
| 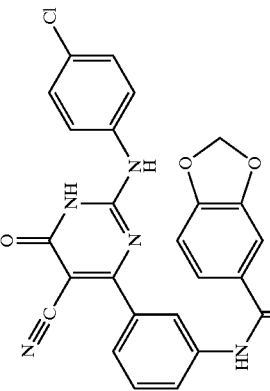 | 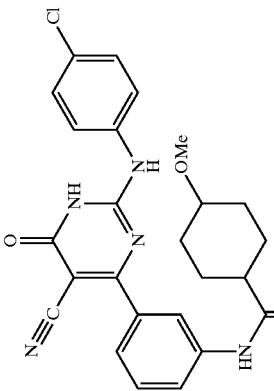 |

TABLE 1-continued

TABLE 1-continued
185
186
187
188
189
190
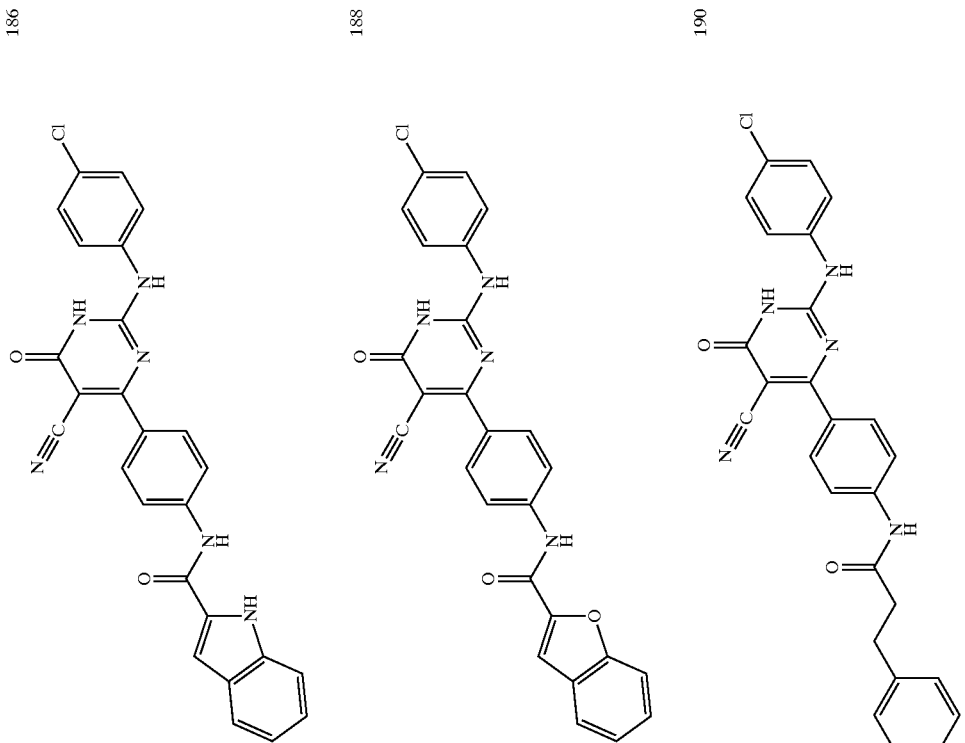
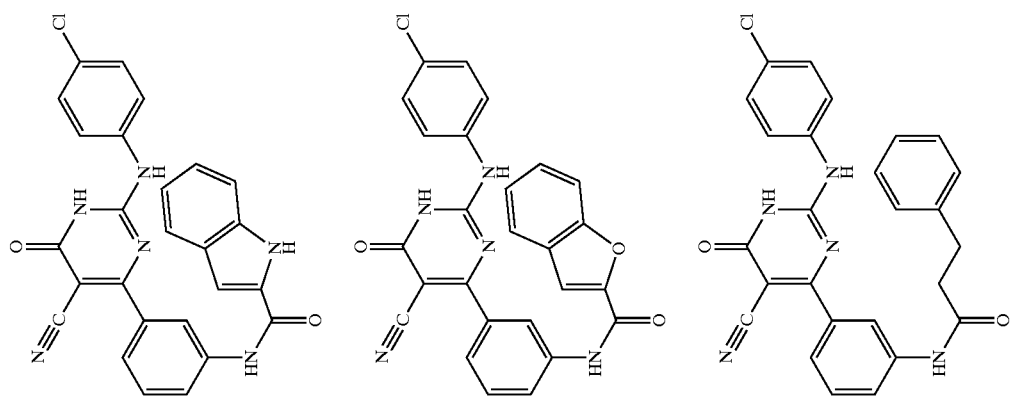

TABLE 1-continued
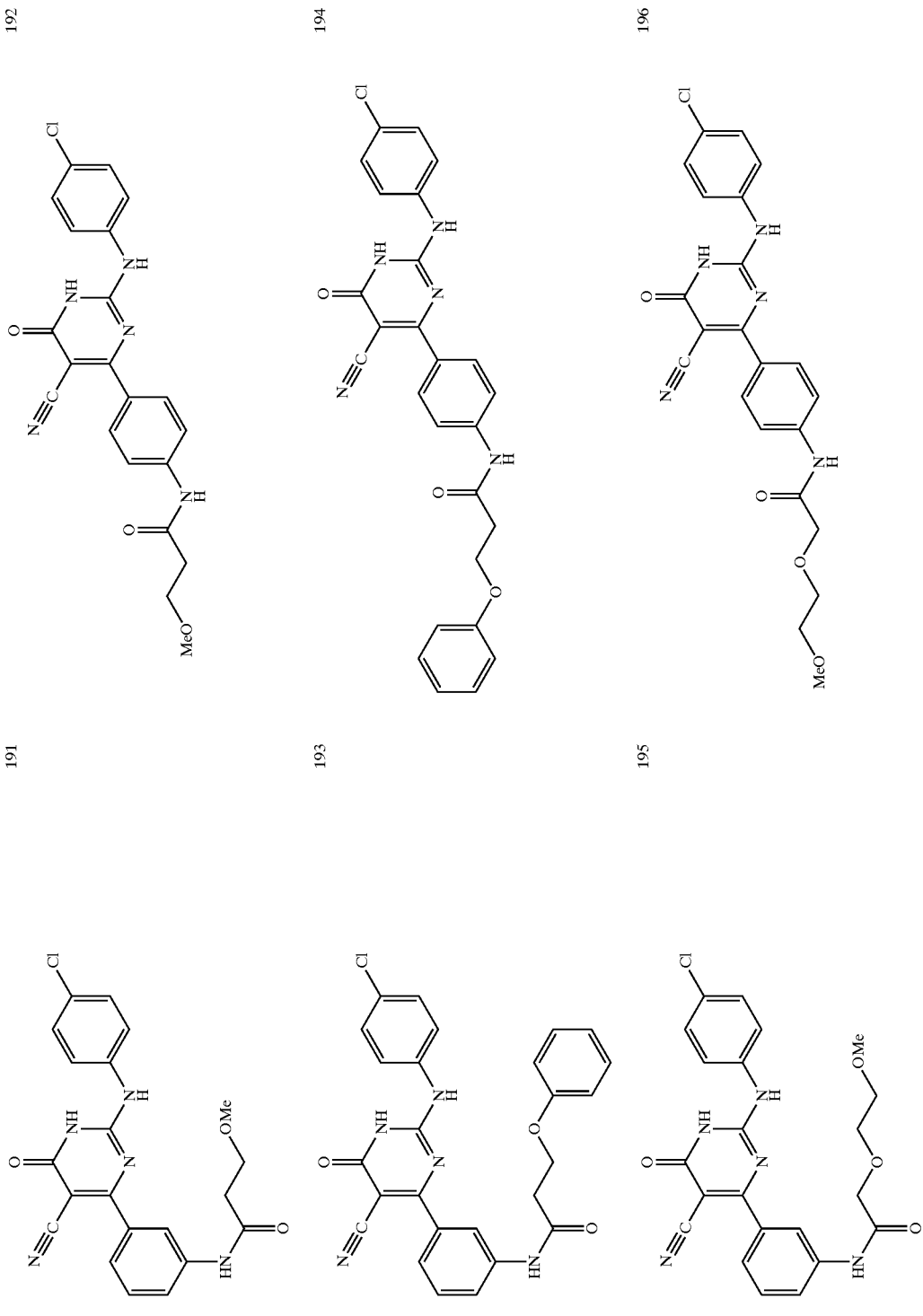

TABLE 1-continued

TABLE 1-continued
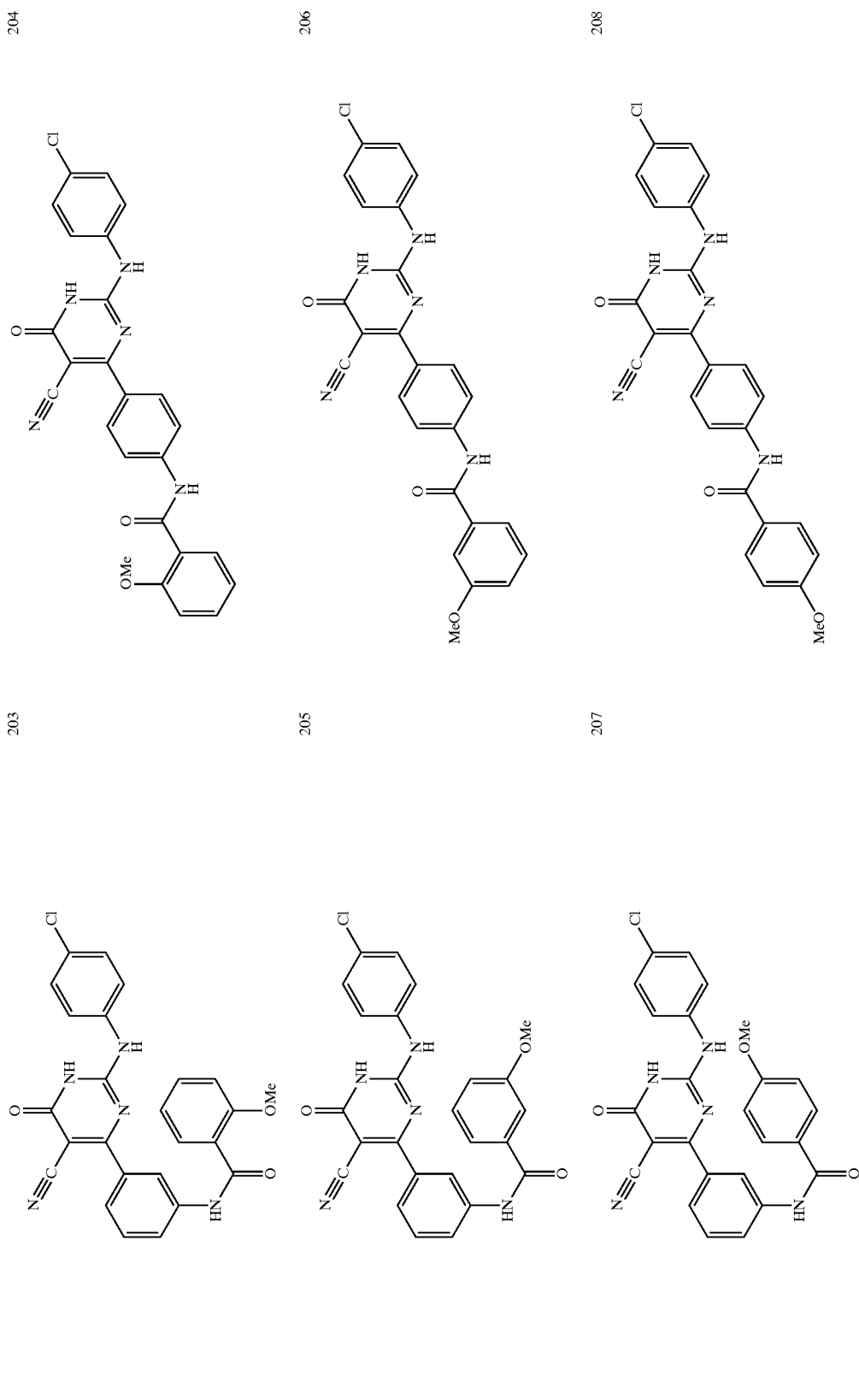

TABLE 1-continued
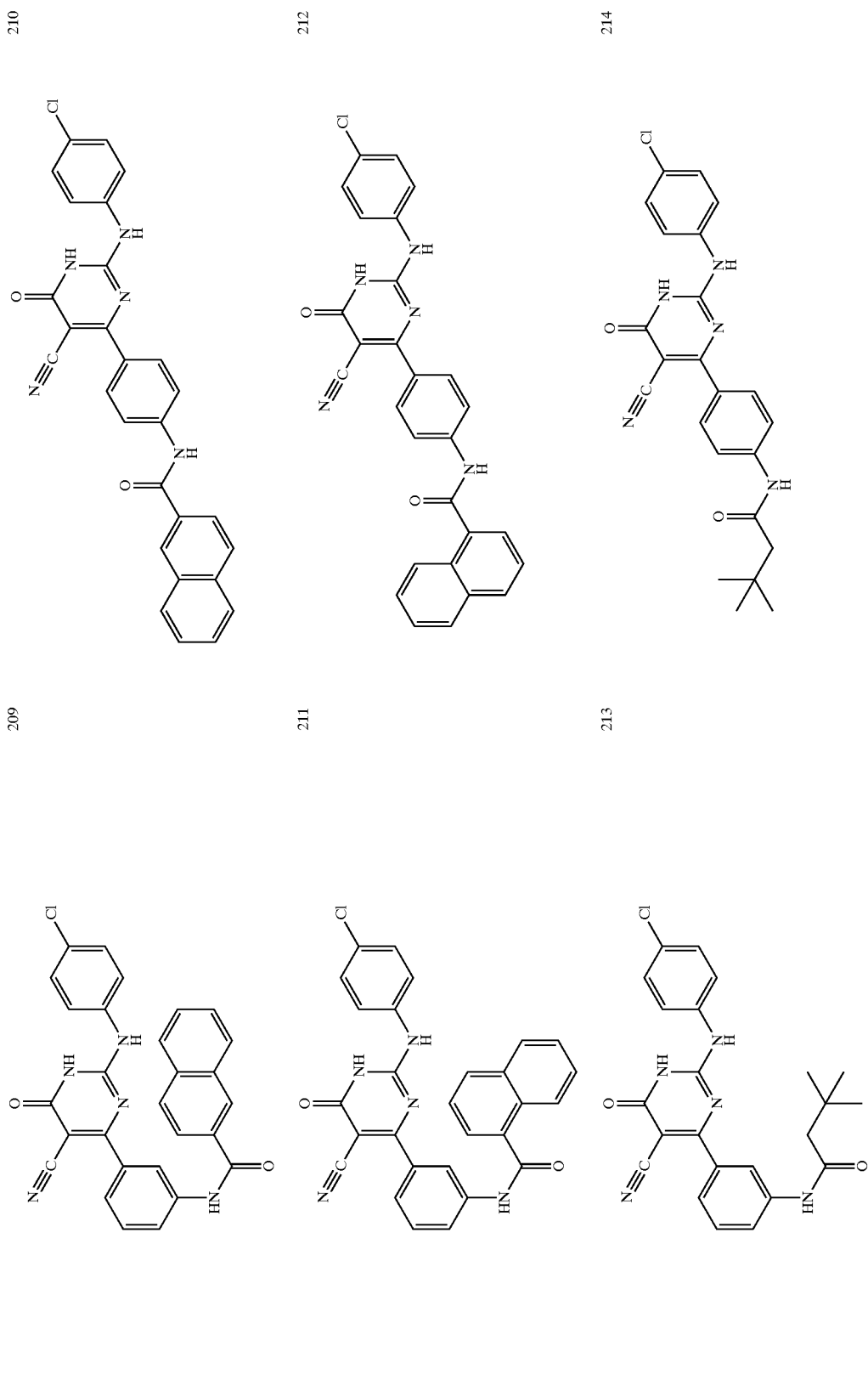

TABLE 1-continued
| 215 | 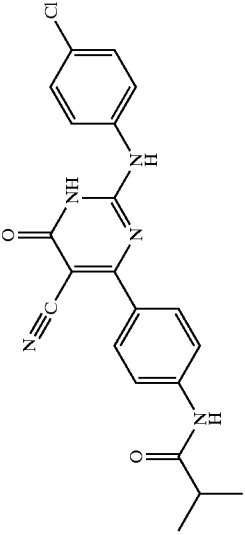 | 216 | 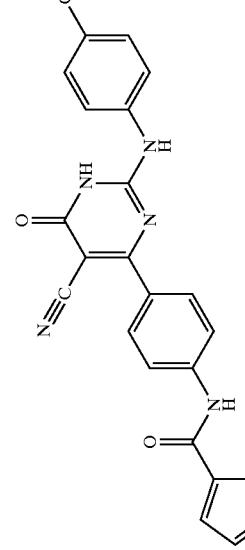 |
| --- | --- | --- | --- |
| 217 | 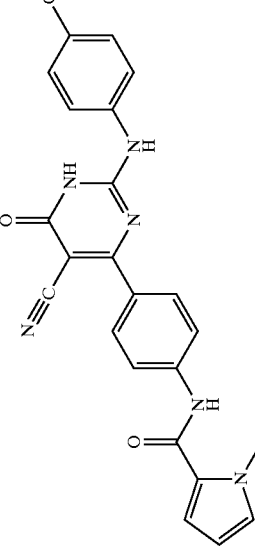 | 218 | 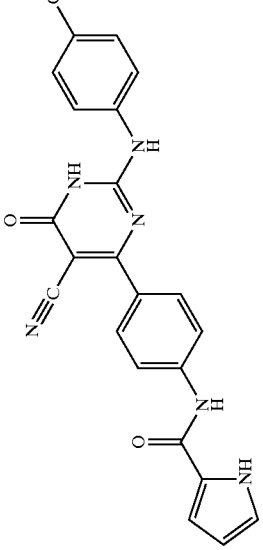 |
| 219 | 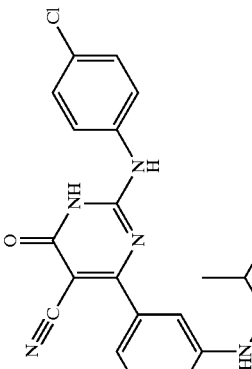 | 220 | 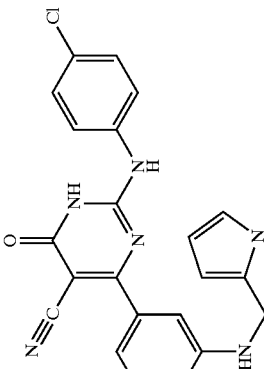 |

TABLE 1-continued
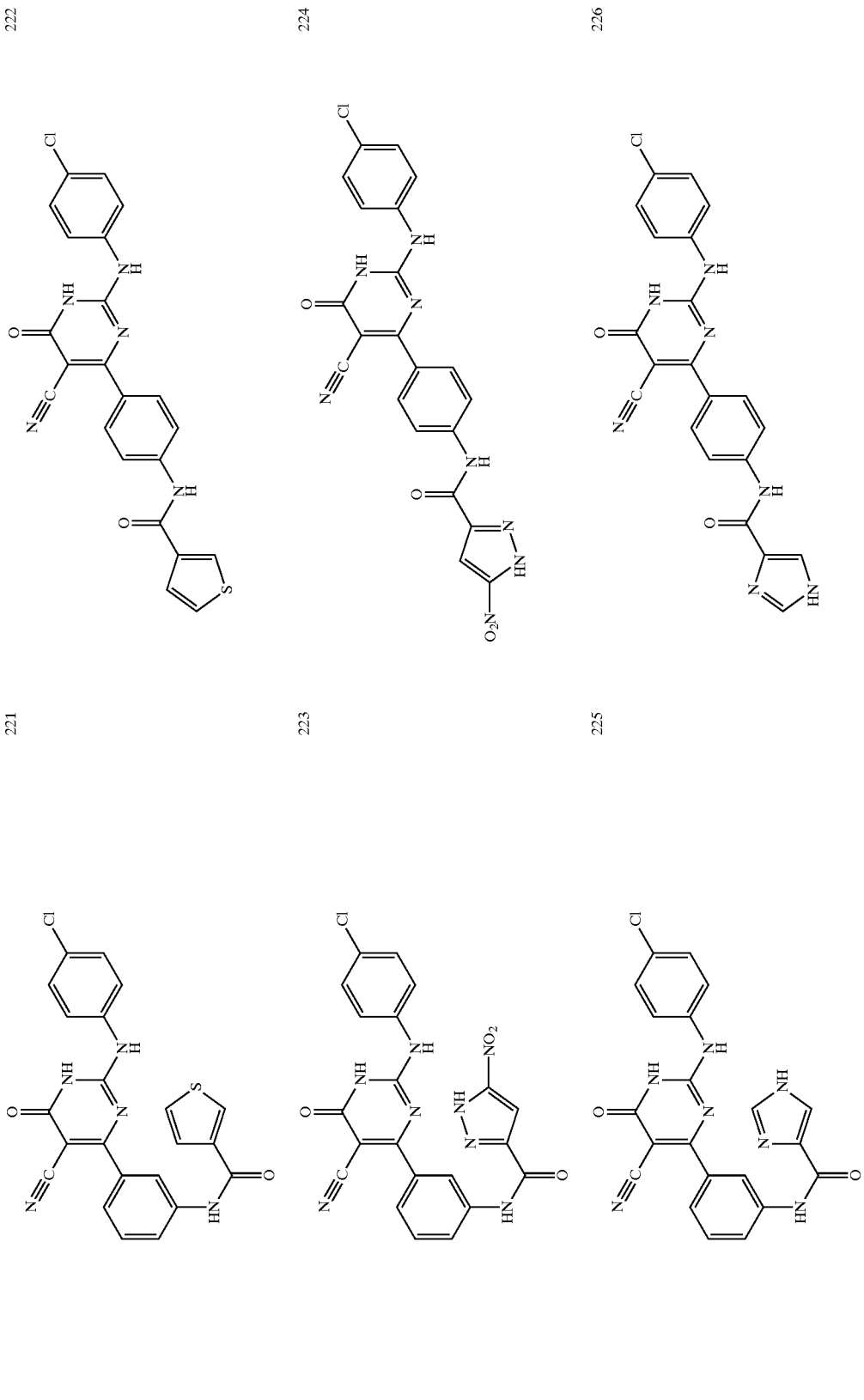

TABLE 1-continued
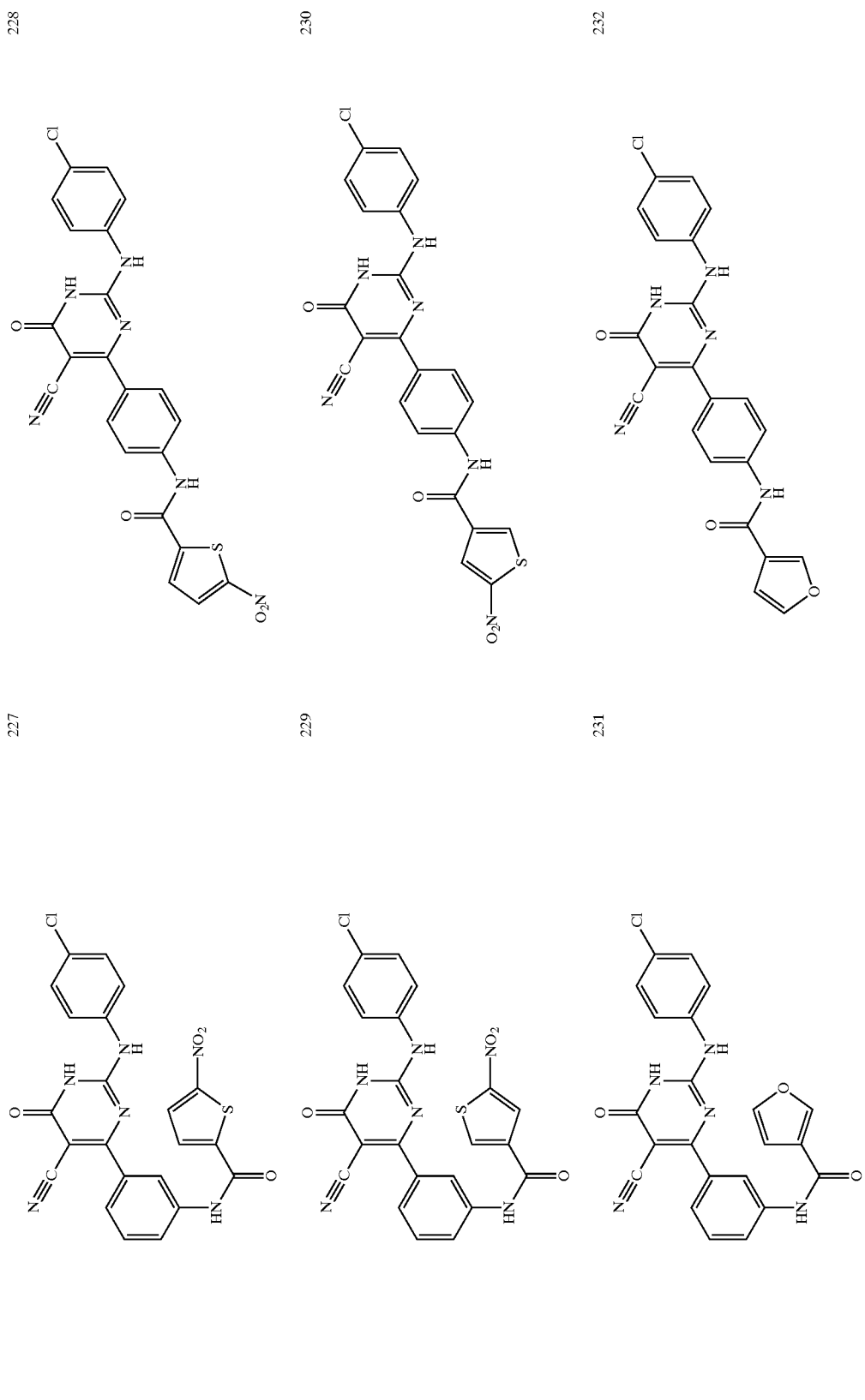

TABLE 1-continued
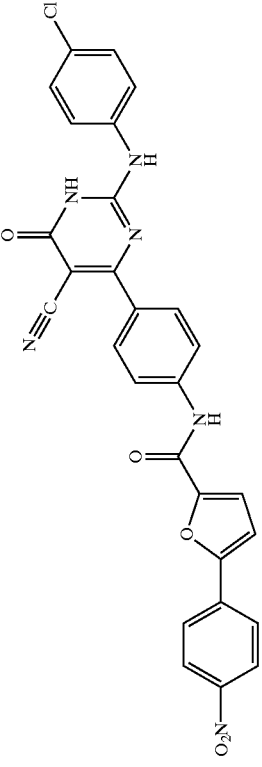

TABLE 1-continued
| 239 | 240 |
|---|---|
| 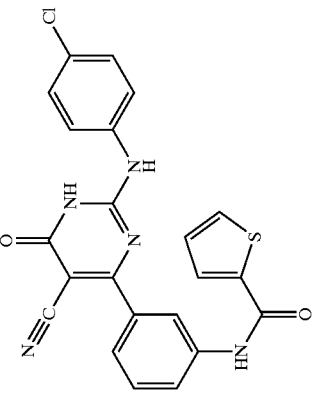 | 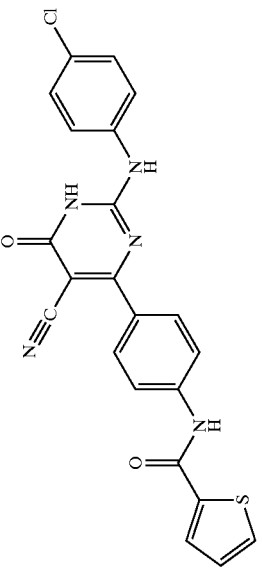 |
| 241 | 242 |
|---|---|
| 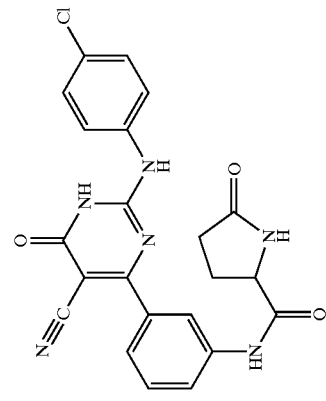 | 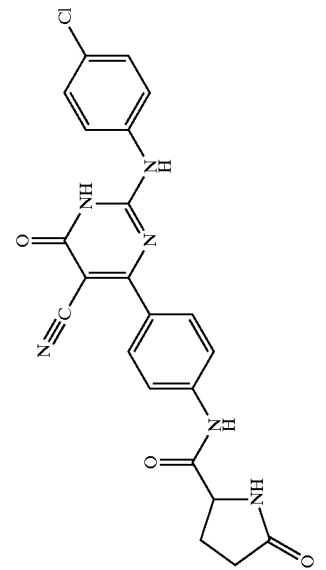 |
| 243 | 244 |
|---|---|
| 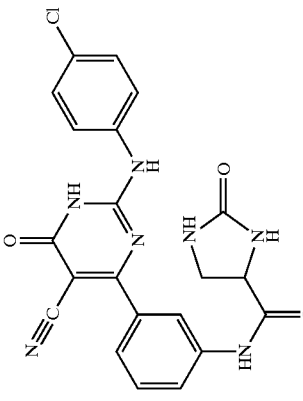 | 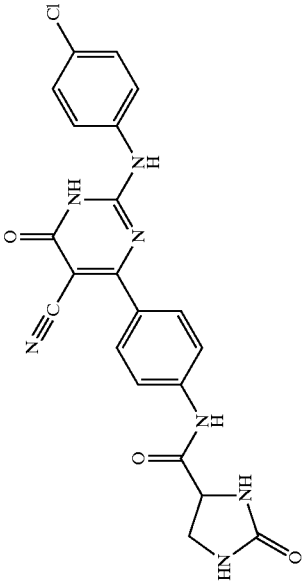 |

TABLE 1-continued
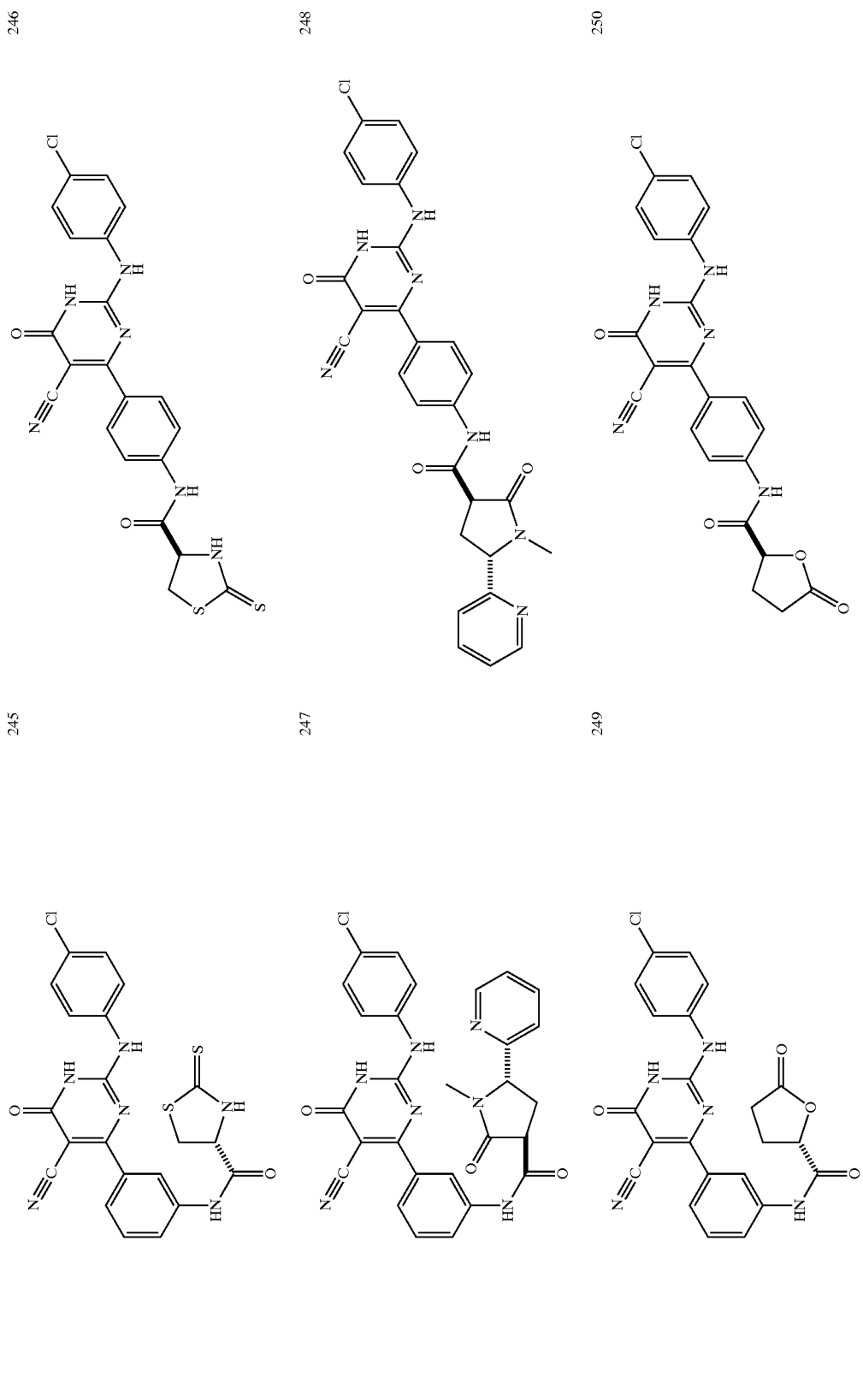

TABLE 1-continued

TABLE 1-continued

| 257 | 258 |
| 259 | 260 |
| 261 | 262 |
| 263 | 264 |

TABLE 1-continued
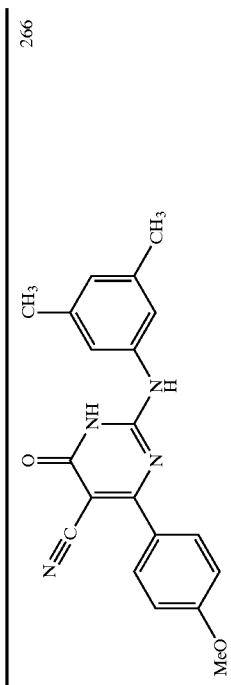

TABLE 1-continued
| 273 | 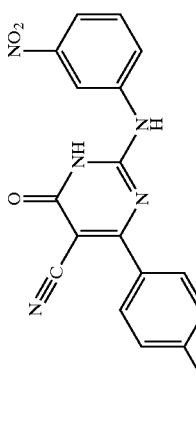 | 274 | 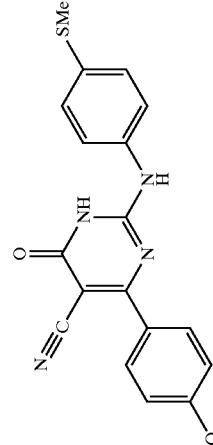 |
| 275 | 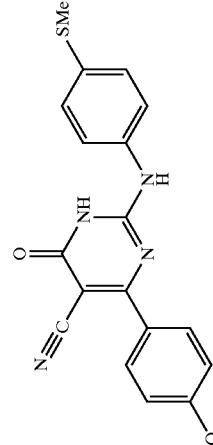 | 276 | 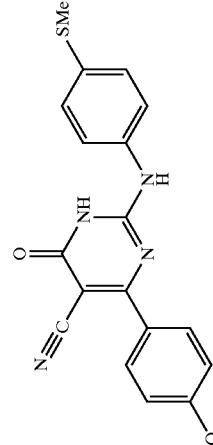 |
| 277 | 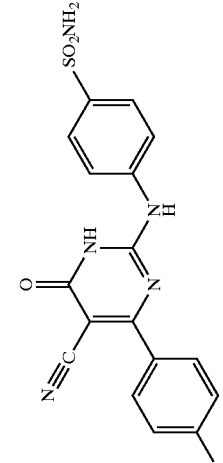 | 278 | 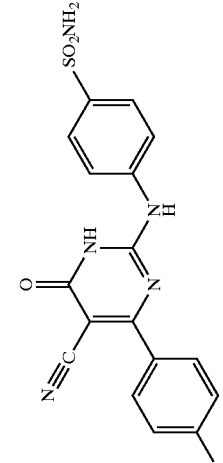 |
| 279 | 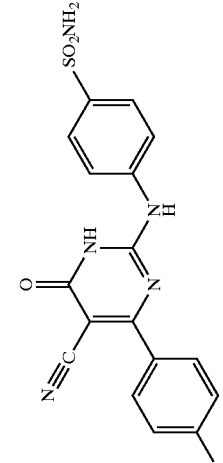 | 280 | 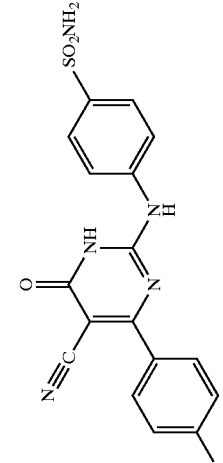 |

TABLE 1-continued
| 281 | 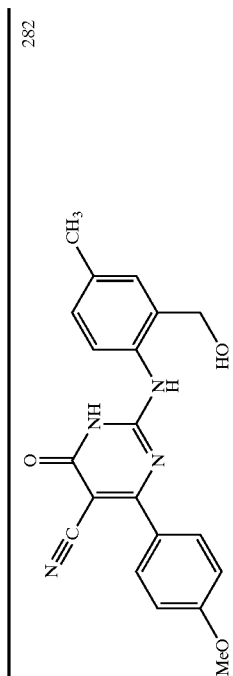 | 282 | 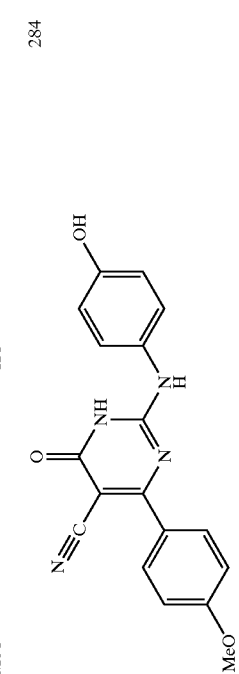 |
| 283 | 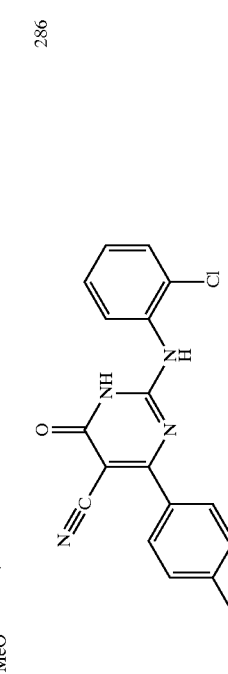 | 284 | 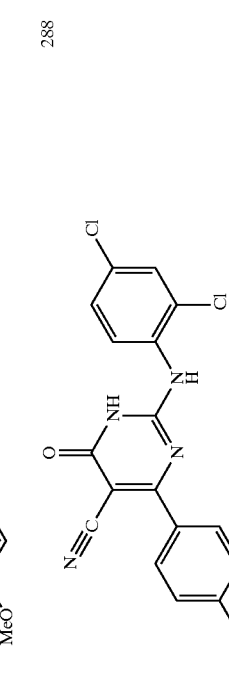 |
| 285 |  | 286 |  |
| 287 | 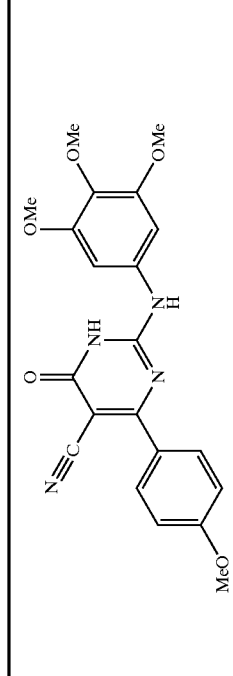 | 288 | 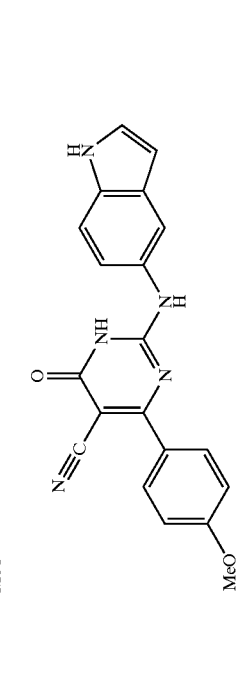 |

TABLE 1-continued

TABLE 1-continued
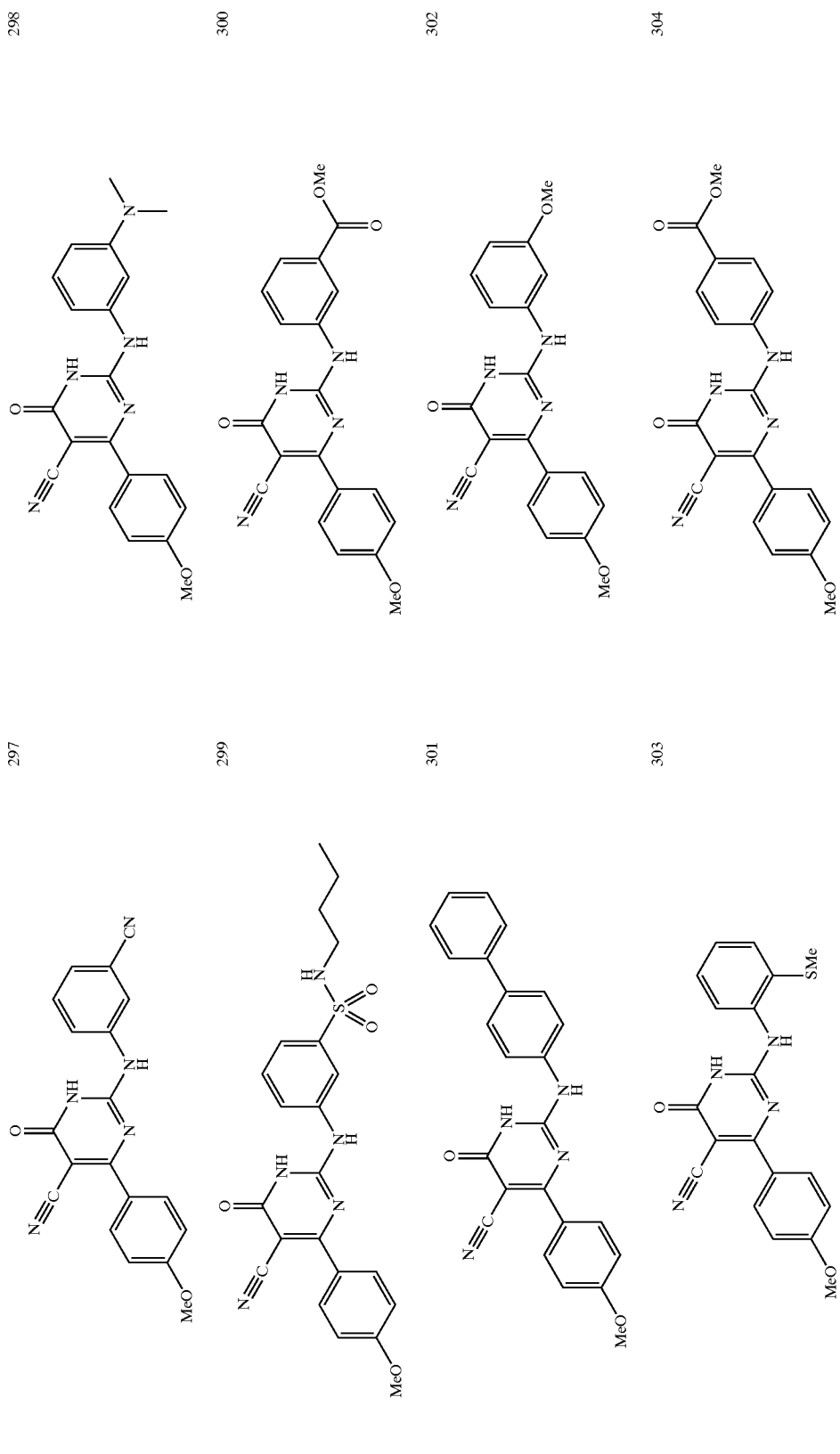

TABLE 1-continued

TABLE 1-continued

| 313 | 314 |
| 315 | 316 |
| 317 | 318 |

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of excessive moisture for at least one week.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

The compounds of this invention may be synthesized using conventional techniques. Advantageously, these compounds are conveniently synthesized from readily available starting materials. In general, the compounds of the formulae described herein are conveniently obtained via methods illustrated in General Synthetic Schemes I–IV and the Examples herein. These general schemes are also exemplified by the specific methods described in the Examples section below.

Thus, one embodiment relates to a method of making a compound of the formulae described herein, comprising synthesizing any one or more intermediates illustrated in the synthetic schemes herein and then converting that intermediate(s) to a compound of the formulae described herein. Another embodiment relates to a method of making a compound of the formulae described herein, comprising synthesizing any one or more intermediates illustrated in the examples herein and then converting that intermediate(s) to a compound of the formulae described herein. Another embodiment relates to a method of making a compound of the formulae described herein, comprising synthesizing any one or more intermediates illustrated in the synthetic schemes herein and then converting that intermediate(s) to a compound of the formulae described herein utilizing one or more of the chemical reactions described in the synthetic schemes or examples herein. Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally comprise steps, either before or after the steps described specifically herein, to add or remove suitable protecting groups in order to ultimately allow synthesis of the compound of the formulae described herein.

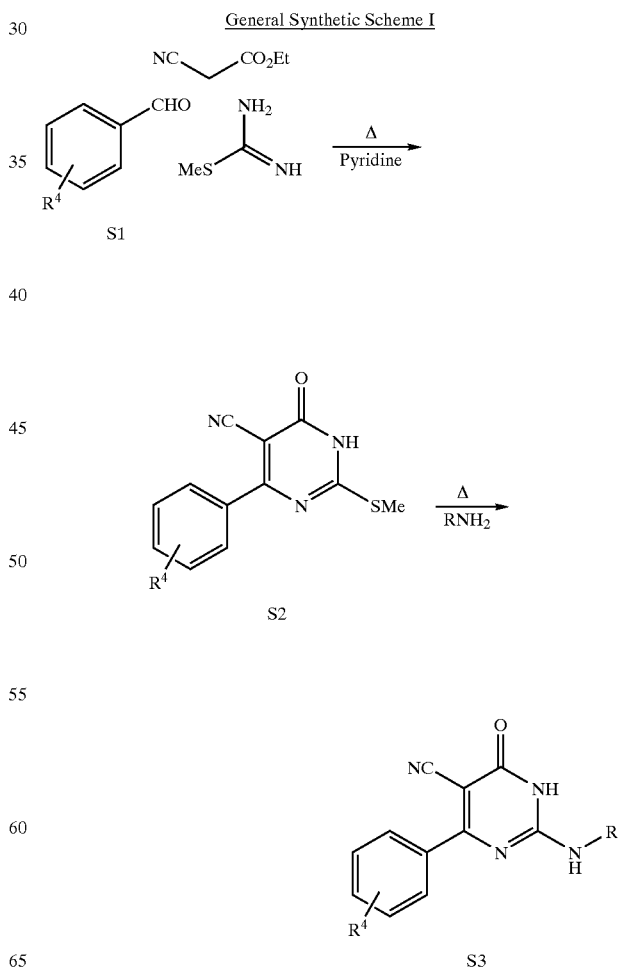

General Synthetic Scheme I

General Synthetic Scheme II

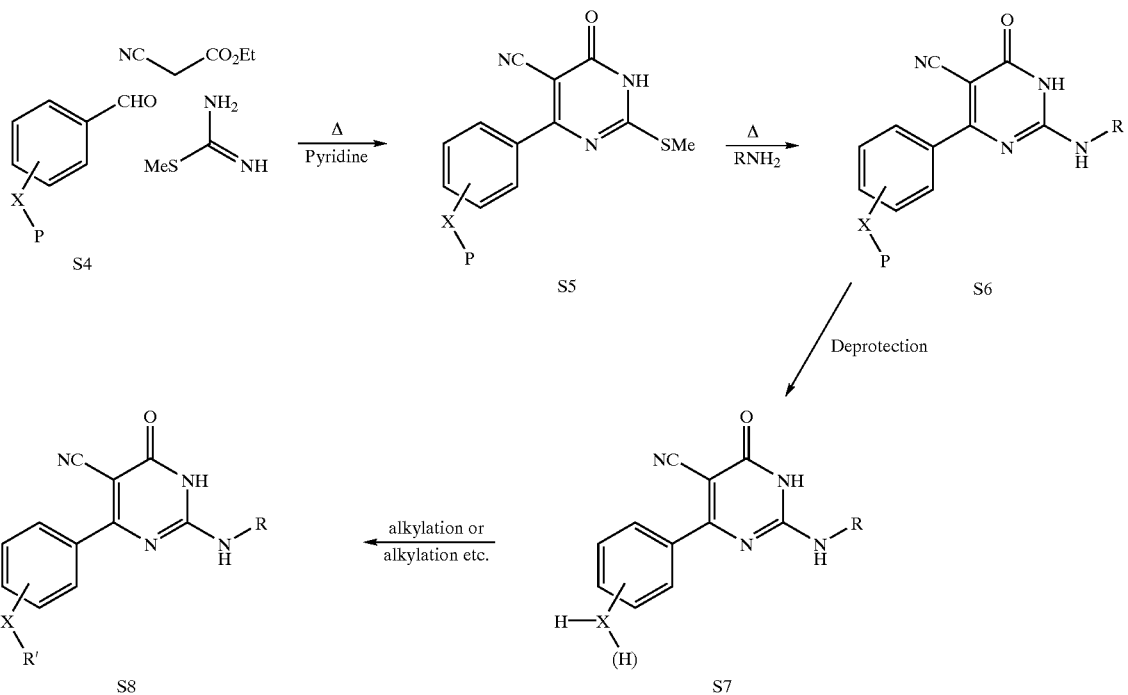

Where X = N, O, S; P = suitable protecting group and R' = alkyl or acyl

General Synthetic Scheme III

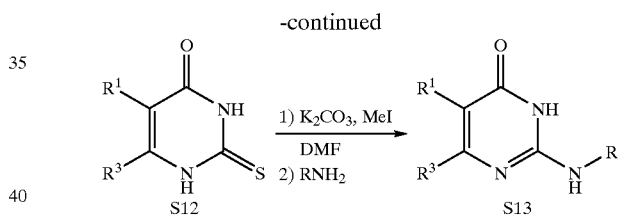

General Synthetic Scheme IV

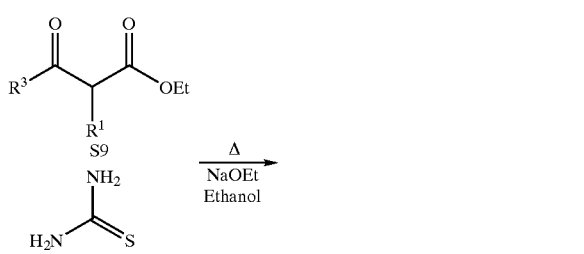

In General Synthetic Scheme I, an appropriate benzaldehyde (S1) is converted to pyrimidinone S2 by reaction with an appropriate cyanoacetate (or equivalent) S-methylisothiouronium sulphate. Pyrimidinone S2 may be reacted with a substituted aniline or amine to form pyrimidinone S3.

In a similar fashion, as illustrated in General Synthetic Scheme II, a protected benzaldehyde (S4) may be reacted under the same conditions to provide pyrimidinone S5. Pyrimidinone S5 can be subsequently reacted with an aniline, amine or other appropriate heteroatom nucleophile to provide pyrimidinone S6. Subsequent deprotection (S7) and functionalization of the resultant heteroatom provides S8.

Alternatively, as shown in General Synthetic Scheme III, an appropriately substituted β-ketoester (S9) can be condensed under similar conditions with S-methylisothiouronium sulphate to afford pyrimidinone S10. Nucleophilic addition to S10 then provides S11. Additionally, as illustrated in General Synthetic Scheme IV, an appropriately substituted β-ketoester (S9) can be condensed with thiourea to afford S12. Subsequent sulfur alkylation and nucleophilic addition provides pryimidinone S13.

Thus, one embodiment relates to a method of making a compound of the formulae described herein, comprising 1) the step of reacting an aldehyde (or equivalent) with a cyanoacetate (or equivalent) and an alkylisothiouronium salt to form a pyrimidinone; 2) reacting said pyrimidinone with a nucleophilic agent (e.g., an aniline or amine) to form the compound of the formulae described herein. Nucleophilic agents are known in the art and are described in the chemical texts and treatises referred to herein. Such agents may have carbon or a heteroatom (e.g, N, O, S) as the nucleophilic atom. In an alternate embodiment, the method of making a compound of the formulae described herein, comprises 1) preparation of a thio-substituted pyrimidone intermediate (as exemplified by S2, S5, S10 and S12 in the General Synthetic Schemes); and 2) reacting the pyrimidinone of step 1 with another chemical to form the compound of the formulae described herein. The chemicals used in the aforementioned methods may include, for example, solvents, reagents, catalysts, protecting group and deprotecting group reagents and the like. The methods described above may also additionally comprise steps, either before or after steps 1 and 2 described above, to add or remove suitable protecting groups in order to ultimately allow synthesis of the compound of the formulae described herein.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The novel compounds of the present invention are excellent ligands for protein kinases, subsequences thereof, and homologous polypeptides. Accordingly, these compounds are capable of targeting and inhibiting kinase enzyme and subsequences thereof. Inhibition can be measured by various methods, including, for example, those methods illustrated in the examples below. The compounds described herein may be used in assays, including radiolabelled, antibody detection and fluorometric, for the isolation, identification, or structural or functional characterization of enzymes, peptides or polypeptides. Such assays include any assay wherein a nucleoside or nucleotide are cofactors or substrates of the peptide of interest, and particularly any assay involving phosphotransfer in which the substrates and or cofactors are ATP, GTP, Mg, Mn, peptides or polymeric amino acids.

Pharmaceutical compositions of this invention comprise a compound of the formulae described herein or a pharmaceutically acceptable salt thereof; an additional agent selected from an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. Such compositions may optionally comprise additional therapeutic agents, including, for example, immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, alternatively between about 0.5 and about 75 mg/kg body weight per day of the kinase inhibitory compounds described herein are useful in a monotherapy and/or in combination therapy for the prevention and treatment of kinase mediated disease. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

When the compositions of this invention comprise a combination of a kinase inhibitor of the formulae described herein and one or more additional therapeutic or prophylactic agents, both the kinase inhibitor and the additional agent should be present at dosage levels of between about 10 to 100%, and more preferably between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

According to one embodiment, the pharmaceutical compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, interferon and mizoribine.

According to an alternate embodiment, the pharmaceutical compositions of this invention may additionally comprise cytotoxic or hormonal anti-cancer agents or combinations thereof. Examples of anti-cancer agents include, but are not limited to, cis-platin, actinomycin D, doxorubicin, vincristine, vinblastine, etoposide, amsacrine, mitoxantrone, tenipaside, taxol, taxotere, colchicine, cyclosporin A, phenothiazines, interferons, thioxantheres, anti-estrogens (e.g., tamoxifen), aromatase inhibitors, anti-androgens, and LHRH antagonists.

According to another alternate embodiment, the pharmaceutical compositions of this invention may additionally comprise an anti-viral agent. Examples of anti-viral agents include, but are not limited to, Cytovene, Ganciclovir, trisodium phosphonoformate, Ribavirin, d4T, ddI, AZT, amprenavir and acyclovir.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

In an alternate embodiment, this invention provides methods of treating, preventing, or relieving symptoms of disease in a mammal comprising the step of administrating to said mammal any of the pharmaceutical compositions and combinations described above. Preferably, the mammal is a human. If the pharmaceutical composition only comprises the inhibitor of this invention as the active component, such methods may additionally comprise the step of administering to said mammal an additional therapeutic agent, such as an antiinflammatory agent, immunosuppressant, an anti-cancer agent, an anti-viral agent, or an anti-vascular hyper-proliferation compound. Such additional agent may be administered to the mammal prior to, concurrently with, or following the administration of the inhibitor composition.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, for example, as illustrated below:

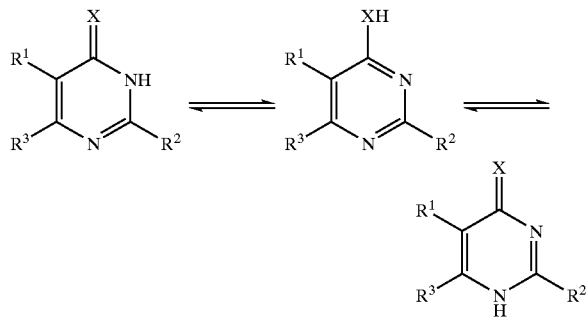

in such instances, the invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom (see below), whereby they are intended to be attached at any available atom that is not already substituted by an atom other than H (hydrogen). For example, a structure drawn as:

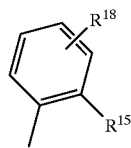

is intended to encompass all of the following structures:

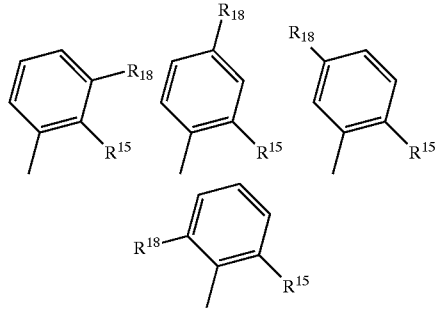

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

In order that the invention described herein may be more readily understood, the following examples are set forth. It should be understood that these examples are for illustrative purposes only and are not to be construed as limiting this invention in any manner. NMR and MS spectra obtained for compounds described in the examples below and those described herein were consistent with that of the compounds of the formulae herein.

EXAMPLE 1

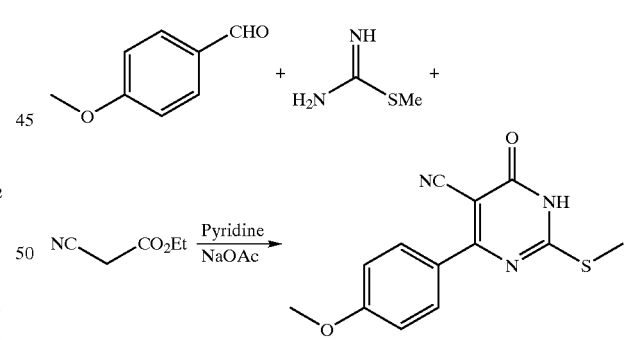

To a mixture of 1.39 g (5 mmol) S-methylisothiouronium sulphate and 1.36 g (1.22 mL; 10 mmol) in 50 mL of dry pyridine is added 1.13 g (1.06 mL; 10 mmol) of ethylcyano acetate and 5 g (61 mmol) of anhydrous sodium acetate. The mixture is refluxed (135° C.) under calcium carbonate for 4 hours. The resultant mixture is cooled and filtered under vacuum and the filtrate evaporated under high-vac. The solid product is suspended in glacial acetic acid and the resulting suspension was evaporated under high-vac. The solid is then suspended in dichloromethane, filtered, and is washed with excess dichloromethane to provide product of purity sufficient for subsequent manipulations.

EXAMPLE 2

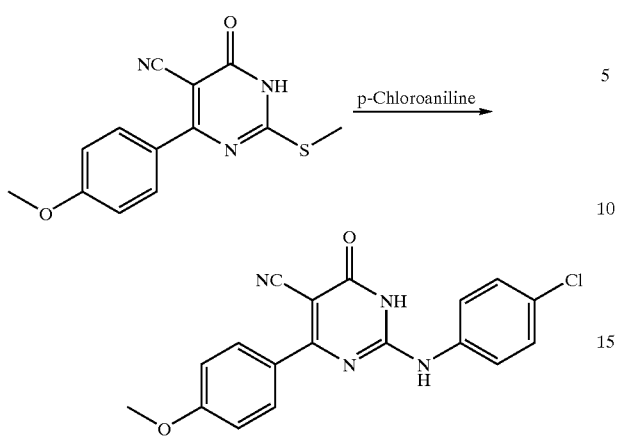

A mixture of 25 mg (0.09 mmol) of the product from Example 1 and 200 mg of p-chloroaniline is heated by heat gun until a homogeneous solution is obtained. The reaction is heated at 170° C. until such time as the solution solidifies. The product is broken up and suspended in dichloromethane and filtered while washing with excess dichloromethane.

EXAMPLE 3

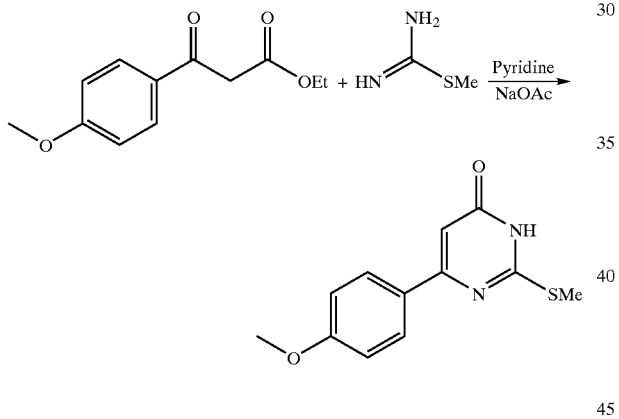

To a solution of 360 mg (1.6 mmol) of ketoester in 5 mL of anhydrous pyridine is added 451 mg (1.6 mmol) of S-methylisothiouronium sulphate and 1.33 g (16.2 mmol) of anhydrous sodium acetate. The mixture is refluxed (135° C.) under calcium carbonate for 7 hours. The resultant mixture is cooled and filtered under vacuum and the filtrate evaporated under high-vac. The solid product is suspended in glacial acetic acid and the resulting suspension is evaporated under high-vac. The solid is then re-suspended in diethylether, filtered, and washed with excess diethylether to provide product of purity sufficient for subsequent manipulations.

EXAMPLE 4

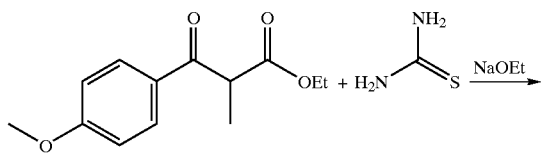

-continued

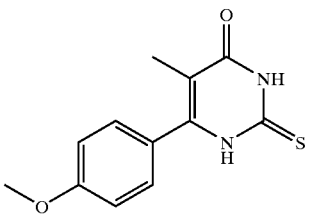

A dry two-necked flask fitted with reflux condenser is charged, under argon, with 126 mg (5.5 mmol) sodium metal and 3 mL absolute ethanol. The sodium is dissolved with mild heating over about one hour. To this solution is added 292 mg (3.8 mmol) of thiourea. After brief stirring, 646 mg (2.7 mmol) ketoester in one mL absolute ethanol is added followed by an additional one mL of absolute ethanol containing residual ketoester from the transfer vessel. The solution is refluxed for five hours at which time it is cooled and evaporated to dryness. The residue is taken up in water, neutralized with glacial acetic acid, and extracted into ethyl acetate (2×25 mL). The organic layer is separated, dried over magnesium sulfate, filtered, and evaporated under vacuum. The residue is recrystallized from ethanol to yield pure product.

EXAMPLE 5

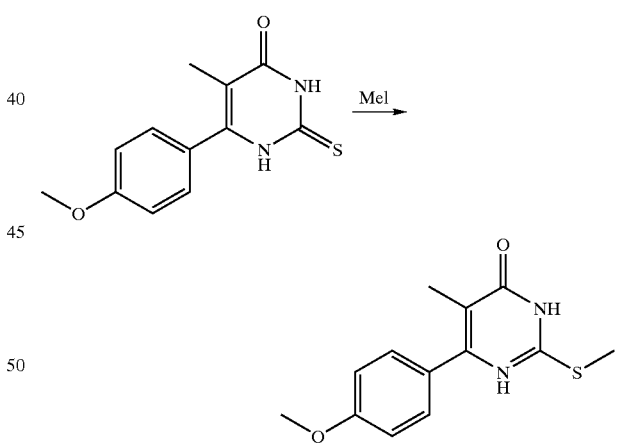

To a solution of 161 mg (0.65 mmol) of pyrimidinone in 5 mL of DMF is added 90 mg (0.65 mmol) pulverized potassium carbonate and 44 μL (0.70 mmol) of methyl iodide. The suspension is stirred under argon for one hour at which point it is added to water (5 mL). The water is extracted with ethyl acetate (2×25 mL) and the organic layer is dried over magnesium sulfate, filtered and evaporated under vacuum. The resulting residue is of sufficient-purity to be utilized directly in subsequent reactions.

EXAMPLE 6

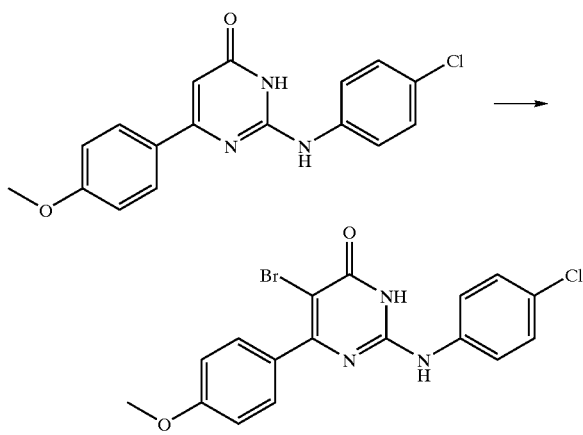

To a solution of 39 mg (0.12 mmol) pyrimidinone in 1 mL of DMF is added 21 mg (0.12 mmol) N-bromosuccinimide. After stirring for 5 minutes, the reaction is quenched with a few drops of saturated aqueous sodium bisulfite. The solution is then diluted with ethyl acetate and the resulting precipitate is filtered to provide pure bromide. The ethyl acetate is washed with water (2×2 mL), dried over magnesium sulfate, filtered, and evaporated under vacuum to provide additional crude product.

EXAMPLE 7

The inhibitor compounds described herein are screened in the following manner. Kinases suitable for use in the following protocol to determine kinase activity of the compounds described herein include, but are not limited to: Lck, Lyn, Src, Fyn, Syk, Zap-70, Itk, Tec, Btk, EGFR, ErbB2, Kdr, Flt-1, Flt-3, Tek, c-Met, InsR.

Kinases are expressed as either kinase domains or full length constructs fused to glutathione S-transferase (GST) or polyHistidine tagged fusion proteins in either *E. coli* or Baculovirus-High Five expression systems. They are purified to near homogeneity by affinity chromatography essentially as previously described (Lehr et al., 1996; Gish et al., 1995). In some instances, kinases are co-expressed or mixed with purified or partially purified regulatory polypeptides prior to measurement of activity.

Kinase activity and inhibition are measured essentially by established protocols (Braunwalder et al., 1996). Briefly, The transfer of $^{33}PO_4$ from ATP to the synthetic substrates poly(Glu, Tyr) 4:1 or poly(Arg, Ser) 3:1 attached to the bioactive surface of microtiter plates serves as the basis to evaluate enzyme activity. After an incubation period, the amount of phosphate transferred is measured by first washing the plate with 0.5% phosphoric acid, adding liquid scintillant, and then counting in a liquid scintillation detector. The $IC_{50}$ is determined by the concentration of compound that causes a 50% reduction in the amount of $^{33}P$ incorporated onto the substrate bound to the plate.

Other similar methods whereby phosphate is transferred to peptide or polypeptide substrate containing tyrosine, serine, threonine, or histidine, either alone, in combination, or in combination with other amino acids, in solution or immobilized (i.e., solid phase) are also useful. Alternatively, kinase activity can be measured using antibody-based methods whereby an antibody or polypeptide is used as a reagent to detect phosphorylated target polypeptide. The compounds of the invention described herein are potent and selective kinase inhibitors as demonstrated by representative compounds described herein that inhibit one or more kinases with $IC_{50}$ values at less than about 5 μM or greater, at less than about 1 μM, or at less than about 300 nM.

REFERENCES

Braunwalder A F, Yarwood D R, Hall T, Missbach M, Lipson K E, Sills M A. (1996). A solid-phase assay for the determination of protein tyrosine kinase activity of c-src using scintillating microtitration plates. *Anal. Biochem.* 234(1):23–26.

Gish G, McGlone M L, Pawson T, Adams J A. (1995). Bacterial expression, purification and preliminary kinetic description of the kinase domain of v-fps. *Protein Eng.* 8(6):609–614.

Lehr R V, Ma Y G, Kratz D, Brake P G, Wang S, Faltynek C R, Wang X M, Stevis P E (1996). Production, purification and characterization of non-myristylated human T-cell protein tyrosine kinase in a baculovirus expression system. *Gene* 169(2):27527–9.

EXAMPLE 8

The cellular activities of the inhibitor compounds described herein may be assessed in a number of assays known to those skilled in the art, some of which are exemplified as described below. Typical sources for cells include, but are not limited to, human bone marrow or peripheral blood lymphocytes, or their equivalents, or rodent spleen cells. Transformed cell lines that have been reported as cytokine- and growth factor-dependent cells are available from standard cell banks such as The American Type Culture Collection (Bethesda, Md.). Cells genetically manipulated to express a particular kinase or kinases are also suitable for use in assaying cellular activity. These cells are grown in various standard tissue culture media available from suppliers such as GIBCO/BRL (Grand Island, N.Y.) supplemented with fetal bovine serum. Cellular activity may also be measured using bacterial, yeast, or virally infected mammalian cells. Standard inhibitors of cell activation include mycophenolic acid (SIGMA, St. Louis, Mo.), staurosporine (Calbiochem, San Diego, Calif.), wortmannin (Calbiochem), cyclosporine, FK-506, and steroids (e.g., corticosteroids).

The compound(s) are tested for activity in cellular assays of T or B cell activation. For example, the receptor-induced production of cytokines and/or cell proliferation is a useful measure. This assay is performed similarly to techniques described in the literature (1,2), and involves antibody-, antigen-, mitogen-, or antigen presenting cell-mediated crosslinking of the T cell or B cell receptor with or without engagement of co-stimulatory receptors.

The compound(s) are tested for activity in cellular assays of allergic mediator release. For example, the receptor-induced degranulation in mast cells or basophils leading to histamine release and the production of cytokines is a useful measure. This assay is performed similarly to techniques described in the literature (3), and involves crosslinking of antigen-specific IgE on cells leading to degranulation and or cytokine production.

The compound(s) are tested for activity in cellular assays of growth factor effects. For example, growth factor receptor-induced signaling in a cell leading to intracellular signaling events such as kinase autophosphorylation, phosphorylation of relevant kinase substrates, phosphorylation of MAP kinases, or induction of gene expression. Also, for example, growth factor-induced functional events in cells such as DNA synthesis, proliferation, migration, or apoptosis. These assays are performed similarly to techniques described in the literature (4–7), and involve addition of growth factor to responsive cells followed by monitoring of signaling or functional events.

The compound(s) are tested for activity in cellular assays of cytokine activation. For example, cytokine-induced intracellular signaling events and/or cell proliferation and/or cytokine production are a useful measure. This assay is performed similarly to techniques described in the literature (8), and involves addition of cytokine to responsive cells followed by monitoring intracellular signaling events and/or cell proliferation and/or cytokine production.

REFERENCES

1. Shuji, K., et al. Activation of p21-CDC42/Rac-activated kinases by CD28 signaling: p21-activated kinase (PAK) and MEK kinase 1 (MEKK1) may mediate the interplay between CD3 and CD28 signals. *J. Immunol.* 160: 4182–4189 (1998).
2. Satterthwaite, A. B., et al., Independent and opposing roles for Btk and Lyn in B cell and rhyeloid signaling pathways. *J. Exp. Med.* 188: 833–844 (1998).
3. Stephan, V., et al. FcεR1-induced protein tyrosine phosphorylation of pp72 in rat basophilic leukemia cells (RBL-2H3). *J. Biol. Chem.* 267 (8): 5434–5441 (1992).
4. Olayioye, M. A., et al. ErbB-1 and ErbB-2 acquire distinct signaling properties dependent upon their dimerization partner. *Molecular and Cellular Biology.* 18(9): 5042–5051 (1998).
5. Buchdunger, E., et al. Inhibition of the Abl protein-tyrosine kinase in vitro and in vivo by a 2-phenylaminopyrimidine derivative. *Cancer Res.* 56;101–104 (1996).
6. Yoshida, A. et al., Differential endothelial migration and proliferation to basic fibroblast growth factor and vascular endothelial growth factor. *Growth Factors.* 13:57–64 (1996).
7. Brunet, A., et al., Akt promotes cell survival by phosphorylating and inhibiting a forkhead transcription factor. *Cell.* 96:857–868 (1999).
8. Liu, K. D., et al. Janus kinases in interleukin-2-mediated signaling: JAK1 and JAK3 are differentially regulated by tyrosine phosphorylation. *Current Biology.* 7 (11): 817–826 (1997).

While we have described a number of embodiments of this invention, it is apparent that our basic examples may be altered to provide other embodiments that utilize the products and processes of this invention. Therefore, it will be appreciated that the scope of this invention is to be defined by the claims rather than by the specific embodiments that have been represented by way of example.

What is claimed is:
1. A compound having the formula

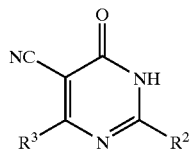

or a pharmaceutically acceptable salt thereof, wherein $R^2$ is —NH-aryl;
$R^3$ is a phenyl substituted with 1–3 independent $R^4$;
wherein each $R^4$ is independently selected from H; C1–C10 alkyl; C2–C10 alkenyl; C2–C10 alkynyl; C3–C10 cycloalkyl; C4–C10 cycloalkenyl; aryl; $R^8$; halo; haloalkyl; $SR^5$; $OR^5$; $NR^5R^5$; $COOR^5$; $NO_2$; CN; $C(O)R^5$; $C(O)C(O)R^5$; $C(O)NR^5R^5$; $OC(O)R^5$; $S(O)_2R^5$; $S(O)_2NR^5R^5$; $NR^5C(O)NR^5R^5$; $NR^5C(O)C(O)R^5$; $NR^5C(O)R^5$; $NR^5(COOR^5)$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; $NR^5C(O)C(O)NR^5R^6$; C1–C10 alkyl substituted with aryl, $R^7$ or $R^8$; or C1–C10 alkenyl substituted with aryl, $R^7$ or $R^8$;
each $R^5$ is independently H; C1–C10 alkyl; C2–C10 alkenyl; C2–C10 alkynyl; C3–C10 cycloalkyl; C4–C10 cycloalkenyl; aryl; $R^9$; C1–C10 alkyl substituted with 1–3 independent aryl, $R^7$ or $R^9$ groups; C3–C10 cycloalkyl substituted with 1–3 independent aryl, $R^7$ or $R^9$ groups; or C1–C10 alkenyl substituted with 1–3 independent aryl, $R^7$ or $R^9$;
each $R^6$ is independently $C(O)R^5$, $COOR^5$, or $S(O)_2R^5$;
each $R^7$ is independently halo, $CF_3$, $SR^{10}$, $OR^{10}$, $OC(O)R^{10}$, $NR^{10}R^{10}$, $NR^{10}R^{11}$, $NR^{11}R^{11}$, $COOR^{10}$, $NO_2$, CN, $C(O)R^{10}$, or $C(O)NR^{10}R^{10}$;
each $R^8$ is independently a 5–8 membered monocyclic, 8–12 membered bicyclic, or 11–14 membered tricyclic ring system having 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; aryl; $R^9$; halo; sulfur; oxygen; haloalkyl; $SR^5$; $OR^5$; $OC(O)R^5$; $NR^5R^5$; $NR^5R^6$; $NR^6R^6$; $COOR^5$; $NO_2$; CN; $C(O)R^5$; $C(O)NR^5R^5$; C1–C10 alkyl substituted with 1–3 independent $R^7$, $R^9$ or aryl; or C1–C10 alkenyl substituted with 1–3 independent $R^7$, $R^9$ or aryl;
each $R^9$ is independently a 5–8 membered monocyclic, 8–12 membered bicyclic, or 11–14 membered tricyclic ring system having 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; C2–C10 alkenyl; C2–C10 alkynyl; C3–C10 cycloalkyl; C4–C10 cycloalkenyl; halo; sulfur; oxygen; $CF_3$; haloalkyl; $SR^{10}$; $OR^{10}$; $NR^{10}R^{10}$; $NR^{10}R^{11}$; $NR^{11}R^{11}$; $COOR^{10}$; $NO_2$; CN; $C(O)R^{10}$; or $C(O)NR^{10}R^{10}$;
each $R^{10}$ is independently H, C1–C10 alkyl; C2–C10 alkenyl; C2–C10 alkynyl; C3–C10 cycloalkyl; C4–C10 cycloalkenyl; haloalkyl; C1–C10 alkyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$; or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$;
each $R^{11}$ is independently $C(O)R^{10}$, $COOR^{10}$, or $S(O)_2R^{10}$;
each $R^{12}$ is independently H, C1–C10 alkyl, C2–C10 alkenyl, C2–C10 alkynyl, C3–C10 cycloalkyl, C4–C10 cycloalkenyl, or phenyl optionally substituted with 1–3 independent C1–C10 alkyl, C2–C10 alkenyl, C2–C10 alkynyl, C3–C10 cycloalkyl, C4–C10 cycloalkenyl, halo, $CF_3$, $OR^{13}$, $SR^{13}$, $NR^{13}R^{13}$, $COOR^{13}$, $NO_2$, CN, $C(O)R^{13}$, $C(O)NR^{13}R^{13}$, $NHC(O)R^{13}$, or $OC(O)R^{13}$;

each $R^{13}$ is independently H; C1–C10 alkyl; C2–C10 alkenyl; C2–C10 alkynyl; C3–C10 cycloalkyl; C4–C10 cycloalkenyl; C1–C10 alkyl optionally substituted with halo, $CF_3$, $OR^{19}$, $SR^{19}$, $NR^{19}R^{19}$, $COOR^{19}$, $NO_2$, CN; or phenyl optionally substituted with halo, $CF_3$, $OR^{19}$, $SR^{19}$, $NR^{19}R^{19}$, $COOR^9$, $NO_2$, CN;

each $R^{19}$ is independently H; C1–C10 alkyl; C3–C10 cycloalkyl or phenyl;

each haloalkyl is independently a C1–C10 alkyl substituted with one or more halogen atoms, selected from F, Cl, Br, or I, wherein the number of halogen atoms may not exceed that number that results in a perhaloalkyl group; and each aryl is independently a 6-carbon monocyclic or 10-carbon bicyclic aromatic ring system optionally substituted with 1–3 independent C1–C10 alkyl; C2–C10 alkenyl; C2–C10 alkynyl; C3–C10 cycloalkyl; C4–C10 cycloalkenyl; $R^9$; halo; haloalkyl; $OR^{12}$; $SR^{12}$; $NR^{12}R^{12}$; $COOR^{12}$; $NO_2$; CN; $C(O)R^{12}$; $C(O)C(O)R^{12}$; $C(O)NR^{12}R^{12}$; $S(O)_2R^{12}$; $N(R^{12})C(O)R^{12}$; $N(R^{12})(COOR^{12})$; $N(R^{12})S(O)_2R^{12}$; $S(O)_2NR^{12}R^{12}$; $OC(O)R^{12}$; $NR^{12}C(O)NR^{12}R^{12}$; $NR^{12}C(O)C(O)R^{12}$; $NR^{12}C(O)R^9$; $NR^{12}S(O)_2NR^{12}R^{12}$; $NR^{12}S(O)_2R^9$; $NR^{12}C(O)C(O)NR^{12}R^{12}$; C1–C10 alkyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$; C2–C10 alkenyl substituted with 1–3 independent $R^9$, halo, $CF_3$, $OR^{12}$, $SR^{12}$, $NR^{12}R^{12}$, $COOR^{12}$, $NO_2$, CN, $C(O)R^{12}$, $C(O)NR^{12}R^{12}$, $NHC(O)R^{12}$, $NH(COOR^{12})$, $S(O)_2NR^{12}R^{12}$, $OC(O)R^{12}$; or $R^{12}$; and provided that (1) $R^2$ is other than unsubstituted phenyl-NH—; (2) when $R^3$ is 4-methoxyphenyl, then $R^2$ is other than 4-methoxyphenyl-NH— or 4-nitrophenyl-NH—; and (3) when $R^3$ is 2,4-dichlorophenyl, then $R^2$ is other than 4-chlorophenyl-NH—.

2. The compound of claim 1 or a pharmaceutically acceptable salt thereof, wherein $R^2$ is naphthyl-NH— or phenyl-NH—, wherein the phenyl is substituted by 1–3 radicals independently selected from the group consisting of $R^9$; $R^{12}$; halo; $CF_3$; $OR^{12}$; $SR^{12}$; $NR^{12}R^{12}$; $COOR^{12}$; $NO_2$; CN; $C(O)NR^{12}R^{12}$; $S(O)_2NR^{12}R^{12}$; and C1–C10 alkyl substituted with $OR^{12}$.

3. The compound of claim 2 or a pharmaceutically acceptable salt thereof, wherein $R^3$ is a phenyl substituted with 1–3 independent $R^4$;

wherein each $R^4$ is independently selected from H; C1–C10 alkyl; $R^8$; halo; $CF_3$; $OR^5$; $NR^5R^5$; $COOR^5$; $NO_2$; CN; $NR^5C(O)NR^5R^5$; $NR^5C(O)C(O)R^5$; $NR^5C(O)R^5$; $NR^5C(O)R^8$; $NR^5S(O)_2NR^5R^5$; $NR^5S(O)_2R^5$; $NR^5S(O)_2R^8$; $NR^5C(O)C(O)NR^5R^5$; or $NR^5C(O)C(O)NR^5R^6$;

each $R^5$ is independently H; C1–C10 alkyl; C2–C10 alkenyl; aryl; $R^9$; C1–C10 alkyl substituted with 1–3 independent aryl, $R^7$ or $R^9$ groups; or C3–C10 cycloalkyl substituted with $R^7$;

each $R^6$ is independently $C(O)R^5$;

each $R^7$ is independently halo, $OR^{10}$, $N^{10}R^{10}$, or $COOR^{10}$;

each $R^8$ is independently a 5–8 membered monocyclic, 8–12 membered bicyclic, or 11–14 membered tricyclic ring system having 1–3 heteroatoms if monocyclic, 1–6 heteroatoms if bicyclic, or 1–9 heteroatoms if tricyclic, said heteroatoms selected from O, N, or S, which may be saturated or unsaturated, and wherein 0, 1, 2 or 3 atoms of each ring may be substituted by a substituent independently selected from C1–C10 alkyl; aryl; $R^9$; halo; sulfur; oxygen; $SR^5$; $NR^5R^6$; $NO_2$; or $C(O)R^5$;

each $R^9$ is independently a 5–8 membered monocyclic ring system having 1–3 heteroatoms selected from O, N, or S, which may be saturated or unsaturated, and optionally substituted by $NO_2$;

each $R^{10}$ is independently H, C1–C10 alkyl; C1–C10 alkyl substituted with $OR^{13}$; or phenyl;

each $R^{12}$ is independently H, C1–C10 alkyl, or phenyl;

each $R^{13}$ is independently C1–C10 alkyl; or C1–C10 alkyl optionally substituted with $OR^{19}$;

each $R^{19}$ is independently C1–C10 alkyl; and each aryl is independently a 6-carbon monocyclic or 10-carbon bicyclic aromatic ring system optionally substituted with 1–3 independent halo; $OR^{12}$; $NR^{12}R^{12}$; $NO_2$; $N(R^{12})C(O)R^{12}$; or $R^{12}$.

4. The compound of claim 3 or a pharmaceutically acceptable salt thereof, wherein $R^2$ is naphthyl-NH— or phenyl-NH—, wherein the phenyl is substituted by 1–3 radicals independently selected from the group consisting of halo; $CF_3$; $NO_2$; CN; $C(O)NH_2$; $S(O)_2NH_2$; hydroxy; methoxy; phenoxy, methylthio; C1–C4 alkyl; phenyl; hydroxymethyl; hydroxyethyl; dimethylamino; and a 5–8 membered monocyclic ring system having 1–3 heteroatoms selected from O, N, or S, which may be saturated or unsaturated.

5. A pharmaceutical composition comprising a compound according to any one of claims 1–4 and a pharmaceutically acceptable carrier, adjuvant or vehicle.

* * * * *

UNITED STATES PATENT AND TRADEMARK OFFICE
CERTIFICATE OF CORRECTION

PATENT NO. : 6,495,558 B1
DATED : December 17, 2002
INVENTOR(S) : Armistead et al.

It is certified that error appears in the above-identified patent and that said Letters Patent is hereby corrected as shown below:

Column 8,
Line 19, change "$NR^5\text{-}R^{16}$" to -- $NR^5\text{-}NR^5R^{16}$ --.

Column 14,
Line 25, change "C3-Cor cycloalkyl" to -- C3-C10 cycloalkyl --.

Column 16,
Line 5, change "$NR^{12}C(O)R^{12}$" to -- $NR^{12}C(O)R^9$ --.

Column 18,
Lines 31 and 36, change "C1-C1" to -- C1-C10 --.

Column 20,
Line 66, change "$NR^{15}R^5$" to -- $NR^5R^{15}$ --.

Column 127,
Line 52, change "quatemization" to -- quaternization --.

Signed and Sealed this

Eleventh Day of March, 2003

JAMES E. ROGAN
*Director of the United States Patent and Trademark Office*